(12) United States Patent
Brady et al.

(10) Patent No.: US 11,325,920 B2
(45) Date of Patent: May 10, 2022

(54) ANTIBACTERIAL COMPOUNDS, COMPOSITIONS THEREOF, AND METHODS USING SAME

(71) Applicant: The Rockefeller University, New York, NY (US)

(72) Inventors: Sean Brady, New York, NY (US); James Peek, New York, NY (US)

(73) Assignee: The Rockefeller University, New York, NY (US)

( * ) Notice: Subject to any disclaimer, the term of this patent is extended or adjusted under 35 U.S.C. 154(b) by 13 days.

(21) Appl. No.: 16/964,317

(22) PCT Filed: Jan. 24, 2019

(86) PCT No.: PCT/US2019/014877
§ 371 (c)(1),
(2) Date: Jul. 23, 2020

(87) PCT Pub. No.: WO2019/147753
PCT Pub. Date: Aug. 1, 2019

(65) Prior Publication Data
US 2021/0139509 A1 May 13, 2021

Related U.S. Application Data

(60) Provisional application No. 62/621,160, filed on Jan. 24, 2018.

(51) Int. Cl.
*C07D 519/00* (2006.01)
*A61P 31/06* (2006.01)

(52) U.S. Cl.
CPC .......... *C07D 519/00* (2013.01); *A61P 31/06* (2018.01)

(58) Field of Classification Search
CPC ............................. C07D 519/00; A61P 31/06
USPC ........................................................ 514/450
See application file for complete search history.

(56) References Cited

U.S. PATENT DOCUMENTS

| | | | |
|---|---|---|---|
| 5,786,350 A | 7/1998 | Occelli | |
| 2005/0261262 A1 | 11/2005 | Ma | |
| 2014/0356376 A1 | 12/2014 | Brown | |
| 2018/0021450 A1 | 1/2018 | Brown | |

FOREIGN PATENT DOCUMENTS

| | | |
|---|---|---|
| WO | 2019147753 | 8/2019 |
| WO | 2020021252 A1 | 1/2020 |

OTHER PUBLICATIONS

"4-[1-[(7S,9E,11S,12R,13S,14R,15R,16S,17R,18S,19E,21Z)-11-[[(3Ar,4R,6R,7aS)-4-methyl-4,6,7,7a-tetrahydro-3aH-[1,3]dioxolo[4,5-c]pyran-6-yl]oxy]-13-acetyloxy-2,15,17-trihydroxy-3,7,12,14,16,22-hexamethyl-6,23,27,29-tetraoxo-8,30-dioxa-24-aza tetracyclo[23.3.1.14,7.05,28]triaconta-1(28),2,4,9,19,21,25-heptaen-18-yl]ethoxy]-3,3-dimethyl-4-oxobutanoic acid | C50H63NO19", PubChem Compound, (Dec. 18, 2015), Database accession No. CID 101617059, URL: NCBI, XP055629974.
Altschul et al., 1990, "Basic Local Alignment Search Tool", Journal of Molecular Biology, 215:403-410.
Aristoff PA et al., 2010, "Rifamycins-obstacles and opportunities", Tuberculosis (Edinb), 90:94-118.
Artsimovitch et al., 2005, "Allosteric modulation of the RNA polymerase catalytic reaction is an essential component of transcription control by rifamycins", Cell, 122:351-363.
Bacchi et al., 1998, "Comprehensive study on structure-activity relationships of rifamycins: discussion of molecular and crystal structure and spectroscopic and thermochemical properties of rifamycin O", J Med Chem, 41:2319-2332.
Banker, G.S et al., "Modern Pharmaceutics, 3ed ", Marcel Dekker, New York, 1996, p. 596 (Year: 1996).
Barnard et al., 2008, "Rapid molecular screening for multidrug-resistant tuberculosis in a high-volume public health laboratory in South Africa", Am J Respir Crit Care Med, 177:787-792.
Bhullar et al., 2012, "Antibiotic resistance is prevalent in an isolated cave microbiome", PLoS One, 7:e34953.
Bihlmaier et al., 2006, "Biosynthetic gene cluster for the polyenoyltetramic acid alpha-lipomycin", Antimicrob Agents Chemother, 50:2113-2121.
Brady, 2007, "Construction of soil environmental DNA cosmid libraries and screening for clones that produce biologically active small molecules", Nat. Protoc., 2:1297-12305.
Brassier et al., 2006, "Performance of the genotype MTBDR line probe assay for detection of resistance to rifampin and isoniazid in strains of *Mycobacterium tuberculosis* with low- and high-level resistance", J Clin Microbiol, 44:3659-3664.
Campbell EA et al., 2001, "Structural mechanism for rifampicin inhibition of bacterial rna polymerase", Cell, 104:901-912.
Cavusoglu et al., 2002, "Characterization of rpoB mutations in rifampinresistant clinical isolates of *Mycobacterium tuberculosis* from Turkey by DNA sequencing and line probe assay", J Clin Microbiol, 40:4435-4438.
Charlop-Powers Z et al., 2015, "Global biogeographic sampling of bacterial secondary metabolism", Elife, 4:e05048.
D'Costa et al., 2006, "Sampling the antibiotic resistome", Science,311:374-377.
D'Costa et al., 2011, "Antibiotic resistance is ancient", Nature, 477:457-461.

(Continued)

*Primary Examiner* — Kahsay Habte
(74) *Attorney, Agent, or Firm* — Riverside Law LLP

(57) ABSTRACT

The present disclosure includes novel compounds useful as antimicrobial agents. The present disclosure further includes methods useful. The present disclosure further includes compositions and methods for treating or preventing a bacterial infection. The present disclosure further includes compositions and methods useful for preventing or reducing the growth or proliferation of microorganisms.

20 Claims, 27 Drawing Sheets

Specification includes a Sequence Listing.

(56) References Cited

OTHER PUBLICATIONS

Daniel, R, 2005, "The metagenomics of soil", Nat Rev Microbiol., 3:470-478.

Edgar et al., 2004, "MUSCLE: multiple sequence alignment with high accuracy and high throughput", Nucleic Acids Res., 32:1792-1797.

Edgar et al., 2010, "Search and clustering orders of magnitude faster than BLAST", Bioinformatics, 26:2460-2461.

Everest et al., 2011, "Evaluation of the antibiotic biosynthetic potential of the genus *Amycolatopsis* and description of *Amycolatopsis circi* sp. nov., *Amycolatopsis equina* sp. nov. and *Amycolatopsis hippodromi* sp. nov." J Appl Microbiol, 111:300-311.

Fernandez et al., 1998, "Identification of two genes from Streptomyces argillaceus encoding glycosyltransferases involved in transfer of a disaccharide during biosynthesis of the antitumor drug mithramycin", J. Bacteriol., 180:4929-4937.

Floss et al., 2011, "The biosynthesis of 3-amino-5-hydroxybenzoic acid (AHBA), the precursor of mC7N units in ansamycin and mitomycin antibiotics: a review", J Antibiot (Tokyo), 64:35-44.

Gold et al., 2015, "Rapid, Semiquantitative Assay To Discriminate among Compounds with Activity against Replicating or Nonreplicating *Mycobacterium tuberculosis*", Antimicrob. Agents Chemother., 59:6521-6538.

Gonzalez-y-Merchand JA et al., 1996, "The rRNAoperons of *Mycobacterium smegmatis* and *Mycobacterium tuberculosis*: comparison of promoter elements and of neighbouring upstream genes", Microbiology, 142:667-674.

He et al., 2017, "Identification of candidate genes involved in isoquinoline alkaloids biosynthesis in Dactylicapnos scandens by transcriptome analysis", Sci Rep, 7:9119.

Hubin et al., 2017, "Structure and function of the mycobacterial transcription initiation complex with the essential regulator RbpA", Elife, 6:e22520.

Huitu et al., 2009, "PCR screening of 3-amino-5-hydroxybenzoic acid synthase gene leads to identification of ansamycins and AHBA-related antibiotic producers in Actinomycetes", J Appl Microbiol, 106:755-763.

Ikezawa et al., 2003, "Molecular cloning and characterization of CYP719, a methylenedioxy bridgeforming enzyme that belongs to a novel P450 family, from cultured Coptis japonica cells", J Biol Chem, 278:38557-38565.

International Search Report and Written Opinion for PCT/US20/43226 dated Oct. 26, 2020.

Jin et al. 'Synthesis and Structure-Activity Relationships of Novel Substituted 8-amino, 8-thio, and 1,8-Pyrazote Congeners of Antitubercular Rifamycin S and Rifampin', Bioorg Med Chem Lett. Oct. 15, 2011:21(20): 6049.

Johansen et al., 2003, "Direct detection of multidrug-resistant *Mycobacterium tuberculosis* in clinical specimens in low- and high-incidence countries by line probe assay", J Clin Microbiol, 41:4454-4456.

Kang HS et al., 2014, "Arixanthomycins A-C: Phylogeny-guided discovery of biologically active eDNA derived pentangular polyphenols", ACS Chem Biol, 9:1267-1272.

Kumar P et al., 2018, "Synergistic Lethality of a Binary Inhibitor of *Mycobacterium tuberculosis* KasA", mBio, 9:e02101-e02117.

Lee SH et al., 2016, "TarO-specific inhibitors of wall teichoic acid biosynthesis restore beta-lactam efficacy against methicillin-resistant staphylococci", Sci. Transl. Med., 8:329ra32.

Li J et al., 2007, "Preparation and in vitro anti-*Staphylococcal* activity of novel 11-deoxy-11-hydroxyiminorifamycins", Bioorg. Med. Chem. Lett., 17:5510-5513.

Ma et al., 2006, "Antimycobacterium Agents. In Comprehensive Medicinal Chemistry II", Science, 7:699-739.

Moghazeh SL et al., 1996, "Comparative antimycobacterial activities of rifampin, rifapentine, and KRM-1648 against a collection of rifampin-resistant *Mycobacterium tuberculosis* isolates with known rpoB mutations", Antimicrob. Agents Chemother., 40:2655-2657.

Mosaei et al. "Mode of Action of Kanglemycin A, an Ansamycin Natural Product that Is Active against Rifampicin-Resistant *Mycobacterium tuberculosis*", Molecular Cell. 2018. vol. 72, pp. 263-274.

Murphy CK et al., 2006, "In vitro activity of novel rifamycins against rifamycin-resistant *Staphylococcus aureus*", Antimicrob. Agents Chemother., 50:827-834.

Muthaiah et al., 2017, "Prevalence of mutations in genes associated with rifampicin and isoniazid resistance in *Mycobacterium tuberculosis* clinical isolates", Journal of Clinical Tuberculosis and Other Mycobacterial Diseases, 8:19-25.

Office Action dated Mar. 4, 2021 for U.S. Appl. No. 16/936,900 (pp. 1-14).

Owen et al., 2013, "Mapping gene clusters within arrayed metagenomic libraries to expand the structural diversity of biomedically relevant natural products", Proc Nat Acad Sci USA, 110:11797-11802.

Owen et al., 2015, "Multiplexed metagenome mining using short DNA sequence tags facilitates targeted discovery of epoxyketone proteasome inhibitors", Proc Natl Acad Sci USA, 112:4221-4226.

Peek et al. "A Semisynthetic Kanglemycin Shows In Vivo Efficacy against High-Burden Rifampicin Resistant Pathogens", ACS Infect. Dis. 2020. vol. 6, pp. 2431-2440.

Peek et al. "Rifamycin Congeners Kanglemycins are Active Against Rifampicin-Resistant Bacteria via a Distinct Mechanism", Nature Communications. 2018. vol. 9:4147, 15 pages.

Perron et al., 2015, "Functional characterization of bacteria isolated from ancient arctic soil exposes diverse resistance mechanisms to modern antibiotics", PLoS One, 10:e0069533.

Price et al., 2010, "FastTree 2—Approximately Maximum-Likelihood Trees for Large Alignments", PLoS One, 5:e9490.

Pubchem Search for PCT/US21/34232, 2021.

Ramaswamy et al., 1998, "Molecular genetic basis of antimicrobial agent resistance in *Mycobacterium tuberculosis*", Tuber. Lung Dis., 79:3-29.

Rateb et al. 'Chaxamycins A-D, Bioactive Ansamycins from a Hyper-Arid Desert *Streptomyces* sp.', J. Nat. Prod., 2011,74 (6), pp. 1491-1499.

Reddy et al., 2012, "Natural product biosynthetic gene diversity in geographically distinct soil microbiomes", Appl Environ Microbiol, 78:3744-3752.

Roesch et al., 2007, "Pyrosequencing enumerates and contrasts soil microbial diversity", ISME J, 1:283-290.

Rothstein DM et al., 2008, "Rifalazil retains activity against rifampin-resistant mutants of Chlamydia pneumoniae", J. Antibiot. (Tokyo), 61:489-495.

Saito H et al., 1991, "In vitro antimycobacterial activities of newly synthesized benzoxazinorifamycins", Antimicrob. Agents Chemother., 35:542-547.

Sajduda et al., 2004, "Molecular characterization of rifampin- and isoniazid-resistant *Mycobacterium tuberculosis* strains isolated in Poland", J Clin Microbiol, 42:2425-2431.

Sensi P, 1983, "History of the development of rifampin", Rev. Infect. Dis., 5:Suppl 3, S402-S406.

Singhal et al., 2017, "Frequency of multi-drug resistance and mutations in *Mycobacterium tuberculosis* isolates from Punjab state of India", J Epidemiol Glob Health, 7:175-180.

Srivastava, A. et al., 2012, Frequency, spectrum, and nonzero fitness costs of resistance to myxopyronin in *Staphylococcus aureus*. Antimicrob. Agents Chemother. 56, 6250-6255.

Standards NCfCL. Methods for Dilution-Antimicrobial Susceptibility Tests for Bacteria That Grow Aerobically; M7-A7; Broth Microdilution Method: CLSI, Wayne, PA, USA, 2018.

Tadesse et al., 2016, "Drug resistance-conferring mutations in *Mycobacterium tuberculosis* from pulmonary tuberculosis patients in Southwest Ethiopia", Int J Mycobacteriol, 5:185-191.

Thibodeaux et al., 2008, "Natural-product sugar biosynthesis and enzymatic glycodiversification", Angew Chem Int Ed Engl, 47:9814-9859.

Thirumurugan et al., 2015, "Molecular analysis of rpoB gene mutations in rifampicin resistant *Mycobacterium tuberculosis* isolates by multiple allele specific polymerase chain reaction in Puducherry, South India", J Infect Public Health, 8:619-625.

(56) References Cited

OTHER PUBLICATIONS

Wang et al. "Isolation and Structure of a New Ansamycin Antibiotic Kanglemycin A from a Nocardia", The Journal of Antibiotics. 1988. vol. XLI, No. 2, pp. 264-267.

Wang et al., 2013, "PCR screening reveals considerable unexploited biosynthetic potential of ansamycins and a mysterious family of AHBA-containing natural products in actinomycetes", J Appl Microbiol, 115:77-85.

Wolff, Manfred E. "Burger's Medicinal Chemistry, 5ed, Part I", John Wiley & Sons, 1995, pp. 975-977. (Year: 1995).

Wood et al., 2007, "PCR screening reveals unexpected antibiotic biosynthetic potential in *Amycolatopsis* sp. strain UM16", J Appl Microbiol, 102:245-253.

Xia M et al., 2005, "Activities of rifamycin derivatives against wild-type and rpoB mutants of Chlamydia trachomatis", Antimicrob. Agents Chemother., 49:3974-3976.

Yamane T et al., 1993, "Synthesis and biological activity of 3'-hydroxy-5'-aminobenzoxazinorifamycin derivatives. Chem Pharm Bull (Tokyo)", Chem. Pharm. Bull. (Tokyo), 41:148-155.

Zhang et al., 2012, "BIGrat: a repeat resolver for pyrosequencing-based re-sequencing with Newbler", BMC Research Notes, 5:567.

Zhu et al., 2009, "Selective isolation and ansamycin-targeted screenings of commensal actinomycetes from the "maytansinoids-producing" arboreal Trewia nudiflora", Curr Microbiol, 58:87-94.

Zhu et al., 2010, "Ab initio gene identification in metagenomic sequences", Nucleic Acids Research, 38:e132.

Zumla et al., 2015, "The WHO 2014 global tuberculosis report-further to go", Lancet Glob Health, 3:e10-2.

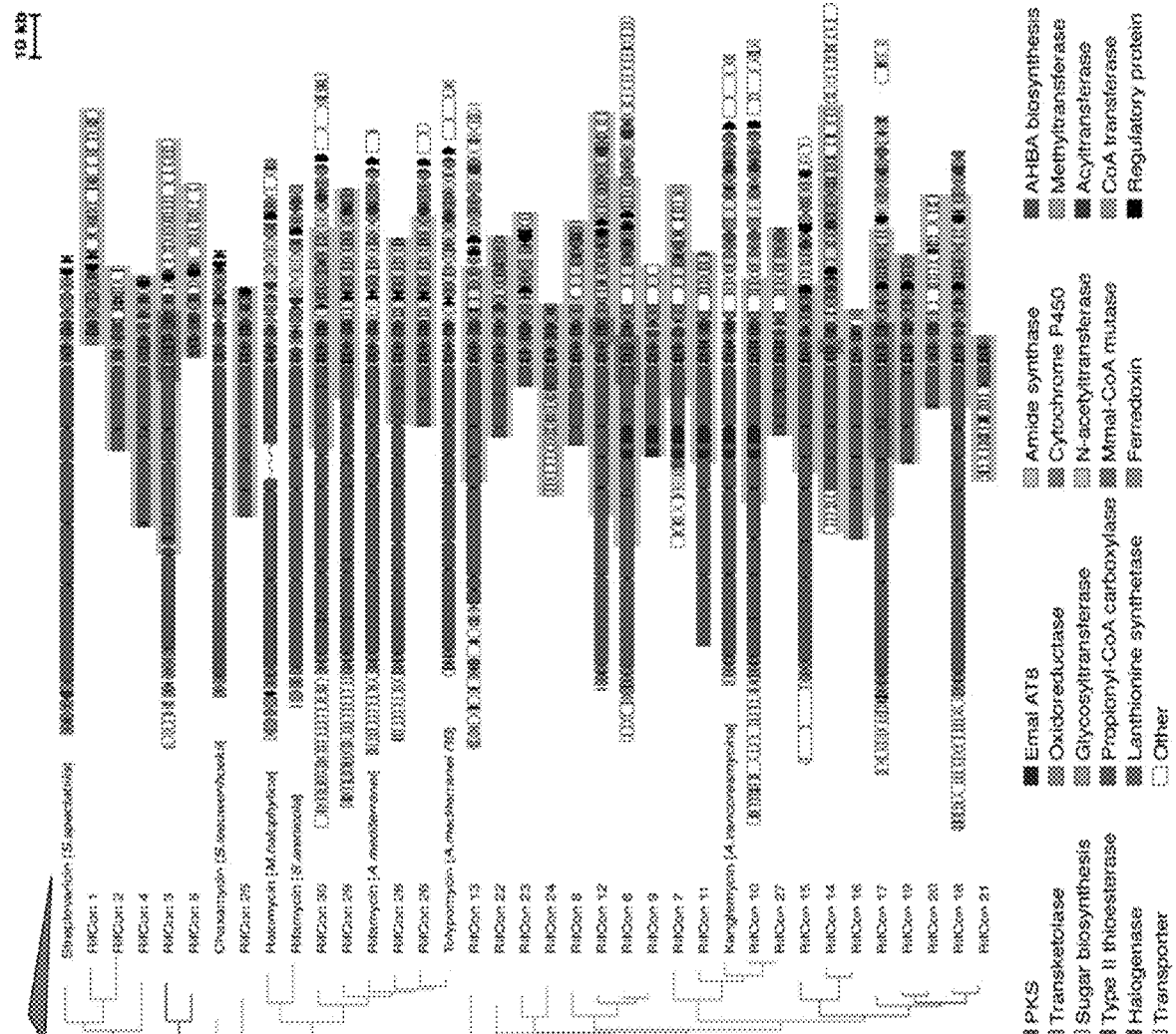
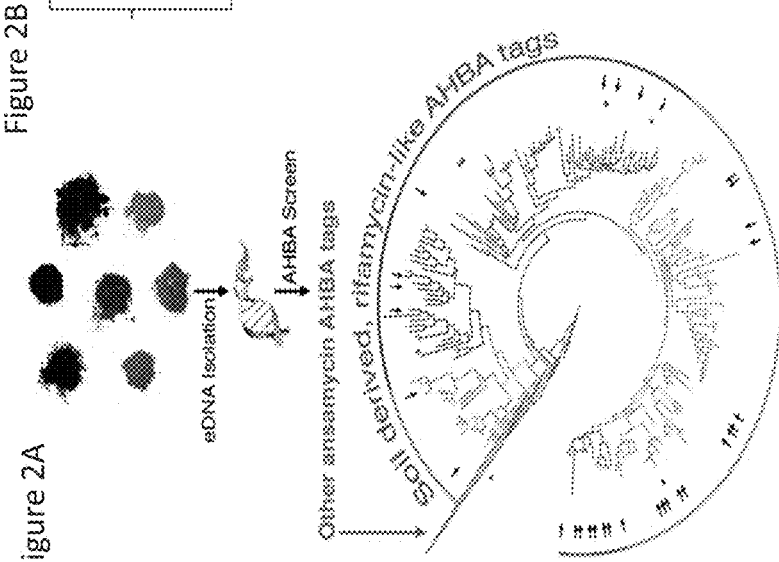
Figure 2A
Figure 2B

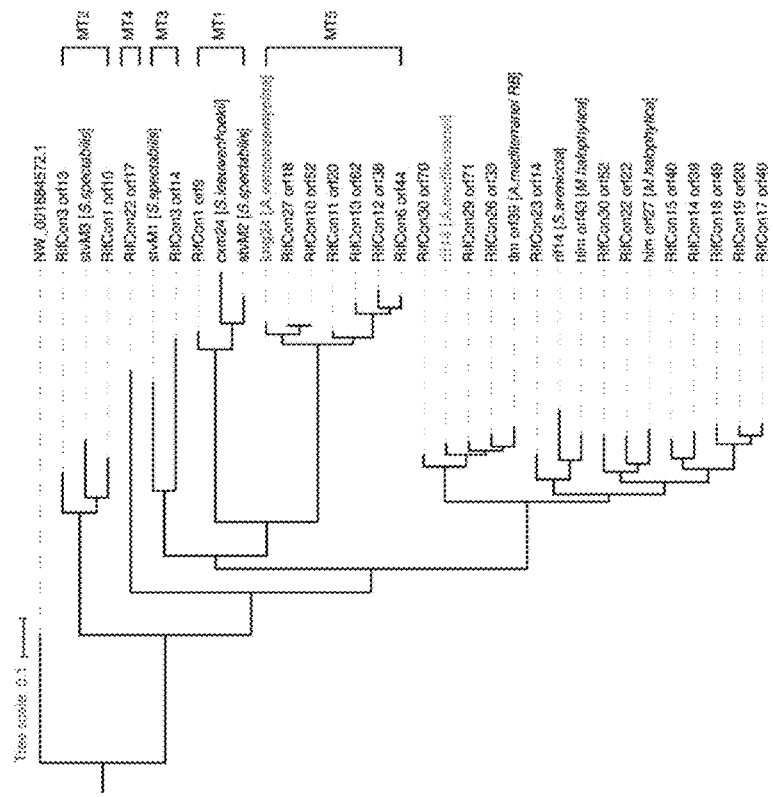
Figure 4C
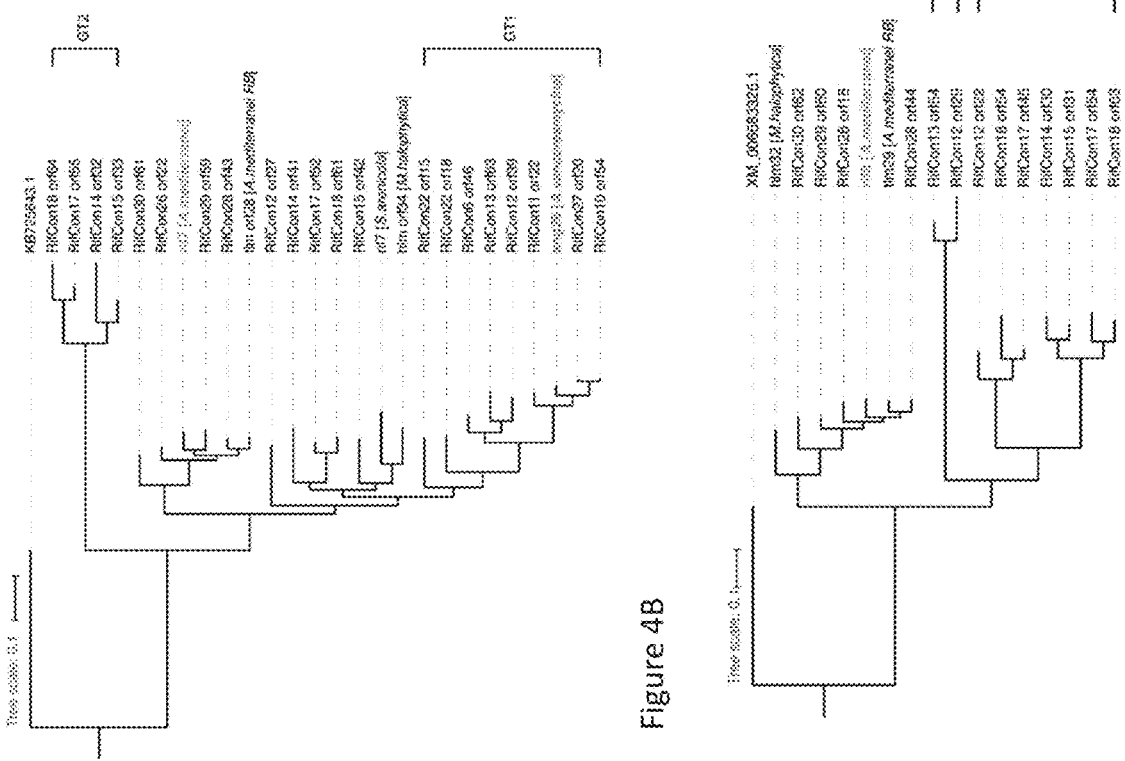
Figure 4A
Figure 4B

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Chemically synthesized

<400> SEQUENCE: 1
ccsgccttca ccttcatctc ctc                                            23

<210> SEQ ID NO 2
<211> LENGTH: 23
<212> TYPE: DNA
<213> ORGANISM: Artificial Sequence
```

<220> FEATURE:
<223> OTHER INFORMATION: Chemically synthesized

<400> SEQUENCE: 2
ayccggaaca tsgccatgta gtg                                          23

<210> SEQ ID NO 3
<211> LENGTH: 22
<212> TYPE: DNA
<213> ORGANISM: Artificial Sequence
<220> FEATURE:
<223> OTHER INFORMATION: Chemically synthesized

<400> SEQUENCE: 3
ctacacgacg ctcttccgat ct                                           22

<210> SEQ ID NO 4
<211> LENGTH: 22
<212> TYPE: DNA
<213> ORGANISM: Artificial Sequence
<220> FEATURE:
<223> OTHER INFORMATION: Chemically synthesized

<400> SEQUENCE: 4
cagacgtgtg ctcttccgat ct                                           22

<210> SEQ ID NO 5
<211> LENGTH: 18
<212> TYPE: DNA
<213> ORGANISM: Artificial Sequence
<220> FEATURE:
<223> OTHER INFORMATION: Chemically synthesized

<400> SEQUENCE: 5
atcgaggcsc aggcsytg                                                18

<210> SEQ ID NO 6
<211> LENGTH: 18
<212> TYPE: DNA
<213> ORGANISM: Artificial Sequence
<220> FEATURE:
<223> OTHER INFORMATION: Chemically synthesized

<400> SEQUENCE: 6
gaysasgtgs gcgttsgt                                                18

<210> SEQ ID NO 7
<211> LENGTH: 30
<212> TYPE: DNA
<213> ORGANISM: Artificial Sequence
<220> FEATURE:
<223> OTHER INFORMATION: Chemically synthesized

<400> SEQUENCE: 7
ccatctcatc cctgcgtgtc tccgactcag                                   30

<210> SEQ ID NO 8
<211> LENGTH: 23
<212> TYPE: DNA

```
<213> ORGANISM: Artificial Sequence
<220> FEATURE:
<223> OTHER INFORMATION: Chemically synthesized

<400> SEQUENCE: 8
cctctctatg ggcagtcggt gat                                           23

<210> SEQ ID NO 9
<211> LENGTH: 19
<212> TYPE: DNA
<213> ORGANISM: Artificial Sequence
<220> FEATURE:
<223> OTHER INFORMATION: Chemically synthesized

<400> SEQUENCE: 9
ccggttctay ctstccaag                                                19

<210> SEQ ID NO 10
<211> LENGTH: 19
<212> TYPE: DNA
<213> ORGANISM: Artificial Sequence
<220> FEATURE:
<223> OTHER INFORMATION: Chemically synthesized

<400> SEQUENCE: 10
aasraccacg asgagatgt                                                19
```

ANTIBACTERIAL COMPOUNDS, COMPOSITIONS THEREOF, AND METHODS USING SAME

CROSS-REFERENCE TO RELATED APPLICATIONS

This application is the U.S. national phase application filed under 35 U.S.C. § 371 claiming benefit to International Patent Application No. PCT/US2019/014877, filed Jan. 24, 2019, which is entitled to priority to U.S. Provisional Application No. 62/621,160, filed Jan. 24, 2018, which are incorporated by reference herein in their entireties.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file 046531-5012-00US_Sequence Listing_ST25.TXT, created on Sep. 28, 2020, 2,285 bytes, is hereby incorporated by reference.

BACKGROUND OF THE INVENTION

Semisynthetic derivatives of the bacterial natural product rifamycin (e.g., rifampicin) have historically been used in the treatment of tuberculosis and other gram-positive bacterial infections. As with many antibiotics, the clinical utility of these therapeutics has declined due to the increased incidence of antibiotic resistant bacterial pathogens. Resistance to rifamycin family antibiotics commonly occurs in clinical isolates as a result of point mutations in the antibiotic's target, DNA-dependent RNA polymerase (RNAP). These mutations are unlikely to be unique to clinical isolates as many, if not all, clinically relevant antibiotic resistance mechanisms are present in natural environments where they would have evolved in response to antibiotics produced by other bacteria. The search for biologically active bacterial natural products has frequently led to the discovery of structurally related antibiotics (congeners) that appear to arise from evolutionarily related biosynthetic gene clusters. While these close analogs typically have the same molecular target, they often exhibit differences in biological activity, including differences in potency, spectrum of activity and differences in activity against resistant bacteria.

There is a continuing need in the art for novel antimicrobial agents. The present disclosure addresses this unmet need in the art.

BRIEF DESCRIPTION

In some embodiments, the disclosure provides for compounds of formula (1):

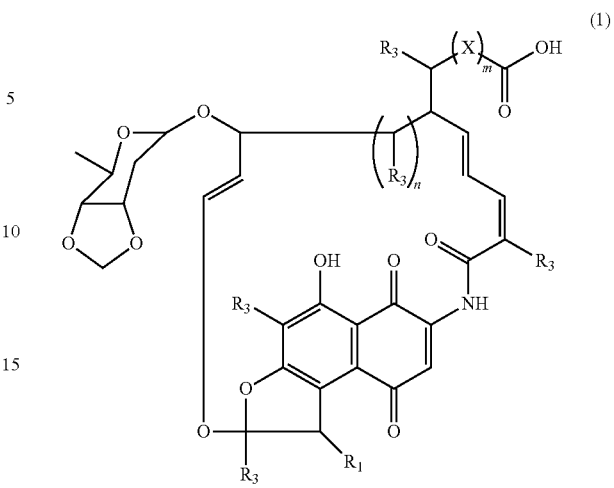

wherein $R_1$ is $CHR_4R_5$ or $OR_6$;

each occurrence of $R_4$ and $R_5$ independently represent a hydrogen atom, a halogen atom, alkyl, cycloalkyl, aryl, or heteroaryl;

$R_6$ is a hydrogen atom, alkyl, cycloalkyl, aryl, or heteroaryl;

each occurrence of $R_3$ independently represents a hydrogen atom, a halogen atom, alkyl, cycloalkyl, aryl, or heteroaryl, or $OR_7$;

$R_7$ represents a hydrogen atom, alkyl, cycloalkyl, aryl, heteroaryl, or $C(\!=\!O)R_8$;

$R_8$ represents alkyl, cycloalkyl, aryl, or heteroaryl; X represents —O—, —$NR_9$—, —$CR_9R_{10}$—, or —C(=O)—;

$R_9$ and $R_{10}$ each independently represent a hydrogen atom, a halogen atom, alkyl, cycloalkyl, aryl, or heteroaryl;

m represents an integer from 1 to 6; and n represents an integer from 4 to 10;

or a salt thereof.

In some embodiments, $R_1$ represents $OR_6$. In some embodiments, $R_1$ represents OH.

In some embodiments, each $R_3$ independently represents alkyl or $OR_7$. In some embodiments, each $R_7$ independently represents a hydrogen atom or $C(\!=\!O)R_8$. In some embodiments, $R_8$ is alkyl. In some embodiments, each $R_3$ is independently selected from the group consisting of —OH, methyl, and —OC(=O)$CH_3$.

In some embodiments, X represents —O—, —$CR_9R_{10}$—, or —C(=O)—. In some embodiments, each of $R_9$ and $R_{10}$ are a hydrogen atom. In some embodiments, each occurrence of X is selected from the group consisting of —O—, —C(=O)—, —$CH_2$—, and —$C(CH_3)_2$—.

In some embodiments, the compound of formula (1) has the following structure:

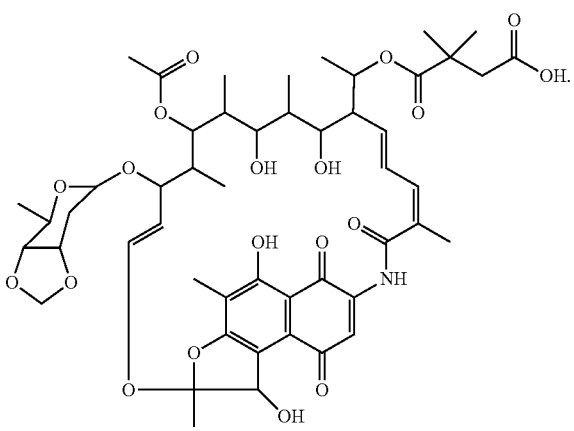 [SMILES: CC(=O)OC1C(C)C(OC2CC3OCOC3C(C)O2)/C=C/OC2(C)CC(O)c3c(c(C)c(O)c4c3C(=O)C=C(NC(=O)/C(C)=C\C=C\C(C(C)OC(=O)C(C)(C)CC(=O)O)C(O)C(C)C(O)C1C)C4=O)O2]

In some embodiments, the disclosure provides for compounds of formula (2):

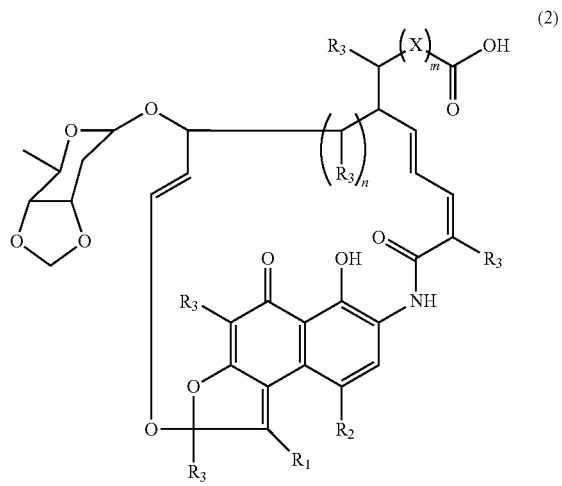

(2)

wherein:

$R_1$ and $R_2$ each independently represent $CHR_4R_5$, $CR_4R_5$, $OR_6$, or O, wherein $R_1$ and $R_2$ may optionally be joined to form a ring;

each occurrence of $R_4$ and $R_5$ independently represent a hydrogen atom, a halogen atom, alkyl, alkylene, cycloalkyl, aryl, or heteroaryl;

each occurrence of $R_6$ independently represent a hydrogen atom, alkyl, alkylene, cycloalkyl, aryl, or heteroaryl;

each occurrence of $R_3$ independently represents a hydrogen atom, a halogen atom, alkyl, cycloalkyl, aryl, or heteroaryl, or $OR_7$;

$R_7$ represents a hydrogen atom, alkyl, cycloalkyl, aryl, heteroaryl, or $C(=O)R_8$; $R_8$ represents alkyl, cycloalkyl, aryl, or heteroaryl;

X represents O, $NR_9$, $CR_9R_{10}$, or $C(=O)$;

$R_9$ and $R_{10}$ each independently represent a hydrogen atom, a halogen atom, alkyl, cycloalkyl, aryl, or heteroaryl;

m represents an integer from 1 to 6; and n represents an integer from 4 to 10;

or a salt thereof.

In some embodiments, $R_1$ and $R_2$ each independently represent $OR_6$. In some embodiments, $R_6$ independently represents a hydrogen atom or alkyl. In some embodiments, $R_1$ and $R_2$ each independently represent $OR_6$ and O, and $R_1$ and $R_2$ are joined to form a ring. In some embodiments, $R_6$ is alkylene. In some embodiments, $R_1$ represents $-OCH_2-$ and $R_2$ represents $-O-$, and $R_1$ and $R_2$ are joined to form a ring.

In some embodiments, each $R_3$ independently represents alkyl or $OR_7$. In some embodiments, each $R_7$ independently represents a hydrogen atom or $C(=O)R_8$. In some embodiments, $R_8$ is alkyl.

In some embodiments, each $R_3$ is independently selected from the group consisting of $-OH$, methyl, and $-OC(=O)CH_3$.

In some embodiments, X represents $-O-$, $-CR_9R_{10}-$, or $-C(=O)-$. In some embodiments, each of $R_9$ and $R_{10}$ are a hydrogen atom. In some embodiments, each occurrence of X is selected from the group consisting of $-O-$, $-C(=O)-$, $-CH_2-$, and $-C(CH_3)_2-$.

In some embodiments, the compound of formula (2) has the following structure:

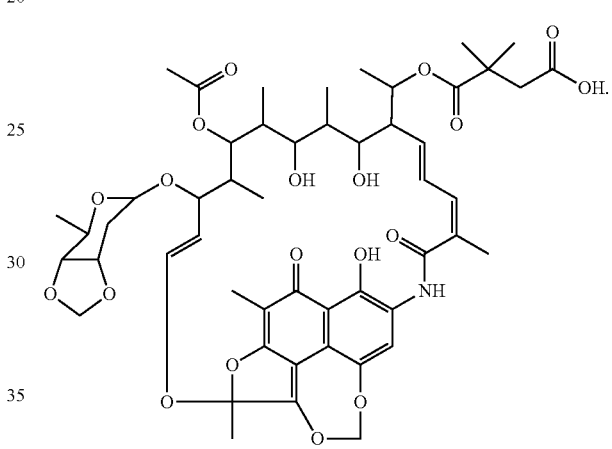

In some embodiments, the compounds of formula (1) and (2) are substantially pure. In some embodiments, the compounds of formula (1) and (2) are enantiomerically pure.

In some embodiments, the compounds of formula (1) and (2) have a lower MIC (μg/mL) against rifamycin-resistant bacteria than rifamycin.

In some embodiments, the disclosure provides for pharmaceutical compositions comprising a therapeutically effective amount of one or more compounds of formula (1) or (2) and a pharmaceutically acceptable excipient. In some embodiments, the pharmaceutical composition further comprises a pharmaceutical carrier.

In some embodiments, the present disclosure provides for a method of preventing or reducing the growth or proliferation of a microorganism, wherein the method comprises contacting the microorganism with a composition comprising a compound of formula (1) or (2). In some embodiments, the microorganism is a bacterium. In some embodiments, the bacterium is resistant to at least on antibiotic. In some embodiments, the bacterium is resistant to rifamycin. In some embodiments, the bacterium has at least one point mutation that confers antibiotic resistance. In some embodiments, the bacterium has one or more of the following mutations of one or more amino acids: (1) serine to leucine; (2) histidine to tyrosine; (3) or asparagine to tyrosine. In some embodiments, the method further comprises administering to the subject an additional therapeutic agent.

In some embodiments, the present disclosure provides for methods of treating or preventing a bacterial infection in a subject, wherein the method comprises administering to the subject a composition comprising a compound of formula (1) or (2). In some embodiments, the bacterial infection is an infection of Staphylococcus aureus, Staphylococcus epidermidis, Listeria monocytogenes and M. tuberculosis. In some embodiments, the bacterial infection is resistant to rifamycin. In some embodiments, the bacterial infection is caused by a bacterium that has at least one point mutation that confers antibiotic resistance. In some embodiments, the bacterium has one or more of the following mutations of one or more amino acids: (1) serine to leucine; (2) histidine to tyrosine; (3) or asparagine to tyrosine. In some embodiments, the method further comprises administering to the subject an additional therapeutic agent.

In some embodiments, the present disclosure provides for compounds of formula (1) and (2) for use in treating a bacterial infection. In some embodiments, the bacterial infection is an infection of Staphylococcus aureus, Staphylococcus epidermidis, Listeria monocytogenes and M. tuberculosis. In some embodiments, the bacterial infection is resistant to rifamycin. In some embodiments, the bacterial infection is caused by a bacterium that has at least one point mutation that confers antibiotic resistance. In some embodiments, the bacterium has one or more of the following mutations of one or more amino acids: (1) serine to leucine; (2) histidine to tyrosine; (3) or asparagine to tyrosine.

BRIEF DESCRIPTION OF THE DRAWINGS

The following detailed description of preferred embodiments of the disclosure will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities of the embodiments shown in the drawings.

FIG. 2, comprising FIG. 2A and FIG. 2B, depicts the sequence-based screen of soils for rifamycin congener biosynthetic gene clusters. FIG. 2A depicts a screening overview. DNA isolated from approximately 1,500 soils was screened for the presence of AHBA synthase genes by PCR using degenerate primers. Sequences generated in this screen were used to construct a phylogenetic tree, onto which AHBA synthase reference sequences from known rifamycin congener gene clusters were mapped (marked with asterisks). Metagenomic DNA cosmid libraries were generated from soils that contained AHBA sequences that spanned all AHBA clades predicted to be associated with rifamycin congener gene clusters. Primary clones (those containing an AHBA synthase gene) were recovered from the libraries by a PCR dilution method using degenerate AHBA synthase primers. The same approach, but with degenerate primers targeting PKS ketosynthase domains and the rif15A/15B tailoring genes, was used to recover regions of the pathways that flank those found on the primary clone. AHBA sequences corresponding with primary clones that were targeted for recovery are indicated with arrows on the phylogenetic tree. FIG. 2B depicts a summary of rifamycin congener gene clusters recovered from the soil metagenomes. Gray boxes mark the primary AHBA clones that were initially recovered.

FIG. 4, comprising FIG. 4A-FIG. 4C depicts tailoring genes that are predicted to encode enzymes that are phylogenetically distinct from those found in known rifamycin-like gene clusters. FIG. 4A depicts a phylogenetic analysis of eDNA-derived glycosyltransferase genes. Genes from previously characterized rifamycin family gene clusters are shown for reference. Clades that lack an obvious homolog from the A. mediterranei rifamycin gene cluster are labeled. These labels correspond with the table shown in FIG. 3. FIG. 4B depicts a phylogenetic analysis of eDNA derived methyltransferase genes. Genes from previously characterized rifamycin family gene clusters are shown for reference. Clades that lack an obvious homolog from the A. mediterranei rifamycin gene cluster are labeled. These labels correspond with the table shown in FIG. 3. FIG. 4C depicts a phylogenetic analysis of sugar epimerase genes. Genes from previously characterized rifamycin family gene clusters are shown for reference. Clades that lack an obvious homolog from the A. mediterranei rifamycin gene cluster are labeled. These labels correspond with the table shown in FIG. 3.

FIG. 5, comprising FIG. 5A depicts a phylogenetic analysis of eDNA-derived cytochrome P450 genes. Genes from previously characterized rifamycin family gene clusters are shown for reference. Clades that lack an obvious homolog from the A. mediterranei rifamycin gene cluster are labeled. These labels correspond with the table shown in FIG. 3. FIG. 5B depicts a phylogenetic analysis of eDNA-derived oxidoreductase genes. Genes from previously characterized rifamycin family gene clusters are shown for reference. Clades that lack an obvious homolog from the A. mediterranei rifamycin gene cluster are labeled. These labels correspond with the table shown in FIG. 3.

FIG. 6, comprising FIG. 6A depicts a comparison of the rifamycin and kanglemycin (kng) gene clusters. Lines connecting the two clusters indicate genes that are predicted to be functionally equivalent. For simplicity, only genes lacking a counterpart in the rifamycin cluster are label in the kanglemycin cluster. Colored boxes surrounding these genes correspond to the substructures they are predicted to encode (shown in panel C). FIG. 6B depicts structures of kanglemycins A, V1 and V2. FIG. 6C depicts a summary of the proposed biosynthesis of kanglemycin V2. Different structural features are colored as follow: red, polyketide core; blue, Emal modification; green, AHBA-derived substructure; black, tailoring modifications. The PKS module eight dehydratase (DH*) domain, which is predicted to be inactive, is marked with an asterisk to differentiate it from the remaining, active domains. FIG. 6D depicts in vivo activity profiles of the kanglemycins against rifampicin (Rif) resistant S. aureus. A structural model (PDB code 5UHD) shows the interaction between rifampicin and the three most commonly mutated residues in rifampicin resistant M. tuberculosis clinical isolates. FIG. 6E depicts in vitro transcription assay with radiolabeled nucleotides showing the activity of rifampicin and the kanglemycins at the concentrations indicated against wild-type RNA polymerase (RNAP) from M. smegmatis and an S447L mutant variant. Full-length (F) and abortive (A) transcripts are shown.

FIG. 7, comprising FIG. 7A depicts an HPLC chromatogram of partially purified extracts from A. vancoresmycina cultures. Crude ethyl acetate extracts from A. vancoresmycina cultures were first fractionated by flash chromatography. Fractions with strong UV absorbance at 254 nm and 420 nm were then pooled and subjected to HPLC. Peaks corresponding to kanglemycins A, V1, and V2 are labeled. FIG. 7B depicts a kanglemycin A UV spectrum. FIG. 7C depicts a kanglemycin V1 UV spectrum. FIG. 7D depicts a kanglemycin V2 UV spectrum.

FIG. 11, comprising FIG. 11A depicts phylogenetic analysis of sugar ketoreductase genes. Genes from previously characterized rifamycin family gene clusters are shown for reference. Clades that lack an obvious homolog from the A. mediterranei rifamycin gene cluster are labeled. These labels correspond with the table shown in FIG. 3. FIG. 11B depicts phylogenetic analysis of sugar dehydratase genes. Genes from previously characterized rifamycin family gene clusters are shown for reference. Clades that lack an obvious homolog from the A. mediterranei rifamycin gene cluster are labeled. These labels correspond with the table shown in FIG. 3.

FIG. 13, comprising FIG. 13A depicts the $^1H$ NMR spectrum of kanglemycin A in $CD_2Cl_2$, collected at 25° C. FIG. 13B depicts the $^{13}C$ NMR spectrum of kanglemycin A in $CD_2Cl_2$, collected at 25° C.

FIG. 14, comprising FIG. 14A depicts an HMQC NMR spectrum of kanglemycin A in $CD_2Cl_2$, collected at 25° C. FIG. 14B depicts a COSY NMR spectrum of kanglemycin A in $CD_2Cl_2$, collected at 25° C.

FIG. 16, comprising FIG. 16A depicts an $^1H$ NMR spectrum of kanglemycin V1 in MeOD, collected at 25° C. FIG. 16B depicts a $^{13}C$ NMR spectrum of kanglemycin V1 in MeOD, collected at 25° C.

FIG. 17, comprising FIG. 17A depicts an HSQC NMR spectrum of kanglemycin V1 in MeOD, collected at 25° C. FIG. 17B depicts a COSY NMR spectrum of kanglemycin V1 in MeOD, collected at 25° C.

FIG. 25A depicts the proposed biosynthesis of ethylmalonyl-CoA. FIG. 25B depicts the proposed biosynthesis of 2,2-dimethylsuccinyl-CoA. FIG. 25C depicts the proposed biosynthesis of NDP-methylene digitoxose. The enzyme(s) responsible for the production of 2,2-dimethylsuccinyl-CoA from succinyl-CoA are not bioinformatically obvious. Reactions predicted to be catalyzed by enzymes encoded by the kng gene cluster are indicated. All other reactions are predicted to be catalyzed by enzymes encoded outside of the kng gene cluster.

DETAILED DESCRIPTION

Figure 1:
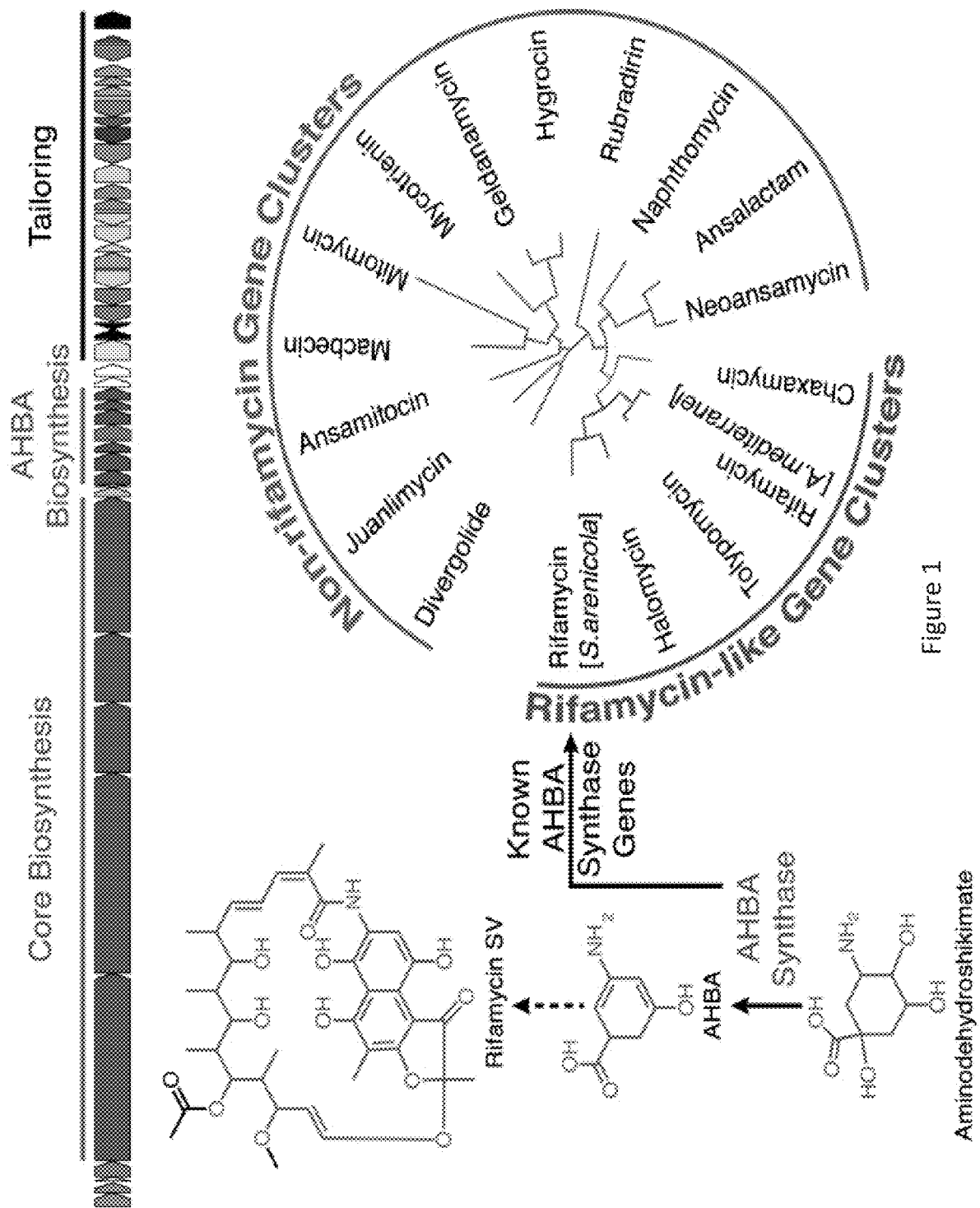
FIG. 1 depicts the organization of a prototypical rifamycin biosynthetic gene cluster and AHBA synthase phylogeny. The rifamycin gene cluster from Amycolatopsis mediterranei is shown. The AHBA synthase gene is outlined in red. The reaction catalyzed by AHBA synthase and the structure of rifamycin SV (the product of the gene cluster) are shown. The rifamycin SV structure is colored according to the genes responsible for producing its polyketide core (red), AHBA-derived moiety (green) and tailoring functionalities (black). The phylogenetic divergence of AHBA synthase genes from previously characterized gene clusters correlates with the different structural classes of ansamycins.

The present disclosure provides novel compounds that are useful as antibacterial agents. In one embodiment, the compounds are rifamycin congers. In one embodiment, the compounds exhibit antibacterial activity against strains resistant to antibacterial compounds, such as rifamycin. Thus, the present disclosure provides novel compounds, compositions comprising at least one compound of the disclosure, methods of making the compounds of the disclosure, and methods of using the compounds of the disclosure.

In one aspect, the disclosure provides methods of treating a bacterial infection in a subject comprising administering a composition comprising a compound of the disclosure. The present disclosure also provides methods of preventing or reducing the growth or proliferation of microorganisms by contacting the microorganism with a composition comprising a compound of the disclosure.

Another aspect of the present disclosure provides a method of overcoming antibacterial resistance. For example, in one embodiment, the method comprises introducing a methylenedioxy group into an antibacterial compound.

Definitions

Unless defined otherwise, all technical and scientific terms used herein have the same meaning as commonly understood by one of ordinary skill in the art to which this disclosure belongs. Although any methods, materials and components similar or equivalent to those described herein can be used in the practice or testing of the present disclosure, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element. As such, the terms "a" (or "an"), "one or more" and "at least one" are used interchangeably herein. In addition, reference to "a compound" by the indefinite article "a" or "an" does not exclude the possibility that more than one of the compounds is present, unless the context clearly requires that there is one and only one of the inhibitors.

"About" and/or "approximately" as used herein when referring to a measurable value, for example numerical values and/or ranges, such as an amount, a temporal duration, and the like, is meant to encompass variations of 20%, +10%, +5%, +1%, or 0.1% from the specified value, as such variations are appropriate. For example, "about 40 [units]" may mean within 25% of 40 (e.g., from 30 to 50), within 20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein, and all values within a given range may be an endpoint for the range encompassed thereby. Thus, the range "from 50 to 80" includes all possible ranges therein (e.g., 51-79, 52-78, 53-77, 54-76, 55-75, 60-70, etc.), as if each value and subrange were expressly disclosed. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This definition applies regardless of the breadth of the range.

"Amino" refers to the —$NH_2$ group.
"Cyano" refers to the —CN group.
"Hydroxy" or "hydroxyl" refers to the —OH group.
"Imino" refers to the =NH group.
"Nitro" refers to the —$NO_2$ group.
"Oxo" refers to the =O group.
"Thioxo" refers to the =S group.

As used herein, the term "alkyl," or "alkyl group" by itself or as part of another substituent means, unless otherwise stated, a straight or branched chain hydrocarbon having from 1 to 12 carbon atoms. In some embodiments, the alkyl is a $C_1$-$C_{12}$ alkyl, a $C_1$-$C_{10}$ alkyl, a $C_1$-$C_8$ alkyl, a $C_1$-$C_6$ alkyl, a $C_1$-$C_4$ alkyl, or a $C_1$-$C_3$ alkyl. For example, an alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples include methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl, n-undecyl, n-dodecyl, and cyclopropylmethyl. Unless stated otherwise specifically in the specification, an alkyl group can be optionally substituted.

"Alkylene" or "alkylene chain" refers to a fully saturated, straight or branched divalent hydrocarbon, and having from one to twelve carbon atoms, and which has two points of attachment to the rest of the molecule. In some embodiments, the alkylene is a $C_1$-$C_{12}$ alkylene, a $C_1$-$C_{10}$ alkylene, a $C_1$-$C_8$ alkylene, a $C_1$-$C_6$ alkylene, a $C_1$-$C_4$ alkylene, or a $C_1$-$C_3$ alkylene. Non-limiting examples of $C_1$-$C_{12}$ alkylene include methylene, ethylene, propylene, n-butylene, ethenylene, propenylene, n-butenylene, propynylene, n-butynylene, and the like. The points of attachment of the alkylene chain to the rest of the molecule can be through one carbon or any two carbons within the chain. Unless stated otherwise specifically in the specification, an alkylene chain can be optionally substituted.

"Alkenyl" or "alkenyl group" refers to a straight or branched hydrocarbon chain having from two to twelve carbon atoms, and having one or more carbon-carbon double bonds. Each alkenyl group is attached to the rest of the molecule by a single bond. Alkenyl group comprising any number of carbon atoms from 2 to 12 are included. In some embodiments, the alkenyl is a $C_2$-$C_{12}$ alkenyl, a $C_2$-$C_{10}$ alkenyl, a $C_2$-$C_5$ alkenyl, a $C_2$-$C_6$ alkenyl, a $C_2$-$C_4$ alkenyl, or a $C_2$-$C_3$ alkenyl. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. In some embodiments, the alkynyl is a $C_2$-$C_{12}$ alkynyl, a $C_2$-$C_{10}$ alkynyl, a $C_2$-$C_8$ alkynyl, a $C_2$-$C_6$ alkynyl, a $C_2$-$C_4$ alkynyl, or a $C_2$-$C_3$ alkynyl. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

As used herein, the term "heteroalkyl" by itself or in combination with another term means, unless otherwise stated, a stable straight or branched chain alkyl group consisting of from 1 to 12 carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—C $H_3$, and —$CH_2CH_2$—S (=O)—$CH_3$. Up to two heteroatoms may be consecutive, such as, for example, —$CH_2$—NH—$OCH_3$, or —$CH_2$—$CH_2$—S—S—$CH_3$. Unless stated otherwise specifically in the specification, an heteroalkyl group can be optionally substituted.

As used herein, the term "alkoxy" employed alone or in combination with other terms means, unless otherwise stated, refers to a group of the formula —$OR_a$ where $R_a$ is an alkyl, alkenyl or alknyl group having from 1 to 12 carbon atoms, as defined above, connected to the rest of the molecule via an oxygen atom, such as, for example, methoxy, ethoxy, 1-propoxy, 2-propoxy (isopropoxy) and the higher homologs and isomers. Unless stated otherwise specifically in the specification, an alkoxy group can be optionally substituted.

"Alkylamino" refers to a group of the formula —$NHR_a$ or —$NR_aR_a$ where each $R_a$ is, independently, an alkyl, alkenyl or alkynyl group as defined above containing one to twelve carbon atoms. Unless stated otherwise specifically in the specification, an alkylamino group can be optionally substituted.

"Alkylcarbonyl" refers to the —C(=O)$R_a$ moiety, wherein $R_a$ is an alkyl, alkenyl or alkynyl group as defined above. A non-limiting example of an alkyl carbonyl is the methyl carbonyl ("acetal") moiety. Alkylcarbonyl groups can also be referred to as "$C_w$-$C_z$ acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_1$-$C_{10}$ alkenyl, or $C_1$-$C_{10}$ alkynyl group as defined above. Unless stated otherwise specifically in the specification, an alkyl carbonyl group can be optionally substituted.

As used herein, the term "halo" or "halogen" alone or as part of another substituent means, unless otherwise stated, a fluorine, chlorine, bromine, or iodine group.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group can be optionally substituted.

As used herein, the term "cycloalkyl" refers to a stable mono cyclic or polycyclic non-aromatic group, wherein each of the atoms forming the ring (i.e. skeletal atoms) is a carbon atom, which can include fused or bridged ring systems, having from three to twenty carbon atoms (e.g., having from three to ten carbon atoms) and which is attached to the rest of the molecule by a single bond. In one embodiment, the cycloalkyl group is saturated or partially unsaturated. In another embodiment, the cycloalkyl group is fused with an aromatic ring. Cycloalkyl groups include groups having from 3 to 20 carbon ring atoms. Illustrative examples of cycloalkyl groups include, but are not limited to, the following moieties.

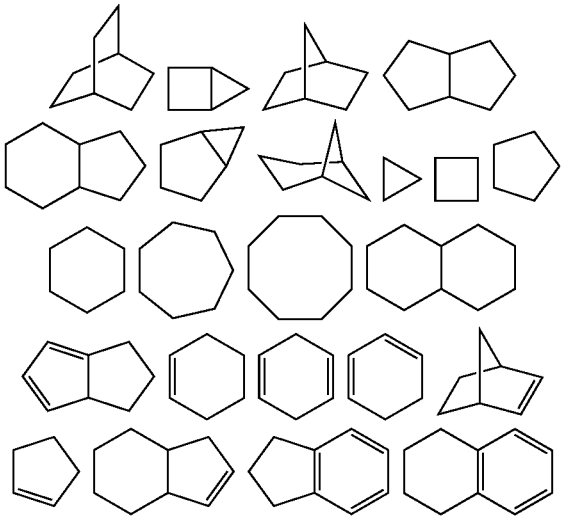

wherein any hydrogen atom in the above groups may be replaced by a bond to the molecule.

Monocyclic cycloalkyls include, but are not limited to, cyclopropyl, cyclobutyl, cyclopentyl, cyclohexyl, cycloheptyl, and cyclooctyl. Dicyclic or polycyclic cycloalkyls include, but are not limited to, tetrahydronaphthyl, indanyl, and tetrahydropentalenyl, adamantyl and norbornyl. The term cycloalkyl includes "unsaturated nonaromatic carbocyclyl," "carbocyclyl," "carbocyclic ring," "carbocycle," or "nonaromatic unsaturated carbocyclyl" groups, both of which refer to a nonaromatic carbocycle as defined herein, which contains at least one carbon double bond or one carbon triple bond.

"Cycloalkenyl" refers to a stable non aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyls include, for example, cyclopentenyl, cyclohexenyl, cycloheptenyl, cyclooctenyl, and the like. Polycyclic cycloalkenyls include, for example, bicyclo[2.2.1]hept-2-enyl and the like. Unless otherwise stated specifically in the specification, a cycloalkenyl group can be optionally substituted.

"Cycloalkynyl" refers to a stable non aromatic monocyclic or polycyclic hydrocarbon consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyls include, for example, cycloheptynyl, cyclooctynyl, and the like. Unless otherwise stated specifically in the specification, a cycloalkynyl group can be optionally substituted.

The terms "heterocyclic ring", "heterocycle" and "heterocyclyl" are used interchangeably herein to refer to a 3- to 20-membered containing one to six heteroatoms each independently selected from the group consisting of O, S and N. In one embodiment, each heterocyclyl group has from 4- to 10-atoms in its ring system, and from one to three heteroatoms each independently selected from the group consisting of O, S and N. Unless stated otherwise specifically in the specification, the heterocyclyl can be a monocyclic, bicyclic, tricyclic or tetracyclic ring system, which can include fused or bridged ring systems. In one embodiment, the nitrogen, carbon, or sulfur heteroatoms may be optionally oxidized, and the nitrogen atom may be optionally quaternized. The heterocyclic system may be attached, unless otherwise stated, at any heteroatom or carbon atom that affords a stable structure. The heterocyclyl can be partially or fully saturated. A heterocycle may be aromatic or non-aromatic in nature, and, in instances in which the heterocyclyl is polycyclic, the polycyclic ring may be aromatic, non-aromatic, or contain both aromatic and non-aromatic rings. In one embodiment, the heterocycle is a heteroaryl. Unless stated otherwise specifically in the specification, a heterocyclyl group can be optionally substituted.

Examples of such heterocyclyls include, but are not limited to, aziridinyl, azetidinyl, beta lactamyl, dioxolanyl, oxazolidinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrrolinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxothiomorpholinyl, oxiranyl, thiiranyl, oxetanyl, thietanyl, sulfolanyl, 2,3-dihydrofuranyl, 2,5-dihydrofuranyl, thiophanyl, 1,2,3,6-tetrahydropyridinyl, 1,4-dihydropyridinyl, piperazinyl, thiomorpholinyl, pyranyl, 2,3-dihydropyranyl, tetrahydropyranyl, 1,4-dioxanyl, 1,3-dioxanyl, homopiperazinyl, homopiperidinyl, 1,3-dioxepanyl, 4,7-dihydro-1,3-dioxepinyl, and hexamethyleneoxidyl.

Other non-limiting examples of heterocyclyl groups are:

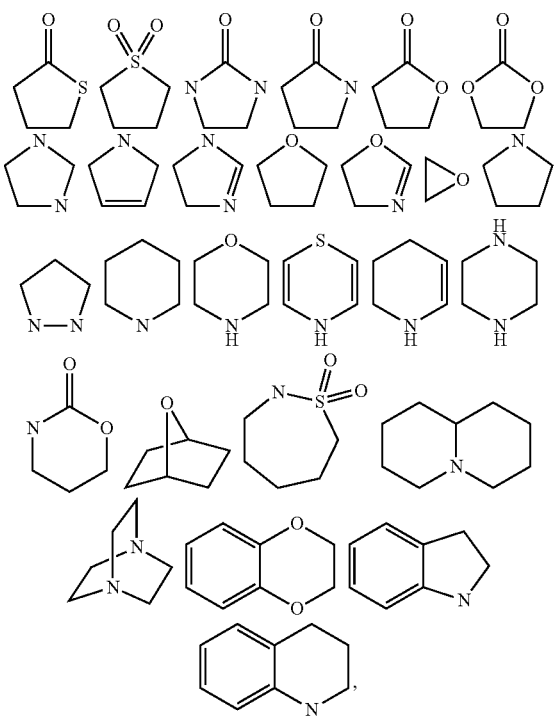

wherein any hydrogen atom in the above groups may be replaced by a bond to the molecule.

As used herein, the term "aromatic" refers to a carbocyclyl or heterocyclyl with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a hydrocarbon ring system, comprising hydrogen, 6 to 18 carbon atoms and at least one aromatic ring. For purposes of this disclosure, the aryl can be a monocyclic, bicyclic, tricyclic or tetracyclic ring system, which can include fused or bridged ring systems. For example, aryls include, but are not limited to, a biphenyl, or may be fused, such as naphthalene. Examples of aryl groups include benzyl, indacenyl, pyrenyl, tiphenyl, phenyl, anthracyl, and naphthyl. Unless stated otherwise specifically in the specification, the term "aryl" is meant to include aryl groups that are optionally substituted.

As used herein, the term "heteroaryl" or "heteroaromatic" refers to a 5 to 20 membered ring system comprising hydrogen atoms, one to thirteen carbon atoms, one to six heteroatoms selected from the group consisting of nitrogen, oxygen and sulfur, and at least one aromatic ring. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. A polycyclic heteroaryl may include one or more rings that are partially saturated. Examples include the following moieties:

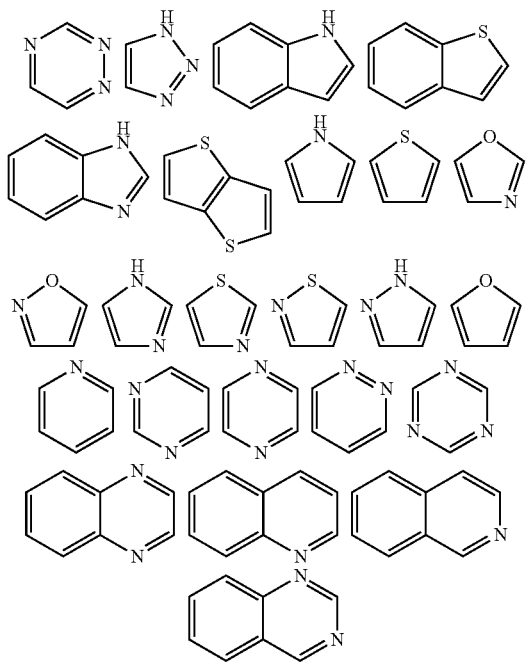

wherein any hydrogen atom in the above groups may be replaced by a bond to the molecule.

Examples of heteroaryl groups include, but are not limited to, pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl, 1,3,4-oxadiazolyl, indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl. Unless stated otherwise specifically in the specification, a heteroaryl group can be optionally substituted.

"Thioalkyl" refers to a formula —$SR_a$ where $R_a$ is an alkyl, alkenyl, or alkynyl as defined above containing one to twelve carbon atoms. Unless stated otherwise specifically in the specification, a thioalkyl group can be optionally substituted.

As used herein, the term "substituted" means any of the above groups (i.e., alkyl, alkylene, alkenyl, alkynyl, alkoxy, aryl, carbocyclyl, cycloalkyl, cycloalkenyl, cycloalkynyl, heterocyclyl, and/or heteroaryl) wherein at least hydrogen atom is replaced by a bond to a non-hydrogen atom or group of atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with, for example, —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with, for example, —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently selected from any of the above groups, including but not limited to: hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to any of the above groups, including but not limited to amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

As used herein, the term "antimicrobial" refers to an ability to kill or inhibit the growth of microorganisms, including but not limited to bacteria, viruses, yeast, fungi, and protozoa, or to attenuate the severity of a microbial infection. The antimicrobial compounds or compositions of the present disclosure are compounds or compositions that may be used for cleaning or sterilization, or may be used in the treatment of disease and infection. The applications may include both in vitro and in vivo antimicrobial uses. "Applying" an antimicrobial composition may include administrating a composition into a human or animal subject.

As used herein, the term "contacting" includes, but is not limited to, impregnating, compounding, mixing, integrating, coating, rubbing, painting, spraying, immersing, rolling, smearing and dipping.

As used herein, the term "treatment" or "treating," is defined as one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition. In one embodiment "treatment" or "treating," is defined as the application or administration of a therapeutic agent, i.e., a compound useful within the disclosure (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of medicine or pharmacology. In one embodiment, the condition is selected from the group consisting of a bacterial infection, fungal infection, mycobacterial infection, viral infection, and a combination thereof.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the term "pharmaceutical composition" refers to a mixture of at least one compound useful within the disclosure with a pharmaceutically acceptable carrier. The pharmaceutical composition facilitates administration of the compound to a patient or subject, or use of the compound within the methods of the disclosure. Multiple techniques of administering a compound exist in the art including, but not limited to, intravenous, oral, aerosol, parenteral, ophthalmic, pulmonary and topical administration.

As used herein, the terms "effective amount," "pharmaceutically effective amount" and "therapeutically effective amount" refer to a non-toxic but sufficient amount of an agent and/or formulation according to the disclosure that when administered to a patient for treating a state, disorder or condition is sufficient to provide the desired biological and/or clinical result. That result may be reduction and/or alleviation of the signs, symptoms, or causes of a disease, or any other desired alteration of a biological system. An appropriate therapeutic amount in any individual case may be determined by one of ordinary skill in the art using routine experimentation. The "effective amount" will vary depending on the active ingredient, the state, disorder, or condition to be treated and its severity, and the age, weight, physical condition and responsiveness of the mammal to be treated.

All weight percentages (i.e., "% by weight" and "wt. %" and "w/w") referenced herein, unless otherwise indicated, are measured relative to the total weight of the pharmaceutical composition.

As used herein, the term "potency" refers to the dose needed to produce half the maximal response ($ED_{50}$).

As used herein, the term "efficacy" refers to the maximal effect ($E_{max}$) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" embraces addition salts of free acids or free bases. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the disclosure include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the patient. Supplementary active compounds may also be incorporated into the compositions. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, Pa.), which is incorporated herein by reference.

As used herein, the term "minimum inhibitory concentration (MIC)" refers to the lowest concentration of an antimicrobial agent that will inhibit the visible growth of a microorganism after overnight incubation. MIC values against bacteria may be determined by standard methods. See also P. A. Wayne, Methods for Dilution Antimicrobial Tests for Bacteria that Grow Aerobically; Approved Standard, Ninth Edition, 2012, CLSI Document M07-A9, Vol. 32 No. 2, which is incorporated by reference herein in its entirety.

As used herein, the term "organic solvent" refers to solvents including, but not limited to, alcohols (e.g., methanol and ethanol), ketones (e.g., acetone and methylethylketone), ethers (e.g., tetrahydrofuran), aldehydes (e.g., formaldehyde), acetonitrile, carboxylic acids (e.g., formic acid and acetic acid), methylene chloride, chloroform, alkyl carbonates, and hydrocarbons (e.g., hexane and heptane, and xylene), esters (e.g., ethyl acetate, propyl acetate, butyl acetate, amyl acetate, and combination thereof) or similar solvents.

As used herein, the term "alkalinizing agent" refers to an organic and inorganic base, including sodium hydroxide, potassium hydroxide, alkyl hydroxides, ammonia in water (27% ammonium hydroxide), diethylamine and triethylamine.

As used herein, the term "high ionic strength salt" refers to a salt exhibiting high ionic strength, such as sodium chloride, potassium chloride, or ammonium acetate. These salts may act both as an alkalinizing agent and as a penetrating agent to enhance the reactivity of the surface. Therefore, in one specific embodiment, high ionic strength salts may also be used in the step of forming the biofilm-penetrating composition.

The following description includes information that may be useful in understanding the present disclosure. It is not an admission that any of the information provided herein is prior art or relevant to the presently claimed inventions, or that any publication specifically or implicitly referenced is prior art.

DESCRIPTION

The present disclosure is based, in part on the discovery of novel antibacterial compounds and the discovery that these compounds show potent activity against the most common RNA polymerase point mutations that are known to confer antibacterial resistance in clinical isolates of pathogenic bacteria (*Nature Communications* (2018) 9, 4147, which is incorporated by reference herein in its entirety). For example, a few common point mutations result in one or more of the following amino acid mutations: (1) serine to leucine; (2) histidine to tyrosine; (3) or asparagine to tyrosine. Other examples are known in the art, e.g., J Antibiot (Tokyo). 2014 September; 67(9):625-30. doi: 10.1038/ja.2014.107. Epub 2014 Aug. 13, which is incorporated by reference herein in its entirety. The results described herein demonstrate the distinctive structural features of the novel compounds impart a new mechanism of RNA polymerase inhibition. Thus, the present disclosure provides novel antibacterial compounds and methods of use thereof. In one embodiment, the disclosure also provides a composition comprising at least one compound of the disclosure and methods of treating or preventing a bacterial infection in a subject.

Compounds

The compounds of the present disclosure may be synthesized using techniques well-known in the art of organic synthesis. The starting materials and intermediates required for the synthesis may be obtained from commercial sources or synthesized according to methods known to those skilled in the art.

In one aspect, the disclosure provides compounds of formula (1):

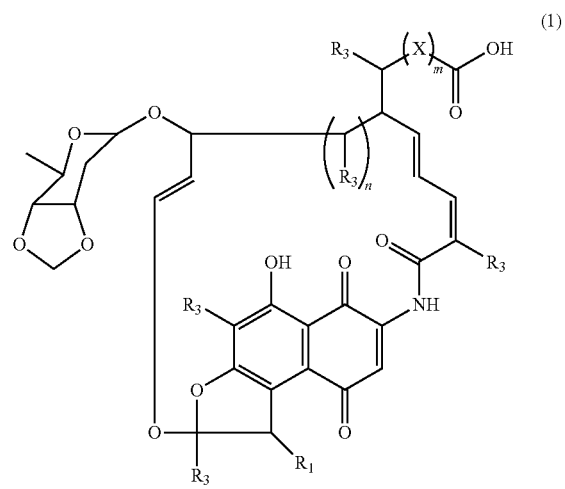

or a pharmaceutically acceptable salt thereof.

In some embodiments, $R_1$ is $CHR_4R_5$ or $OR_6$.

In some embodiments, $R_4$ and $R_5$ independently represent a hydrogen atom, a halogen atom, alkyl, carbocyclyl or heterocyclyl. In some embodiments, the carbocyclyl is a cycloalkyl or aryl. In some embodiments, the heterocyclyl is a heterocyclyl alkyl or a heteroaryl.

In some embodiments, $R_6$ is a hydrogen atom, alkyl, carbocyclyl, or heterocyclyl. In some embodiments, the carbocyclyl is a cycloalkyl or aryl. In some embodiments, the heterocyclyl is a heterocyclyl alkyl or a heteroaryl. In particular embodiments, wherein $R_1$ represents $OR_6$. In other particular embodiments, $R_1$ represents OH.

In some embodiments, each occurrence of $R_3$ independently represents a hydrogen atom, a halogen atom, alkyl, carbocyclyl, heterocyclyl, or $OR_7$. In some embodiments, the carbocyclyl is a cycloalkyl or aryl. In some embodiments, the heterocyclyl is a heterocyclyl alkyl or a heteroaryl.

In some embodiments, $R_7$ represents a hydrogen atom, alkyl, carbocyclyl, heterocyclyl, or $C(=O)R_8$. In some embodiments, the carbocyclyl is a cycloalkyl or aryl. In some embodiments, the heterocyclyl is a heterocyclyl alkyl or a heteroaryl.

In some embodiments, $R_8$ represents alkyl, carbocyclyl or heterocyclyl. In some embodiments, the carbocyclyl is a cycloalkyl or aryl. In some embodiments, the heterocyclyl is a heterocyclyl alkyl or a heteroaryl.

In particular embodiments, each $R_3$ independently represents alkyl or $OR_7$. In other particular embodiments, each $R_7$ independently represents a hydrogen atom or $C(=O)R_8$. In still other particular embodiments, $R_8$ is alkyl. In yet still other particular embodiments, each $R_3$ is independently selected from the group consisting of —OH, methyl, and —OC(=O)CH$_3$.

In some embodiments, X represents —O—, —NR$_9$—, —CR$_9$R$_{10}$—, or —C(=O)—. In some embodiments, $R_9$ and $R_{10}$ each independently represent a hydrogen atom, a halogen atom, alkyl, carbocyclyl or heterocyclyl. In some embodiments, the carbocyclyl is a cycloalkyl or aryl. In some embodiments, the heterocyclyl is a heterocyclyl alkyl or a heteroaryl.

In particular embodiments, X represents —O—, —CR$_9$R$_{10}$—, or —C(=O)—. In other particular embodiments, each of $R_9$ and $R_{10}$ are a hydrogen atom. In still other particular embodiments, each occurrence of X is selected from the group consisting of —O—, —C(=O)—, —CH$_2$—, and —C(CH$_3$)$_2$—.

In some embodiments, m represents an integer from 1 to 6 (e.g., 1, 2, 3, 4, 5, and 6, including all ranges and subranges in between).

In some embodiments, n represents an integer from 4 to 10 (e.g., 4, 5, 6, 7, 8, 9 and 10, including all ranges and subranges in between).

In some embodiments, the compound of formula (1) has the following structure

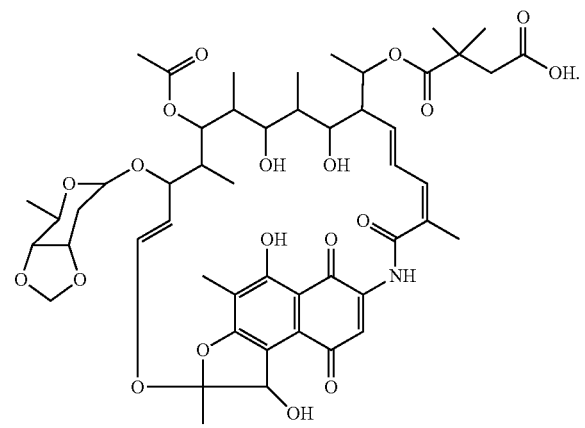 [SMILES: CC(=O)OC1C(C)C(OC2CC3OCOC3C(C)O2)/C=C/OC2(C)CC(O)c3c(c(C)c(O)c4c3C(=O)C=C(NC(=O)/C(C)=C\C=C\C(C(C)OC(=O)C(C)(C)CC(=O)O)C(O)C(C)C(O)C1C)C4=O)O2]

In some embodiments, the disclosure provides for compounds of formula (2):

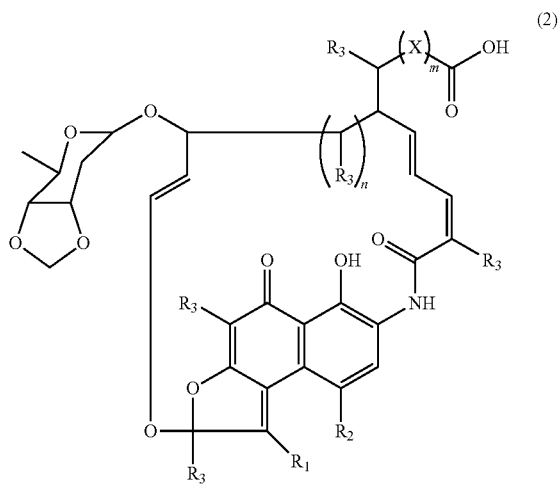

or pharmaceutically acceptable salts thereof.

In some embodiments, $R_1$ and $R_2$ each independently represent $CHR_4R_5$, $CR_4R_5$, $OR_6$, or —O—, wherein $R_1$ and $R_2$ may optionally be joined to form a ring.

In some embodiments, each occurrence of $R_4$ and $R_5$ independently represent a hydrogen atom, a halogen atom, alkyl, alkylene, carbocyclyl or heterocyclyl. In some embodiments, the carbocyclyl is a cycloalkyl or aryl. In some embodiments, the heterocyclyl is a heterocyclyl alkyl or a heteroaryl.

In some embodiments, each occurrence of $R_6$ independently represent a hydrogen atom, alkyl, alkylene, carbocyclyl or heterocyclyl. In some embodiments, the carbocyclyl is a cycloalkyl or aryl. In some embodiments, the heterocyclyl is a heterocyclyl alkyl or a heteroaryl.

In some embodiments, $R_1$ and $R_2$ each independently represent $OR_6$. In some embodiments, each $R_6$ independently represents a hydrogen atom or alkyl. In particular embodiments, $R_1$ and $R_2$ each independently represent $OR_6$ and —O—, and $R_1$ and $R_2$ are joined to form a ring. In other particular embodiments, $R_6$ is alkylene. In still other particular embodiments, $R_1$ represents —OCH$_2$— and $R_2$ represents —O—, and $R_1$ and $R_2$ are joined to form a ring.

In some embodiments, each occurrence of $R_3$ independently represents a hydrogen atom, a halogen atom, alkyl, carbocyclyl, heterocyclyl, or $OR_7$. In some embodiments, the carbocyclyl is a cycloalkyl or aryl. In some embodiments, the heterocyclyl is a heterocyclylalkyl or a heteroaryl.

In particular embodiments, each $R_3$ independently represents alkyl or $OR_7$. In other particular embodiments, each $R_7$ independently represents a hydrogen atom or $C(=O)R_8$. In still other particular embodiments, $R_8$ is alkyl. In yet still other particular embodiments, each $R_3$ is independently selected from the group consisting of —OH, methyl, and —OC(=O)CH$_3$.

In some embodiments, $R_7$ represents a hydrogen atom, alkyl, carbocyclyl, heterocyclyl, or $C(=O)R_8$. In some embodiments, the carbocyclyl is a cycloalkyl or aryl. In some embodiments, the heterocyclyl is a heterocyclyl alkyl or a heteroaryl.

In some embodiments, $R_8$ represents alkyl, carbocyclyl or heterocyclyl. In some embodiments, the carbocyclyl is a cycloalkyl or aryl. In some embodiments, the heterocyclyl is a heterocyclyl alkyl or a heteroaryl.

In some embodiments, X represents O, $NR_9$, $CR_9R_{10}$, or C(=O).

In some embodiments, $R_9$ and $R_{10}$ each independently represent a hydrogen atom, a halogen atom, alkyl, carbocyclyl or heterocyclyl. In some embodiments, the carbocyclyl is a cycloalkyl or aryl. In some embodiments, the heterocyclyl is a heterocyclyl alkyl or a heteroaryl.

In particular embodiments, X represents —O—, —$CR_9R_{10}$—, or —C(=O)—. In other particular embodiments, each of $R_9$ and $R_{10}$ are a hydrogen atom. In still other particular embodiments, each occurrence of X is selected from the group consisting of —O—, —C(=O)—, —$CH_2$—, and —$C(CH_3)_2$—.

In some embodiments, m represents an integer from 1 to 6 (e.g., 1, 2, 3, 4, 5, and 6, including all ranges and subranges in between).

In some embodiments, n represents an integer from 4 to 10 (e.g., 4, 5, 6, 7, 8, 9 and 10, including all ranges and subranges in between).

In some embodiments, the compound of Formula (2) has the following structure:

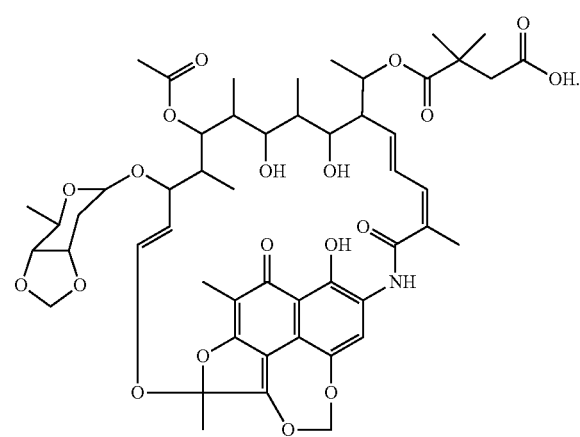 [SMILES: CC(=O)OC1C(C)C(OC2CC3OCOC3C(C)O2)/C=C/OC2(C)OC3=C(C)C(=O)c4c(O)c(cc5c4C3=C2OCO5)NC(=O)/C(C)=C\C=C\C(C(C)OC(=O)C(C)(C)CC(=O)O)C(O)C(C)C(O)C1C]

The compounds of formula (1) and (2), when isolated and purified, exhibit significant antibiotic activity, in particular against various antibiotic-resistant bacterium. In some embodiments, the compounds of formula (1) and (2) present in a substantially pure form. In some embodiments, "substantially pure," refers to a compound that has at least about 51% purity (e.g., about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, inclusive of all values and ranges therein). In some embodiments, contaminants (e.g., soil contaminants and less active antibiotics) have been removed from the substantially pure compound or mixture of compounds disclosed herein. The purity of the present compounds may be determined by conventional methods known in the art, such as high performance liquid chromatography (HPLC) as described in the examples.

In some embodiments, the pure form may refer to a compound or mixture of compounds of the present disclosure which are present as one or more enantiomers or diastereomers. In some embodiments, the pure form may refer to a compound or mixture of compounds of the present disclosure which are present as one or more enantiomers. In some embodiments, the pure form may refer to a compound or mixture of compounds of the present disclosure which are present as one or more diastereomers. In some embodiments, the compounds of formula (1) and (2) are present in a enantiomerically pure form. Such enantiomerically pure forms may have any combination of R and S at the chiral centers shown in the figure below:

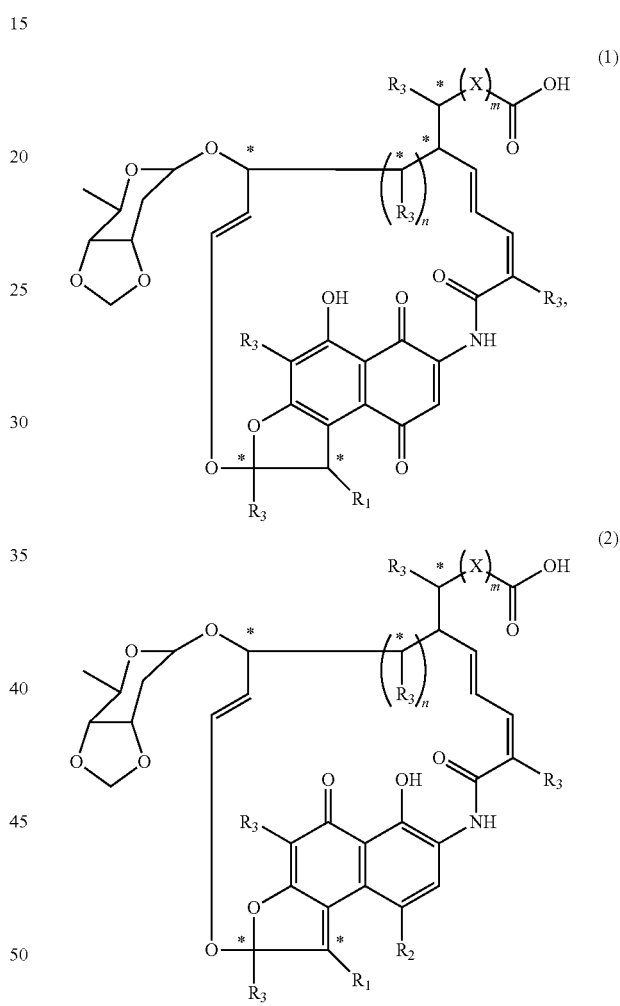

The * in the above structures represents possible a chiral center (e.g., depending on the identity of each $R_3$). Each chiral center may be independently R or S. The present disclosure encompasses compounds having all combinations of R or S at the various chiral centers indicated by *. In some embodiments, the compounds have a specific R or S configuration at one chiral center, but the remainder of the chiral centers are present as a mixture of R and S isomers. In some embodiments, 1, 2, 3, 4, 5, or 6 (or more) of the chiral centers have been resolved (i.e., 1, 2, 3, 4, 5, or 6, or more, chiral centers are either R or S, and not a mixture), such that the compound is present as a single stereoisomer.

In particular embodiments, each and every stereoisomer of the following compounds are provided:

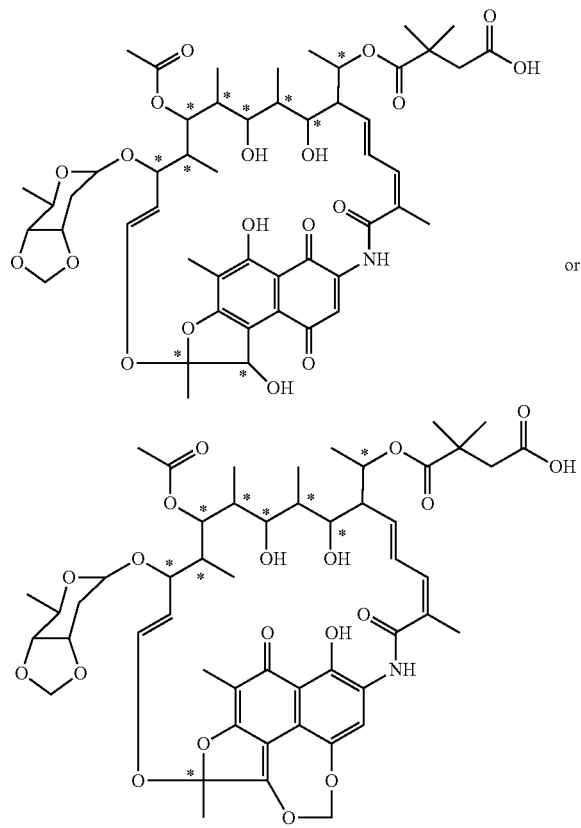

The * in the above structures represents a chiral center. Each chiral center may be independently R or S. The present disclosure encompasses compounds having all combinations of R or S at the various chiral centers indicated above by *. In some embodiments, the compounds have a specific R or S configuration at one chiral center, but the remainder of the chiral centers are present as a mixture of R and S isomers. In some embodiments, 1, 2, 3, 4, 5, 6, 7, 8, 9, or 10 of the chiral centers have been resolved (i.e., 1, 2, 3, 4, 5, 6, 7, 8, 9, or 10 of the chiral centers are either R or S, and not a mixture), such that the compound is present as a single stereoisomer.

As discussed herein, the compounds of formula (1) and (2) are potent antibiotics. In some embodiments, the compounds of formula (1) and (2) activity against rifamycin-resistant bacteria (e.g., as described herein). In some embodiments, a bacteria is considered to be rifamycin-resistant if the prescribed dose of rifamycin (e.g., as indicated on the FDA approved label for the indication being treated) is no longer therapeutically effective. In some embodiments, the compounds have an MIC (μg/mL) that is at least about 0.01 fold lower than the MIC of rifamycin measured for the rifamycin-resistant bacteria, e.g., about 0.01 fold, about 0.05 fold, about 0.10 fold, about 0.25 fold, about 0.50 fold, about 0.75 fold, about 1.0 fold, about 1.25 fold, 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 11 fold, about 12 fold, about 13 fold, about 14 fold, about 15 fold, about 16 fold, about 17 fold, about 18 fold, about 19 fold, about 20 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 150 fold, about 200 fold, about 250 fold, about 300 fold, about 350 fold, about 400 fold, about 450 fold, about 500 fold, about 550 fold, about 600 fold, about 650 fold, about 700 fold, about 750 fold, about 800 fold, about 850 fold, about 900 fold, about 950 fold, about 1000 fold or more, including all values and ranges inbetween. Methods of determining MIC are well known in the art.

In some embodiments, the compounds of formula (1) and (2) have an MIC value for any of the bacteria disclosed herein of less than about 1000 μg/mL, about 900 μg/mL, about 800 μg/mL, about 700 μg/mL, about 600 μg/mL, about 500 μg/mL, about 400 μg/mL, about 300 μg/mL, about 200 μg/mL, about 100 μg/mL, about 95 μg/mL, about 90 μg/mL, about 85 μg/mL, about 80 μg/mL, about 75 μg/mL, about 70 μg/mL, about 65 μg/mL, about 60 μg/mL, about 55 μg/mL, about 50 μg/mL, about 45 μg/mL, about 40 μg/mL, about 35 μg/mL, about 30 μg/mL, about 25 μg/mL, about 20 μg/mL, about 15 μg/mL, about 10 μg/mL, about 9 μg/mL, about 8 μg/mL, about 7 μg/mL, about 6 μg/mL, about 5 μg/mL, about 4 μg/mL, about 3 μg/mL, about 2 μg/mL, about 1 μg/mL, about 0.5 μg/mL, about 0.1 μg/mL, about 0.05 μg/mL, about 0.01 μg/mL, about 0.005 μg/mL, about 0.001 μg/mL, about 0.0005 μg/mL, about 0.0001 μg/mL, about 0.05 ng/mL, about 0.01 ng/mL, about 0.005 ng/mL, or about 0.001 ng/mL, or lower, including all values and ranges therebetween.

In some embodiments, the compounds of the disclosure when measured in vitro transcription assay (e.g., as described herein) inhibit RNA polymerase (RNAP) activity at a concentration that is at least about 0.01 fold lower than rifamycin, e.g., about 0.01 fold, about 0.05 fold, about 0.10 fold, about 0.25 fold, about 0.50 fold, about 0.75 fold, about 1.0 fold, about 1.25 fold, 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 11 fold, about 12 fold, about 13 fold, about 14 fold, about 15 fold, about 16 fold, about 17 fold, about 18 fold, about 19 fold, about 20 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 150 fold, about 200 fold, about 250 fold, about 300 fold, about 350 fold, about 400 fold, about 450 fold, about 500 fold, about 550 fold, about 600 fold, about 650 fold, about 700 fold, about 750 fold, about 800 fold, about 850 fold, about 900 fold, about 950 fold, about 1000 fold or more, including all values and ranges in between. In vitro transcription assays are well known in the art (See, e.g., J Vis Exp. 2016; (115): 54256; and Nature Communications. 2019; 9: 4147, each of which is herein incorporated by reference in its entirety for all purposes).

In some embodiments, the compounds of the disclosure inhibit RNAP activity as measured in an in vitro transcription assay (e.g., as described herein) a concentration of about 1000 μM or less, e.g., about 1000 μM, about 950 μM, about 900 μM, about 850 μM, about 800 μM, about 750 μM, about 700 μM, about 650 μM, about 600 μM, about 550 μM, about 500 μM, about 450 μM, about 400 μM, about 350 μM, about 300 μM, about 250 μM, about 200 μM, about 150 μM, about 100 μM, about 50 μM, about 45 μM, about 40 μM, about 35 μM, about 30 μM, about 25 μM, about 20 μM, about 15 μM, about 10 μM, about 9 μM, about 8 μM, about 7 μM, about 6 µM, about 5 µM, about 4 µM, about 3 µM, about 2 µM, about 1 µM, about 0.5 µM, about 0.1 µM, about 0.05 µM, about 0.01 µM, about 0.005 µM, about 0.001 µM, about 0.0005 µM, about 0.0001 µM, or lower, including all values and ranges therebetween.

Preparation of the Compounds of the Disclosure

The compounds of the disclosure may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the disclosure, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the disclosure may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the disclosure are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}C$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference in their entireties). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

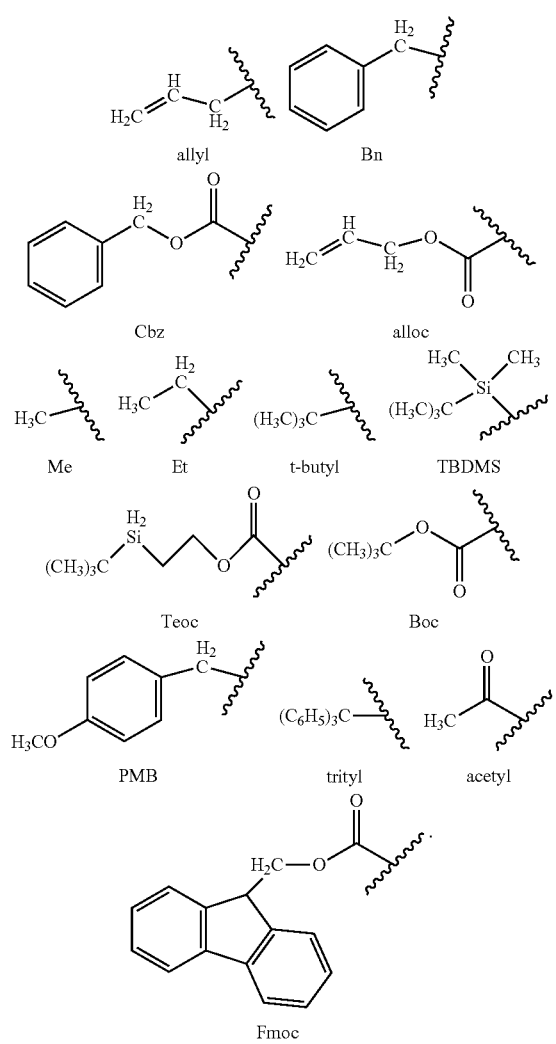

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In one embodiment, the compounds of the disclosure are synthesized using a semi-synthetic approach. In one embodiment, the compounds of the disclosure are synthesized using a biosynthetic approach. For example, in one embodiment, the compound is cyclized through an amide synthase reaction.

Pharmaceutical Compositions and Formulations

The disclosure also encompasses a pharmaceutical composition comprising a compound of the disclosure. In one embodiment, the pharmaceutical composition is useful for inhibiting bacterial infections. In one embodiment, the pharmaceutical composition is useful for overcoming antibacterial resistance. Such a pharmaceutical composition may consist of a compound of the disclosure in a form suitable for administration to a subject. The compound of the disclosure may be present in the pharmaceutical composition in the form of a physiologically acceptable salt, such as in combination with a physiologically acceptable cation, as is well known in the art.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

In an embodiment, the pharmaceutical compositions useful for practicing the method of the disclosure may be administered to deliver a dose of between 1 ng/kg/day and 100 mg/kg/day (e.g., about 1 ng/kg/day, about 10 ng/kg/day, 100 ng/kg/day, about 500 ng/kg/day, about 1000 ng/kg/day, about 5000 ng/kg/day, about 10000 ng/kg/day, about 50000 ng/kg/day, about 1 mg/kg/day, about 10 mg/kg/day, about 100 mg/kg/day, inclusive of all value sand ranges therebetween). In another embodiment, the pharmaceutical compositions useful for practicing the disclosure may be administered to deliver a dose of between 1 ng/kg/day and 500 mg/kg/day (e.g., about 1 ng/kg/day, about 10 ng/kg/day, 100 ng/kg/day, about 500 ng/kg/day, about 1000 ng/kg/day, about 5000 ng/kg/day, about 10000 ng/kg/day, about 50000 ng/kg/day, about 1 mg/kg/day, about 10 mg/kg/day, about 100 mg/kg/day, about 200 mg/kg/day, about 300 mg/kg/day, about 400 mg/kg/day, or about 500 mg/kg/day inclusive of all value sand ranges therebetween).

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient (e.g., about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, Pharmaceutical compositions that are useful in the methods of the disclosure may be suitably developed for oral, rectal, vaginal, topical, transdermal, ophthalmic, intrathecal or another route of administration. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as cattle, pigs, horses, sheep, cats, and dogs.

In one embodiment, the compositions of the disclosure are formulated using one or more pharmaceutically acceptable excipients or carriers. In one embodiment, the pharmaceutical compositions of the disclosure comprise a therapeutically effective amount of a compound of the disclosure and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention or reduction of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; antiseptics; antiviral agents; anticoagulants; stabilizing agents; and pharmaceutically acceptable polymeric or hydrophobic materials. Other "additional ingredients" which may be included in the pharmaceutical compositions of the disclosure are known in the art and described, for example in Genaro, ed. (1985, Remington's Pharmaceutical Sciences, Mack Publishing Co., Easton, Pa.), which is incorporated herein by reference.

The composition of the disclosure may comprise a preservative from about 0.005% to 2.0% by total weight of the composition. The preservative is used to prevent spoilage in the case of exposure to contaminants in the environment. Examples of preservatives useful in accordance with the disclosure included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

In some embodiments, the pharmaceutical compositions of the present disclosure (e.g., containing therapeutically effective amounts of one or more compounds of formula (1)

and/or (2), may be formulated as immediate release formulation, a delayed release formulation, or a sustained release formulation, and may comprise at least one pharmaceutically acceptable carrier, diluent, and/or excipient. Pharmaceutically acceptable carriers, diluents or excipients include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier.

In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, aqueous and non-aqueous solutions. Pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate. Aqueous carriers suitable for use in the present application include, but are not limited to, water, ethanol, alcoholic/aqueous solutions, glycerol, emulsions or suspensions, including saline and buffered media.

Liquid carriers suitable for use in the present application include, but are not limited to, water (partially containing additives, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil).

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the disclosure may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

The compositions useful within the disclosure comprise at least one compound of formula (1) or formula (2). The compositions of the disclosure may be used in aqueous emulsions such as latexes, water-based paints and coatings, caulks and adhesives, tape joint compounds, mineral slurries, water-cooling systems, personal care products, soaps and detergents, disinfectants, cleaners, and sanitizers, pesticide products, oilfield water and water-based fluids used in oilfield applications including drilling muds, fracturing fluids, and hydrotest fluids, and the like. In one embodiment, the composition is an antimicrobial composition. In one embodiment, the composition is an antiseptic.

Solid carriers suitable for use in the present application include, but are not limited to, inactive substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets may contain up to 99% of the active compound. Suitable solid carriers include, for example, calcium phosphate, magnesium stearate, talc, sugars, lactose, dextrin, starch, gelatin, cellulose, polyvinylpyrrolidone, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent.

The tablets may optionally be coated or scored and may be formulated so as to provide delayed or controlled release of the active ingredient therein using, for example, hydroxypropyl methylcellulose in varying proportions to provide the desired release profile. Tablets may optionally be provided with an enteric coating, to provide release in parts of the gut other than the stomach.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations described herein. Diluents increase the bulk of a solid pharmaceutical composition and/or combination, and may make a pharmaceutical dosage form containing the composition and/or combination easier for the patient and care giver to handle. In various embodiments, diluents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc, and/or mixtures of any of the foregoing. Specific examples of microcrystalline cellulose include those sold under the Trademark Avicel (FMC Corp., Philadelphia, Pa.), for example, Avicel™ pH101, Avicel™ pH102 and Avicel™ pH112; lactose include lactose monohydrate, lactose anhydrous and Pharmatose DCL21; dibasic calcium phosphate includes Emcompress.

Lubricants are used to facilitate tablet manufacture, promoting powder flow and preventing particle capping (i.e., particle breakage) when pressure is relieved. Useful lubricants are magnesium stearate, calcium stearate, stearic acid, glyceryl behenate, talc, colloidal silicon dioxide such as Aerosil™ 200, mineral oil (in PEG), hydrogenated vegetable oil (e.g., comprised of hydrogenated and refined triglycerides of stearic and palmitic acids), combinations thereof.

Binders are used to impart cohesive qualities to a tablet, and thus ensure that the tablet or tablet layer remains intact after compression. Suitable binder materials include, but are not limited to, starch (including corn starch and pregelatinized starch), gelatin, sugars (including sucrose, glucose, dextrose and lactose), polyethylene glycol, polyvinyl alcohol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum, and combinations thereof. Examples of polyvinylpyrrolidone include povidone, copovidone and crospovidone.

Fillers include, for example, materials such as silicon dioxide, titanium dioxide, alumina, talc, kaolin, powdered cellulose, microcrystalline cellulose, urea, sodium chloride, as well as saccharides, or combinations thereof. Any suitable saccharide may be used in the composition of the present invention. As used herein, the "saccharides" used in the invention include sugar alcohols, monosaccharides, disaccharides, and oligosaccharides. Exemplary sugar alcohols include, but are not limited to, xylitol, mannitol, sorbitol, erythritol, lactitol, pentitol, and hexitol. Exemplary monosaccharides include, but are not limited to, glucose, fructose, aldose and ketose. Exemplary disaccharides include, but are not limited to, sucrose, isomalt, lactose, trehalose, and maltose. Exemplary oligosaccharides include, but are not limited to, fructo-oligosaccharides, inulin, galacto-ologosaccharides, and mannan-oligosaccharides. In some embodiments, the saccharide is sorbitol, mannitol, or xylitol. In some embodiments, the saccharide is sorbitol. In some embodiments, the saccharide is sucrose.

Disintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). Other non-limiting examples of suitable disintegrants include, for example, lightly crosslinked polyvinyl pyrrolidone, corn starch, potato starch, maize starch and modified starches, croscarmellose sodium, crospovidone, sodium starch glycolate, and combinations and mixtures thereof.

The pharmaceutical formulation of the present invention may be prepared by any well-known methods in the art, such as mixing, dissolving, granulating, dragee-making, levigating, emulsifying, encapsulating, entrapping, or lyophilizing processes. As mentioned above, the compositions of the present disclosure may include one or more pharmaceutically acceptable carriers such as excipients and adjuvants that facilitate processing of active molecules into preparations for pharmaceutical use.

In some embodiments of the present disclosure, the pharmaceutical composition may be prepared in an oral formulation. For oral administration, the compounds can be formulated readily by combining the active compounds with pharmaceutically acceptable carriers known in the art. Such carriers enable the compounds disclosed herein to be formulated as tablets, pills, dragees, capsules, liquids, gels, syrups, slurries, suspensions and the like, for oral ingestion by a subject. Pharmaceutical compositions for oral use may be obtained as solid excipients, optionally grinding a resulting mixture, and processing the mixture of granules, after adding suitable adjuvants, if desired, to obtain tablets or dragee cores. Such oral pharmaceutical compositions may also be prepared by milling or melt extrusion. Suitable excipients may be any of those disclosed herein and, in particular, fillers such as sugars, including lactose, sucrose, mannitol, or sorbitol; cellulose formulation such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP) formulation. Also, disintegrating agents may be employed, such as cross-linked polyvinylpyrrolidone, agar, or alginic acid or a salt thereof such as sodium alginate. Wetting agents, such as sodium dodecyl sulfate and the like, may be added.

In some embodiments, one or more of the compounds of formula (1) and/or (2) are combined with excipients to form a core comprising an active (an active core), thereby forming a solid dosage form. In some embodiments, the active core may comprise an inert particle such as a sugar sphere with an appropriate mean particle size. In one embodiment, the inactive core may be a sugar sphere, a cellulose sphere, a spheroidal silicon dioxide bead, a buffer crystal or an encapsulated buffer crystal, such as calcium carbonate, sodium bicarbonate, fumaric acid, tartaric acid, etc. Buffer crystals are useful to alter the microenvironment. Alternatively in accordance with other embodiments, drug-containing microgranules or pellets may be prepared by rotogranulation, high-shear granulation and extrusion-spheronization or compression of the drug (as mini-tablets, e.g., having a diameter of about 2 mm or more), a polymeric binder and optionally fillers/diluents.

In some embodiments, dragee cores may be provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds doses.

In some embodiments, pharmaceutical compositions described herein comprise one or more delayed release components. As used herein, "delayed release" refers to a pharmaceutical formulation which substantially prevents the release (meaning releasing no more than about 5-10%) of the active for a defined period of time after oral administration. In some embodiments, delayed release substantially prevents release of the active for at least 30 minutes after oral administration, e.g., 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 3 hr, 4 hr, 5 hr, 6 hr, or more.

In some embodiments, delayed release is achieved by appropriately coating a drug-containing component with one or more suitable delayed-release polymers (also referred to as a controlled release polymer or rate-controlling polymer) or embedding the drug in a matrix comprising one or more suitable delayed-release polymers. Suitable delayed-release polymers include pharmaceutically acceptable water-insoluble polymers (also referred to as hydrophobic polymers), pharmaceutically acceptable water-soluble polymers (also referred to as hydrophilic polymers), pharmaceutically acceptable gastrosoluble polymers, pharmaceutically acceptable enteric polymers, and combinations thereof.

Non-limiting examples of pharmaceutically acceptable water-insoluble polymers include acrylic polymers, methacrylic acid polymers, acrylic copolymers, such as a methacrylic acid-ethyl acrylate copolymer available under the trade name of EUDRAGIT® (type L, RL, RS and NE30D), and their respective esters, zein, waxes, shellac and hydrogenated vegetable oil, cellulose derivatives, such as ethyl cellulose, cellulose acetate, cellulose acetate butyrate, and the like.

Non-limiting examples of pharmaceutically acceptable water-soluble polymers include homopolymers and copolymers of N-vinyl lactams, including homopolymers and copolymers of N-vinyl pyrrolidone, e.g. polyvinylpyrrolidone (PVP), copolymers of N-vinyl pyrrolidone and vinyl acetate or vinyl propionate, cellulose esters and cellulose ethers, in particular methylcellulose and ethylcellulose, hydroxyalkylcelluloses, in particular hydroxypropylcellulose, hydroxyalkylalkylcelluloses, and hydroxypropylmethylcellulose, cellulose phthalates, succinates, butyrates, or trimellitates, in particular cellulose acetate phthalate, hydroxypropylmethylcellulose phthalate, hydroxypropylmethylcellulose succinate, and hydroxypropylmethylcellulose acetate succinate; high molecular polyalkylene oxides such as polyethylene oxide and polypropylene oxide and copolymers of ethylene oxide and propylene oxide, polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially saponified "polyvinyl alcohol"), polyvinyl alcohol, polyethylene glycol oligo- and polysaccharides such as carrageenans, galactomannans and xanthan gum, or mixtures of one or more thereof.

Non-limiting examples of gastrosoluble polymers include maltrin, an aminoalkyl methacrylate copolymer available under the trade name of EUDRAGIT® (type E100 or EPO), polyvinylacetal diethylaminoacetate e.g., AEA® available from Sankyo Company Limited, Tokyo (Japan), and the like.

Non-limiting examples of such enteric polymers include carboxymethylethylcellulose, cellulose acetate phthalate (CAP), cellulose acetate succinate, methylcellulose phthalate, hydroxymethylethylcellulose phthalate, hydroxypropylmethylcellulose phthalate (HPMCP), hydroxypropylmethylcellulose acetate succinate (HPMCAS), polyvinyl alcohol phthalate, polyvinyl butyrate phthalate, polyvinyl acetal phthalate (PVAP), a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, cellulose acetate hexahydrophthalate, hydroxypropyl methylcellulose hexahydrophthalate, hydroxypropyl methylcellulose phthalate, cellulose propionate phthalate, cellulose acetate maleate, cellulose acetate trimellitate, cellulose acetate butyrate, cellulose acetate propionate, methacrylic acid/methacrylate polymer (acid number 300 to 330 and also known as EUDRAGIT L), methacrylic acid-methyl methacrylate copolymer, ethyl methacrylate-methylmethacrylate-chlorotrimethylammonium ethyl methacrylate copolymer, and the like, and combinations comprising one or more of the foregoing enteric polymers. Other examples include natural resins, such as shellac, SANDARAC, copal collophorium, and combinations comprising one or more of the foregoing polymers. Yet other examples of enteric polymers include synthetic resin bearing carboxyl groups. The term "enteric polymer" as used herein is defined to mean a polymeric substance that when used in an enteric coat formulation, is substantially insoluble and/or substantially stable under acidic conditions at a pH of less than about 5 and which are substantially soluble or can decompose under conditions exhibiting a pH of about 5 or more.

Non-limiting examples of hydrophilic polymers include hydroxypropyl celluloses (HPC), hydroxypropyl methylcelluloses, methylcelluloses, polyethylene oxides, sodium carboxymethyl celluloses, and the like, or combinations thereof.

In some embodiments, the delayed release coating may comprise about 40 wt % to about 95 wt % of any of pharmaceutically acceptable polymers listed above (e.g., about 45%, about 50%, about 55%, about 60%, about 65%, about 70%, about 75%, about 80%, about 85%, about 90%, inclusive of all values and subranges therebetween) and about 5 wt % to about 60 wt % plasticizer (e.g., about 10%, about 15%, about 20%, about 25%, about 30%, about 35%, about 40%, about 45%, about 50%, about 55%, inclusive of all values and subranges therebetween) based on the total weight of the polymer coating. The relative proportions of ingredients, notably the ratio of the enteric polymer to plasticizer can be varied according to methods known to those of skill in the art of pharmaceutical formulation.

In some embodiments, the delayed release is an osmotic system. An osmotic system is a core with a semi-permeable outer membrane and one or more openings. The semipermeable membrane is impermeable to the compounds of formula (1) and/or (2), but permits entry of water by osmosis from the outside into the osmotic system. As the core passes through the body, water is absorbed through the semipermeable membrane via osmosis, and the resulting osmotic pressure is used to push the active drug through the opening(s) in the core. Total amount of drug release and the release rate can be controlled by appropriately selecting the thickness and porosity of the semipermeable membrane, the composition of the core and the number and size of the opening(s). Formulation aspects, administration forms and information about preparation processes are described, for example, in the following publications:

Both single-chamber systems (elementary osmotic pump) and two-chamber systems (push-pull systems) are suitable for delayed release component described here. In embodiments, the shell of the osmotic release system comprises either a single-chamber system or a two-chamber system of the semipermeable membrane. Non-limiting examples of shell materials include cellulose acetate or mixtures of cellulose acetate and polyethylene glycol.

In some embodiments, the core of an osmotic single-chamber system comprises a hydrophilic water-swellable polymer, e.g., xanthan. This is an anionic heteropolysaccharide which is commercially available for example under the name Rhodigel® (produced by Rhodia). It may be present in an amount of from about 20 to about 50% (e.g., about 25%, about 30%, about 35%, about 40%, about 45%, inclusive of all values and subranges therebetween) based on the total mass of the core ingredients.

Another ingredient of the core may be a vinylpyrrolidone-vinyl acetate copolymer. This copolymer is known in the art and can be produced with any desired monomer mixing ratios. A non-limiting example of such a copolymer is Kollidon® VA64 (produced by BASF). It generally has a weight average molecular weight (Mw), determined by light-scattering measurements, of about 45 000 to about 70 000. The amount of the vinylpyrrolidone-vinyl acetate copolymer in the core may be 10 to 30% (e.g., about 15%, about 20%, about 25%, inclusive of all values and subranges therebetween), based on the total mass of the core ingredients.

In some embodiments, hydrophilic swellable polymers may be present, where appropriate, in the core. Non-limiting examples of hydrophilic swellable polymers include for example, hydroxypropylcellulose, hydroxypropylmethylcellulose, sodium carboxymethylcellulose, sodium carboxymethyl starch, polyacrylic acids and salts thereof.

Suitable substances which can be used as water swellable substances include, for example, low-substituted hydroxypropyl cellulose, e.g., L-HPC; cross-linked polyvinyl pyrrolidone (PVP-XL), e.g., Kollidon® CL and Poly-plasdone® XL; cross-linked sodium carboxymethylcellulose, e.g., Ac-di-sol, Primellose®; sodium starch glycolate, e.g., Primojel®; sodium carboxymethylcellulose, e.g., Nym-cel ZSBlO®; sodium carboxymethyl starch, e.g., Explotab®; ion-exchange resins, e.g., Dowex® or Amber-lite®; microcrystalline cellulose, e.g., Avicel®; starches and pregelatinized starch, e.g., Starch 1500®, Sepistab ST200®; formalin-casein, e.g., Plas-Vita®, and combinations comprising one or more of the foregoing water swellable substances.

Osmotically active additives which are additionally present where appropriate in the core are, for example, pharmaceutically acceptable water-soluble substances, such as, for example, the water-soluble excipients mentioned in pharmacopoeias or "Remington Pharmaceutical Science," (1985) 17th ed. Edited by Alfonso R. Gennaro. Mack Publishing Co., Easton, Pa. which is herein incorporated by reference in its entirety for all purposes. It is possible in particular to use water-soluble salts of inorganic or organic acids or nonionic organic substances with high solubility in water, such as, for example, carbohydrates, especially sugars, sugar alcohols or amino acids. For example, the osmotically active additives can be selected from inorganic salts such as chlorides, sulfates, carbonates and bicarbonates of alkali metals or alkaline earth metals, such as lithium, sodium, potassium, magnesium, calcium, and phosphates, hydrogen phosphates or dihydrogen phosphates, acetates, succinates, benzoates, citrates or ascorbates thereof. It is furthermore possible to use pentoses such as arabinose, ribose or xylose, hexoses such as glucose, fructose, galactose or mannose, disaccharides such as sucrose, maltose or lactose or trisaccharides such as raffinose. The water-soluble amino acids include glycine, leucine, alanine or methionine. Sodium chloride is particularly preferably used according to the invention. The osmotically active additives are preferably present in an amount of from 10 to 30% based on the total mass of the core ingredients.

Pharmaceutically acceptable excipients which may be additionally present where appropriate in the core include, for example, buffer substances such as sodium bicarbonate, binders such as hydroxypropylcellulose, hydroxypropylmethylcellulose and/or polyvinylpyrrolidone, lubricants such as magnesium stearate, wetting agents such as sodium lauryl sulfate and/or flow regulators such as colloidal silicon dioxide.

The osmotically active additives used in the core of the osmotic two-chamber system may be the same as in the case of the single-chamber system described above.

In certain embodiments, the delayed release component is a matrix. As used herein, the term "matrix" means a composition in which the drug is embedded or dispersed in water soluble, water insoluble, or hydrophilic polymers, or lipophilic maters, in order to achieve delayed release of the drug. The mechanisms of the drug release generally involve drug diffusion through a viscous gel layer or tortuous channels; and/or drug dissolution via gradual erosion or degradation of the polymer(s). In some embodiments, the matrix comprises swellable/erodable polymers, for example hydrophilic polymers which in contact with the water form a gel of high viscosity. In other embodiments, the matrix comprises water-insoluble polymers or lipophilic polymers.

For example, the matrix may be prepared using one or more hydrophilic polymers (e.g., hydroxypropyl cellulose, hydroxypropyl methylcellulose, polyethylene oxide), one or more lipophilic materials (e.g., camauba wax, hardened castor oil, hardened rape seed oil, polyglycerin fatty acid ester), and/or coating tablets or granules with one or more delayed release polymers (e.g., cellulose polymers such as ethylcellulose; acrylic acid copolymer such as aminoalkyl methacrylate copolymer RS [Eudragit RS (trade name, Degussa Co.)], ethyl acrylate-methyl methacrylate copolymer suspension [Eudragit NE (trade name, Degussa Co.)]).

In certain embodiments, the delayed release component is a matrix comprising one or more hydrophilic polymers. The viscosity of the hydrophilic polymer is, for example, about 1 mPa·s to about 200000 mPa·s, or about 4 mPa·s to about 120000 mPa·s, or about 4 mPa·s to about 5000 mPa·s as measured using a Brookfield viscometer in a 2% by weight aqueous solution at 20° C. The release duration of the active from the matrix can be modified by appropriately selecting the viscosity of the hydrophilic polymer.

Non-limiting examples of suitable hydrophilic polymers include hydroxypropyl celluloses (HPC) such as HPC-SSL (trade name, manufactured by NIPPON SODA CO., viscosity of 2% by weight aqueous solution at 20° C.: 2.0-2.9 mPa·s), HPC-SL (trade name, manufactured by NIPPON SODA CO., viscosity of 2% by weight aqueous solution at 20° C.: 3.0-5.9 mPa·s), HPC-L (trade name, manufactured by NIPPON SODA CO., viscosity of 2% by weight aqueous solution at 20° C.: 6.0-10.0 mPa·s), HPC-M (trade name, manufactured by NIPPON SODA CO., viscosity of 2% by weight aqueous solution at 20° C.: 150-400 mPa·s), HPC-H (trade name, manufactured by NIPPON SODA CO., viscosity of 2% by weight aqueous solution at 20° C.: 1000-4000 mPa·s); hydroxypropyl methylcelluloses such as Metolose SB-4 (trade name, manufactured by Shin-Etsu Chemical CO., viscosity of 2% by weight aqueous solution at 20° C.: about 4 mPa·s), TC-5RW (trade name, manufactured by Shin-Etsu Chemical CO., viscosity of 2% by weight aqueous solution at 20° C.: about 6 mPa·s), TC-5S (trade name, manufactured by Shin-Etsu Chemical CO., viscosity of 2% by weight aqueous solution at 20° C.: about 15 mPa·s), Metolose 60SH-50 (trade name, manufactured by Shin-Etsu Chemical CO., viscosity of 2% by weight aqueous solution at 20° C.: about 50 mPa·s), Metolose 65SH-50 (trade name, manufactured by Shin-Etsu Chemical CO., viscosity of 2% by weight aqueous solution at 20° C.: about 50 mPa·s), Metolose 90SH-100 (trade name, manufactured by Shin-Etsu Chemical CO., viscosity of 2% by weight aqueous solution at 20° C.: about 100 mPa·s), Metolose 90SH-100SR (trade name, manufactured by Shin-Etsu Chemical CO., viscosity of 2% by weight aqueous solution at 20° C.: about 100 mPa·s), Metolose 65SH-400 (trade name, manufactured by Shin-Etsu Chemical CO., viscosity of 2% by weight aqueous solution at 20° C.: about 400 mPa·s), Metolose 90SH-400 (trade name, manufactured by Shin-Etsu Chemical CO., viscosity of 2% by weight aqueous solution at 20° C.: about 400 mPa·s), Metolose 65SH-1500 (trade name, manufactured by Shin-Etsu Chemical CO., viscosity of 2% by weight aqueous solution at 20° C.: about 1500 mPa·s), Metolose 60SH-4000 (trade name, manufactured by Shin-Etsu Chemical CO., viscosity of 2% by weight aqueous solution at 20° C.: about 4000 mPa·s), Metolose 65SH-4000 (trade name, manufactured by Shin-Etsu Chemical CO., viscosity of 2% by weight aqueous solution at 20° C.: about 4000 mPa·s), Metolose 90SH-4000 (trade name, manufactured by Shin-Etsu Chemical CO., viscosity of 2% by weight aqueous solution at 20° C.: about 4000 mPa·s), Metolose 90SH-4000SR (trade name, manufactured by Shin-Etsu Chemical CO., viscosity of 2% by weight aqueous solution at 20° C.: about 4000 mPa·s), Metolose 90SH-30000 (trade name, manufactured by Shin-Etsu Chemical CO., viscosity of 2% by weight aqueous solution at 20° C.: about 30000 mPa·s), Metolose 90SH-100000 (trade name, manufactured by Shin-Etsu Chemical CO., viscosity of 2% by weight aqueous solution at 20° C.: about 100000 mPa·s), Metolose 90SH-100000SR (trade name, manufactured by Shin-Etsu Chemical CO., viscosity of 2% by weight aqueous solution at 20° C.: about 100000 mPa·s); methylcelluloses such as Metolose SM15 (trade name, manufactured by Shin-Etsu Chemical CO.; viscosity: about 15 mPa·s, 2% by weight aqueous solution, 20° C.), Metolose SM25 (trade name, manufactured by Shin-Etsu Chemical CO., viscosity of 2% by weight aqueous solution at 20° C.: about 25 mPa·s), Metolose SM100 (trade name, manufactured by Shin-Etsu Chemical CO., viscosity of 2% by weight aqueous solution at 20° C.: about 100 mPa·s), Metolose SM400 (trade name, manufactured by Shin-Etsu Chemical CO., viscosity of 2% by weight aqueous solution at 20° C.: about 400 mPa·s), Metolose SM1500 (trade name, manufactured by Shin-Etsu Chemical CO., viscosity of 2% by weight aqueous solution at 20° C.: about 1500 mPa·s), Metolose SM4000 (trade name, manufactured by Shin-Etsu Chemical CO., viscosity of 2% by weight aqueous solution at 20° C.: about 4000 mPa·s), Metolose SM8000 (trade name, manufactured by Shin-Etsu Chemical CO., viscosity of 2% by weight aqueous solution at 20° C.: about 8000 mPa·s); polyethylene oxides such as WSR N-12K (trade name, manufactured by Union Carbide Co., viscosity of 2% by weight aqueous solution at 20° C.: 400-800 mPa·s), WSR N-60K (trade name, manufactured by Union Carbide Co., viscosity of 2% by weight aqueous solution at 20° C.: 2000-4000 mPa·s), WSR 301 (trade name, manufactured by Union Carbide Co., viscosity of 1% by weight aqueous solution at 25° C.: 1500-4500 mPa·s), WSR Coagulant (trade name, manufactured by Union Carbide Co., viscosity of 1% by weight aqueous solution at 25° C.: 4500-7500 mPa·s), WSR 303 (trade name, manufactured by Union Carbide Co., viscosity of 1% by weight aqueous solution at 25° C.: 7500-10000 mPa·s), WSR 308 (trade name, manufactured by Union Carbide Co., viscosity of 1% by weight aqueous solution at 25° C.: 10000-15000 mPa·s); sodium carboxymethyl celluloses such as Sunrose F-150MC (trade name, manufactured by Nippon Paper Industries Co., viscosity of 1% by weight aqueous solution at 25° C.: 1200-1800 mPa·s), Sunrose F-300MC (trade name, manufactured by Nippon Paper Industries Co., viscosity of 1% by weight aqueous solution at 25° C.: 2500-3000 mPa·s), Sunrose F-1000MC (trade name, manufactured by Nippon Paper Industries Co., viscosity of 1% by weight aqueous solution at 25° C.: 8000-12000 mPa·s); and the like, or combinations thereof.

The hydrophilic matrix may further contain a pH-dependent polymer. The term "pH-dependent" refers to a polymer which releases the active at a certain pH. Non-limiting examples of suitable pH-dependent polymers include hydroxypropyl methylcellulose phthalate, cellulose acetate phthalate, carboxymethyl ethyl cellulose, methyl methacrylate-methacrylic acid copolymer, methacrylic acid-ethyl acrylate copolymer, ethyl acrylate-methyl methacrylate-trimethylammoniumethyl methacrylate chloride copolymer, methyl methacrylate-ethyl acrylate copolymer, methacrylic acid-methyl acrylate-methyl methacrylate copolymer, hydroxypropyl cellulose acetate succinate, polyvinyl acetate phthalate and the like, and combinations thereof.

In some embodiments, the pharmaceutical composition is formulated as a sustained release formulations, e.g., by appropriately integrating additional polymers into the composition, or as coatings over the core (e.g., pellet or granule). The polymers useful for this purpose can be, but are not limited to, ethylcellulose; hydroxypropylmethylcellulose; hydroxypropylcellulose; hydroxyethylcellulose; carboxymethylcellulose; methylcellulose; nitrocellulose; Eudragit R; Eudragit RS; and Eudragit RL; Carbopol; polyethyleneoxide or polyethylene glycols with molecular weights in excess of 8,000 daltons. In some embodiments, these polymers are present concentrations from about 4-20 w/w % (e.g., about 4, about 5, about 6, about 7, about 8, about 9, about 10, about 11, about 12, about 13, about 14, about 15, about 16, about 17, about 18, about 19, or about 20% w/w %). The sustained release polymers may be combined with the delayed release components described above.

The compositions useful within the disclosure may further comprise at least one additional antimicrobial agent. Non-limiting examples of the at least one additional antimicrobial agent are levofloxacin, doxycycline, neomycin, clindamycin, minocycline, gentamycin, rifampin, chlorhexidine, chloroxylenol, methylisothizolone, thymol, α-terpineol, cetylpyridinium chloride, hexachlorophene, triclosan, nitrofurantoin, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, lipopeptides, ketolides, polyenes, azoles, echinocandines, and any combination thereof.

In one embodiment, the compound of the disclosure and the at least one additional antimicrobial agent act synergistically in preventing, reducing or treating bacterial infections. A synergistic effect may be calculated, for example, using suitable methods such as, for example, the Sigmoid-$E_{max}$ equation (Holford & Schemer, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Medical Devices

The disclosure contemplates applying to or coating medical devices with the compositions useful within the disclosure. Non-limiting examples of medical devices include disposable or permanent catheters, (e.g., central venous catheters, dialysis catheters, long-term tunneled central venous catheters, short-term central venous catheters, arterial catheters, peripherally inserted central catheters, peripheral venous catheters, pulmonary artery Swan-Ganz catheters, urinary catheters, and peritoneal catheters, drainage catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings (e.g., intravenous tubes, breathing tubes, dental water lines, dental drain tubes, and feeding tubes), fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field.

Medical devices also include any device that may be inserted or implanted into a human being or other animal, or placed at the insertion or implantation site such as the skin near the insertion or implantation site, and that include at least one surface which is susceptible to colonization by microorganisms and/or biofilm-embedded microorganisms. Also contemplated within the disclosure is any other surface that may be desired or necessary to prevent microorganisms and/or biofilm-embedded microorganisms from growing or proliferating on at least one surface of the medical device, or to remove or clean microorganisms and/or biofilm-embedded microorganisms from the at least one surface of the medical device, such as the surfaces of equipment in operating rooms, emergency rooms, hospital rooms, clinics, and bathrooms. In one specific embodiment, the composition is integrated into an adhesive, such as tape, thereby providing an adhesive that may prevent or reduce growth or proliferation of microorganisms and/or biofilm embedded-microorganisms on at least one surface of the adhesive.

Implantable medical devices include orthopedic implants that may be inspected for contamination or infection by microorganisms and/or biofilm-embedded microorganisms using endoscopy. Insertable medical devices include catheters and shunts that can be inspected without invasive techniques such as endoscopy. The medical devices may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex® (polytetrafluoroethylene), Dacron® (polyethylene tetraphthalate), Teflon® (polytetrafluoroethylene), latex, elastomers and Dacron® sealed with gelatin, collagen or albumin, and derivatives or combinations thereof. The medical devices include at least one surface for applying the biofilm-penetrating composition. In one embodiment, the biofilm-penetrating composition is applied to the entire medical device.

Methods

In one aspect, the disclosure provides a method of preventing or reducing the growth or proliferation of microorganisms. In one embodiment, the method comprises, contacting the microorganism with a composition comprising a compound of the disclosure.

In one embodiment, the microorganism is a bacterium. In one embodiment the bacteria include at least eleven distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

In one embodiment, the bacteria include cocci, nonenteric rods, enteric rods, nonsporulating rods, and sporulating rods. In one embodiment, bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, Fusobacterium, Brachyspira, Legionella, Helicobacter, Actinomyces, Bacillus, Clostridium, Corynebacterium, Erysipelothrix, Lactobacillus, Listeria, Mycobacterium, Myxococcus, Nocardia, Staphylococcus, Streptococcus, Streptomyces, Firmicutes, Borrelia, Campylobacter, Cryptosporidium, Entamoeba, Enterobacter, Gard-* nerella, *Leishmania, Moraxella, Mycoplasma, Providencia, Serpulina, Toxoplasmosis, Tubercle, Acinetobacter, Enterococcus*.

In one embodiment, the genus of bacteria include *Mycobacterium*.

In one embodiment, the genera of bacteria include, for example, *Neisseria, Haemophilus, Bacteroides, Chlamydia, Brachyspira pilosicoli, Legionella*, and *Helicobacter*.

In one embodiment, the genera of bacteria include, for example, *Clostridium, Listeria, Staphylococcus*, and *Firmicutes*

In one embodiment, the bacterium is resistant to at least one antibiotic. In one embodiments, bacterium that has at least one point mutation that confers antibiotic resistance. In one embodiment, the bacterium has one or more of the following mutations of one or more amino acids: (1) serine to leucine; (2) histidine to tyrosine; (3) or asparagine to tyrosine. In one embodiment, the bacterium is resistant to rifamycin. In one embodiment, the bacterium is *Staphylococcus aureus, Staphylococcus epidermidis, Listeria monocytogenes Salmonella enterica, Pseudomonas aeruginosa, Proteus mirabills, Enterococcus faecium, Acinetobacter baumannii*, and *Mycobacterium tuberculosis*. In one embodiment, the *S. aureus* carries a mutation in its RNA polymerase (RNAP). In one embodiment, the *S. aureus* RNAP mutation is S447L, H481Y, or D471Y.

In one aspect, the disclosure provides a method of treating or preventing a bacterial infection in a subject. In one embodiment, the method comprises, administering to the subject a composition comprising a compound of the disclosure.

In one embodiment, the subject has a bacterial infection.

In one embodiment, the bacterial infection is resistant to at least one antibiotic treatment. In one embodiments, the bacterial infection is caused by a bacterium that has at least one point mutation that confers antibiotic resistance. In one embodiment, the bacterium has one or more of the following mutations of one or more amino acids: (1) serine to leucine; (2) histidine to tyrosine; (3) or asparagine to tyrosine.

In one embodiment, the bacterial infection is resistant to rifamycin. Examples of rifamycin-resistance can be found in J Antibiot (Tokyo). 2014 September; 67(9):625-30. doi: 10.1038/ja.2014.107. Epub 2014 Aug. 13, which is herein incorporated by reference in its entirety. Examples of methods to identify rifamycin-resistant bacteria include Polymerase chain reaction (e.g., Lancet. 1993 Mar. 13; 341 (8846):647-50, which is herein incorporated by reference in its entirety).

In one embodiment, the bacterial infection is an infection of *Staphylococcus aureus, Staphylococcus epidermidis, Listeria monocytogenes* and *M. tuberculosis*. In one embodiment, the *S. aureus* carries a mutation in its RNA polymerase (RNAP). In one embodiment, the *S. aureus* RNAP mutation is S447L, H481Y, or D471Y.

In one embodiment, the disease or the condition is selected from the group consisting of tuberculosis, *Mycobacterium avium* complex, *Myobacterium leprae*, leprosy, and Legionnaires' disease, methicillin-resistant *Staphylococcus aureus* (MRSA), *Staphylococcus epidermidis, Neisseria meningitidis* (meningococcal) infections, tick-borne pathogens, including *Borrelia burgdorferi* and *Anaplasma phagocytophilum*, infections by *Listeria* species, such as *Neisseria gonorrhoeae, Haemophilus influenzae, Haemophilus influenzae* type b, and *Legionella pneumophila*, primary amoebic meningoencephalitis caused by *Naegleria fowleri, Mycobacterium kansasii*, Pruritus biliary cholangitis, *Chlamydophila pneumonia*, irritable bowel syndrome (IBS), Travelers' Diarrhea caused by *E. coli*, hepatic encephalopathy, infectious diarrhea, small intestinal bacterial overgrowth, diverticular disease, *Chlamydia* infection, *Clostridium difficile* associated diarrhea (CDAD), trachoma, buruli ulcer caused by *Mycobacterium ulcerans*, and gastric ulcer disease caused by *Helicobacter pylori*.

In one embodiment, the bacterium treated with compounds disclosed herein has one or more of the following mutations of one or more amino acids: (1) serine to leucine; (2) histidine to tyrosine; (3) asparagine to tyrosine; (4) aspartic acid to valine; (5) histidine to aspartic acid; (6) aspartic acid to glutamic acid; (7) histidine to asparagine; or (8) serine to tryptophan. Other mutations and mutated bacteria suitable for treatment with the present includes are disclosed in, e.g., "Resistance to rifampicin: a review" (*J. Antibiot* (2014), 67(9), 625-30), MUBII-TB-DB: a database of mutations associated with antibiotic resistance in *Mycobacterium tuberculosis* (BMC Bioinformatics (2014) 15, 107), and the Comprehensive Antibiotic Resistance Database, which are herein incorporated by reference in their entireties for all purposes.

In one embodiment, the point mutation is Ser531Leu. In one embodiment, the point mutation is His526Asn. In one embodiment, the point mutation is Asp516Val. In one embodiment, the point mutation is His526Tyr. In one embodiment, the point mutation is His526Asp. In one embodiment, the point mutation is Asp516Glu. In one embodiment, the point mutation is Ser531Trp.

In one embodiment, the method further comprises administering to the subject an additional therapeutic agent. In one embodiment, the compound of the disclosure and the therapeutic agent are co-administered to the subject. In one embodiment, the compound of the disclosure and the therapeutic agent are co-formulated and co-administered to the subject. In one embodiment, the therapeutic agent is an antibacterial agent or an antiviral agent.

In one embodiment, the subject is a mammal. In another embodiment, the mammal is a human.

In one aspect, the disclosure provides a method of overcoming antibacterial resistance. In one embodiment, the method comprises introducing a methylenedioxy group into an antibacterial compound. For example, in one embodiment, the methylenedioxy forms a bridge on a naphthohydroquinone core. In one embodiment, introducing the methylenedioxy group into an antibacterial compound abrogates resistance to the antibacterial compound.

Methods of determining antibiotic resistance (e.g., resistance to rifamycin) are known in the art. For example, in Brock Biology of Microoganisms, 11th edition (Pearson, 2006) which is herein incorporated by reference in its entirety for all purposes. In one embodiment, the method includes antimicrobial susceptibility testing. In one embodiment, the method is an agar diffusion method. In one embodiment, the method is a tube dilution technique to determine the minimum inhibitory concentration (MIC). In one embodiment, the method includes an antibiotic dilution assay in culture. In one embodiment, the method includes an antibiotic dilution assay in tubes. In one embodiment, the method includes the Kirby-Bauer method.

The "minimum inhibitory concentration" or "MIC" refers to the lowest concentration of an antimicrobial agent that will inhibit the visible growth of a microorganism after overnight (in vitro) incubation. Minimum inhibitory concentrations are important in diagnostic laboratories to confirm resistance of microorganisms to an antimicrobial agent and also to monitor the activity of new antimicrobial agents. The MIC is generally regarded as the most basic laboratory measurement of the activity of an antimicrobial agent against a bacterial organism. Thus, in certain embodiments, the oligomer reduces the minimum inhibitory concentration (MIC) of an antimicrobial agent against the bacteria or bacterium by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone. In certain embodiments, the oligomer reduces the minimum inhibitory concentration (MIC) of an antimicrobial agent against the bacteria or bacterium by about or at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000-fold or more (including all integers and ranges in between), relative to the antimicrobial agent alone. In some embodiments, the bacterium is *Staphylococcus aureus, Staphylococcus epidermidis, Listeria monocytogenes* or *M. tuberculosis*. In some embodiments, the bacterium is *Mycobacterium tuberculosis*.

In some embodiments, a bacterium is considered to be resistant to rifamycin if the MIC of rifamycin is greater than or equal to about 50 µm/mL, e.g., about 60 µm/mL, about 70 µm/mL, about 80 µm/mL, about 90 µm/mL, about 100 µm/mL, about 150 µm/mL, about 200 µm/mL, about 250 µm/mL, about 300 µm/mL, about 350 µm/mL, about 400 µm/mL, about 450 µm/mL, about 500 µm/mL, or more.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses, and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

Administration/Dosing

The regimen of administration may affect what constitutes an effective amount. The therapeutic formulations may be administered to the patient either prior to or after the onset of pathogenic colonization, biofilm formation, and/or infection in a patient. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a patient, preferably a mammal, more preferably a human, may be carried out using known procedures, at dosages and for periods of time effective to prevent, reduce or disrupt pathogenic colonization, biofilm formation, and/or infection in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of breathing control disorders in a patient.

In one embodiment, the compositions of the disclosure are formulated using one or more pharmaceutically acceptable excipients or carriers. In one embodiment, the pharmaceutical compositions of the disclosure comprise a therapeutically effective amount of a compound of the disclosure and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol and sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present disclosure depends on the age, sex and weight of the patient, the current medical condition of the patient and the severity of the disease or infection in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the disclosure for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a compound of the disclosure is from about 1 mg to about 2,500 mg. In some embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compounds for use in the method of the disclosure may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the disclosure are administered to the patient from about one to about five times per day or more. In various embodiments, the compositions of the disclosure are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the disclosure will vary from individual to individual depending on many factors including, but not limited to, age, the disease or disorder to be treated, the severity of the disease or disorder to be treated, gender, overall health, and other factors. Thus, the disclosure should not be construed to be limited to any particular dosing regime and the precise dosage and composition to be administered to any patient is determined by the medical professional taking all other factors about the patient into account.

In the case wherein the patient's status does improve, upon the doctor's discretion the administration of the inhibitor of the disclosure is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the present disclosure is directed to a packaged pharmaceutical composition comprising a container holding a therapeutically effective amount of a compound of the disclosure, alone or in combination with a second pharmaceutical agent; and instructions for using the compound to treat or prevent a disease or infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of Administration

Routes of administration of any of the compositions of the disclosure include oral, nasal, rectal, intravaginal, parenteral, buccal, ophthalmic, intrathecal, sublingual or topical. The compounds for use in the disclosure may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, gels, lotions, oil-in-water or water-in-oil emulsions such as creams, ointments or pastes, and solutions or suspensions. Topically administrable formulations may, for example, comprise from about 1% to about 10% (w/v) active ingredient in a solvent, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide (DMSO), and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the disclosure may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

For oral administration, suitable forms include tablets, dragees, liquids, drops, suppositories, or capsules, caplets and gelcaps. The compositions formulated for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the disclosure may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present disclosure also includes a multi-layer tablet comprising a layer providing for the delayed release of one or more compounds of the disclosure, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

For parenteral administration, the compounds of the disclosure may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional dosage forms of this disclosure include dosage forms as described in U.S. Pat. Nos. 6,340,475; 6,488,962; 6,451,808; 5,972,389; 5,582,837; and 5,007,790. Additional dosage forms of this disclosure also include dosage forms as described in U.S. Patent Applications Nos. 20030147952; 20030104062; 20030104053; 20030044466; 20030039688; and 20020051820. Additional dosage forms of this disclosure also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present disclosure may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the disclosure may be administered in the form of microparticles, for example, by injection or in the form of wafers or discs by implantation.

In one embodiment of the disclosure, the compounds of the disclosure are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

EXPERIMENTAL EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present disclosure and practice the claimed methods. The following working examples therefore, specifically point out the preferred embodiments of the present disclosure, and are not to be construed as limiting in any way the remainder of the disclosure.

Minimum Inhibitory Concentration (MIC) and Minimal Bactericidal Concentration (MBC) Assays. The MIC was measured by the microdilution method of the Clinical and Laboratory Standards Institute (see, e.g., Standards NCfCL. Methods for Dilution-Antimicrobial Susceptibility Tests for Bacteria That Grow Aerobically; M7-A7; Broth Microdilution Method: CLSI, Wayne, Pa., USA, 2006 which is incorporated by reference herein in its entirety). Specifically, overnight cultures in an appropriate broth (e.g., Luria Bertani, Mueller-Hinton II) were diluted to 5×105 cfu/mL and used to fill wells of a 96-well plate. Rifamycin was added to the first well of each row, and a 2-fold dilution series was made by transferring 100 µl from one well to the next. The plates were incubated on a shaker (200 rpm) at 35-37° C. for 18-20 hours, and then the optical density was measured at 595 nm on a microplate reader. Samples of each well without visible growth were diluted and spread on LB agar petri dishes. The petri dishes were incubated overnight at 37° C., and the colonies were counted.

Example 1: Kanglemycin V1 and V2, Rifamycin Congers that are Active Against Rifamycin Resistant Bacteria This study examines whether competition between environmental microbes might have selected for the evolution of rifamycin congeners capable of circumventing common antibiotic resistance mechanisms, including those enriched in clinical settings.

In an effort to understand natural rifamycin biosynthetic diversity the sequencing of soil metagenomes was studied. Soils are believed to be one the richest and the most underexplored reservoirs of bacterial biosynthetic diversity, with each gram of soil containing thousands of unique and previously unstudied bacterial species. With the development of robust sequencing approaches for identifying biosynthetic gene clusters in complex microbiomes, it is now possible to systematically explore soil ecosystems for gene cluster families of interest. It is hypothesized herein that the most biosynthetically complex, rifamycin-like gene clusters found in soil environments would represent nature's most evolved responses to commonly encountered rifamycin resistance mechanisms. While this survey of soil metagenomes revealed a rich diversity in rifamycin biosynthesis, the family of gene clusters containing the largest collection of predicted tailoring genes was of particular interest as they might encode for the most highly functionalized rifamycin congeners.

Numerous examples of this gene cluster family were found in soil metagenomes as well as one example in the sequenced genome of a cultured bacterium. The data presented herein demonstrates the characterization of the new kanglemycin-like rifamycin congeners that are encoded by a member of this tailoring enzyme-rich gene cluster family. Kanglemycin V1 and V2 are active against RNAPs carrying mutations that correspond to those commonly found in rifampicin resistant bacterial pathogens, including rifampicin resistant strains of Mycobacterium tuberculosis. An X-ray co-crystal structure and biochemical studies indicate that, while the kanglemycins bind the same site on RNAP as other rifamycin congeners, they inhibit transcription differently. Taken together these data suggest that kanglemycins V1 and V2 represent new lead structures for the potential development of therapeutics with activity against rifamycin resistant bacteria.

Materials and Methods

Screening Soil Sample for 3-Amino-5-Hydroxy Benzoic Acid (AHBA) Synthase Gene Sequences Environmental DNA (eDNA) was extracted from each soil sample using a modified DNA extraction protocol (Charlop-Powers et al., 2015, Elife, 4: e05048; Brady, 2007, Nat. Protoc., 2:1297-1305, which are incorporated by reference herein in their entireties). Briefly, approximately 25 g of each soil was placed in a 50 mL falcon tube. 30 mL of lysis buffer (100 mM Tris-HCl, 100 mM ethylenediaminetetraacetic acid (EDTA), 1.5 M NaCl, 1% (w/v) cetyl trimethylammonium bromide, 2% (w/v) sodium dodecyl sulfate, pH 8.0) were added to each tube. After a 2-hour incubation at 70° C. with gentle mixing by inversion in 15 min intervals, the tubes were spun down at 5,000×g for 10 min at 4° C. The supernatant was decanted into a clean tube and 0.6 volumes of isopropanol were added to precipitate DNA. Precipitated DNA was pelleted by centrifugation at 5,000×g for 30 min at 4° C. The pellet was washed with 70% ethanol and allowed to air-dry for several hours at room temperature. The dried DNA pellet was resuspended in 500 µL TE (10 mM Tris-HCl, 1 mM EDTA, pH 8.0). The resulting crude eDNA samples were screened with degenerate primers targeting the AHBA synthase gene, rifK: (forward) 5'-CCSGCCTTCACCTTCATCTCCTC-3'(SEQ ID NO:1) and (reverse) 5'-AYCCGGAACATSGC-CATGTAGTG-3'(SEQ ID NO:2) (Wang et al., 2013, J. Appl. Microbiol., 115:77-85, which is incorporated by reference herein in its entirety). These degenerate primers were appended with a collection of distinct 8 bp barcodes (Owen et al., 2013, Proc. Natl. Acad. Sci. USA, 110:11797-11802, which is incorporated by reference herein in its entirety) that were used to distinguish amplicons generated from each soil. All primers were also appended with adapters for Illumina sequencing: 5'-CTACACGACGCTCTTCC-GATCT-3'(SEQ ID NO:3) (forward primer adaptor); 5'—CAGACGTGTGCTCTTCCGATCT-3'(SEQ ID NO:4) (reverse primer adaptor). A typical eDNA PCR reaction contained 1 µL Thermopol master mix (10× stock, New England BioLabs Inc.), 0.1 µL rTaq polymerase (5 units/µL stock; Bulldog Bio), 0.5 µL of each primer (10 µM stock concentration), 2 µL of eDNA and 5.9 µL of water. A touchdown PCR protocol was used for all screening: 5 min at 95° C., followed by 6 cycles of, 30 seconds at 95° C., 30 seconds at 65° C. (−1° C./cycle) and 40 seconds at 72° C., followed by 29 cycles of 30 seconds at 95° C., 30 seconds at 58° C. and 40 seconds at 72° C. PCR reactions were pooled and size selected by electrophoresis using an E-Gel (Invitrogen) prior to sequencing.

Sequencing and Bioinformatics Analysis of AHBA Synthase Gene Amplicons.

Sequencing of pooled amplicons was performed by Illumina MiSeq using 300 bp paired-end reads. The forward reads were trimmed to 240 base pairs, the reverse reads were trimmed to 175 base pairs. The mate-paired reads were concatenated and subsequently clustered at 90% within each soil sample using USEARCH v7 (Edgar et al., 2010, Bioinformatics, 26:2460-2461, which is incorporated by reference herein in its entirety). Single reads were removed and the centroid amplicon sequences were re-clustered at 97% identity across soils. Reference AHBA synthase sequences from published gene clusters were trimmed to the same 240 bp at the 5' end and 175 base pairs from the 3' end as the sequencing reads and combined with the re-clustered centroid amplicon sequences. The combined sequences were aligned with MUSCLE v3.8.31 (Edgar, 2004, Nucleic Acids Res., 32:1792-1797, which is incorporated by reference herein in its entirety) and a phylogenetic tree was constructed using FastTree v2.1.10 (Price et al, 2010, PLoS One, 5:e9490, which is incorporated by reference herein in its entirety). The phylogenetic tree of AHBA amplicons from crude soils and reference sequences was examined for sub-clades containing sequences more closely related to rifamycin AHBA synthases sequence than to AHBA synthase genes from other ansamycin gene clusters.

Library Construction, Arraying and Sequencing to Identify Clones Containing AHBA Synthase Genes Metagenomic cosmid library construction was performed as previously described (Brady, 2007, Nat. Protoc., 2:1297-12305, which is incorporated by reference herein in its entirety). Each newly constructed metagenomic library contains 10-60 million individual cosmid clones with ~30-45 kb of eDNA inserts. Each library was constructed as 768 sub-pools (2×384 wells) containing 25-60 thousand unique cosmids clones per pool. Sub-pools were stored both as glycerol stocks to facilitate the recovery of individual cosmids of interest and as purified cosmid DNA to facilitate PCR-based screening. To identify sub-pools from which AHBA synthase containing clones could be recovered, cosmid DNA from each pool served as template in PCR reactions with the same degenerate primers that were used to screen eDNA. The resulting PCR amplicons were gel purified and Sanger sequenced to identify sub-pools with ABHA synthase gene containing cosmids. Cosmid clones containing AHBA synthase genes were recovered from ABHA synthase amplicon positive sub-library pools using dilution PCR as previously described (Owen et al, 2015, Proc. Natl. Acad. Sci. USA, 112:4221-4226). Cosmids were sequenced using ion PGM technology and reads were assembled into contigs using Newbler (Zhang et al., 2012, BMC Research Notes, 5:567). All contigs were analyzed using open reading frame (ORF) predictions from MetaGeneMark (Zhu et al., 2010, Nucleic Acids Research, 38:e132, which is incorporated by reference herein in its entirety) and BLAST (Altschul et al., 1990, Journal of Molecular Biology, 215:403-410, which is incorporated by reference herein in its entirety). Putative functions for new tailoring enzymes were assigned based on the predicted function of close relatives identified by Blast search.

Recovery of Sets of Clones Constituting Complete Gene Clusters and

Bioinformatic Analysis of Recovered Tailoring Genes

To recover of overlapping cosmids containing polyketide synthase (PKS) and tailoring regions associated with the recovered AHBA synthase genes, DNA from library sub-pools was screened with degenerate primers targeting two additional conserved sequences in rifamycin biosynthesis: ketosynthase (KS) domains and post-PKS tailoring genes rif15A/15B. In known rifamycin congener gene clusters the PKS region resides directly upstream (5') of ABHA biosynthesis operon. The rif15A/15B genes, which are predicted to encode subunits of a transketolase are generally found at the very downstream (3') edge of the tailoring region of a rifamycin congener gene cluster. The primers used for targeting the KS domains were: 5'-ATCGAGGCSCAGGC-SYTG-3' (SEQ ID NO:5) (forward) and 5'-GAY-SASGTGSGCGTTSGT-3' (SEQ ID NO: 6) (reverse). These primers were appended with adaptors for Ion Torrent Personal Genome Machine (PGM) System sequencing: 5'-CCATCTCATCCCTGCGTGTCTCCGACTCAG3-3' (SEQ ID NO:7) (forward primer adaptor) and 5'-CCTCTC-TATGGGCAGTCGGTGAT-3' (SEQ ID NO: 8) (reverse primer adaptor). The primers used for targeting the rif15A/B genes were: 5'-CCGGTTCTAYCTSTCCAAG-3' (SEQ ID NO:9) (forward) and 5'-AASRACCACGASGAGATGT-3' (SEQ ID NO:10) (reverse). These primers were appended the same Illumina adaptors as were use with AHBA synthase primers. As with the AHBA synthase primers, each set of KS and rif15A/15B degenerate primers was also appended with well-specific 8 base pairs barcodes (Owen et al., 2013, Proc. Natl. Acad. Sci. USA, 110:11797-11802, which is incorporated by reference herein in its entirety). The same PCR conditions used for AHBA synthase screening were used for KS and rif15A/15B screening. Amplicons were sequenced using Ion Torrent PGM (KS amplicons) or Illumina MiSeq (rif15A/15B amplicons) technologies. 300 base pair paired-end reads were processed as described for AHBA synthase amplicons. Tracking the co-localization of rifamycin-like KS, AHBA synthase and rif15A/15B sequences across library sub-pools allowed for the identification of clones that overlapped with the AHBA synthase containing clones that were initially sequenced and thereby recover sets of overlapping cosmids that comprise complete biosynthetic gene clusters. Overlapping sequences were then assembled into larger contigs to create full gene clusters. For phylogenetic analyses of predicted tailoring genes, genes were extracted from all sequenced eDNA tailoring regions as well as tailoring regions from rifamycin gene clusters found in GenBank. Tailoring gene were grouped according to predicted functional class (e.g., glycosyltransferase genes, cytochrome P450 genes, etc.) and aligned with MUSCLE v3.8.31 (Edgar et al., 2004, Nucleic Acids Res., 32:1792-1797, which is incorporated by reference herein in its entirety). A phylogenetic tree was constructed for each functional class using FastTree v2.1.10 (Price et al, 2010, PLoS One, 5:e9490, which is incorporated by reference herein in its entirety).

*Amycolatopsis Vancoresmycina* Fermentation

A spore stock of *A. vancoresmycina* (NRRL B-24208) was created from cultures grown on MS plates (20 g/L mannitol, 20 g/L soya flour and 20 g/L agar) (Kieser et al., 2000, *Practical Streptomyces Genetics*. John Innes Foundation: Norwich, UK; p 613, which is incorporated by reference herein in its entirety). Spores were stored frozen at −20° C. in 20% glycerol. For metabolite production, 5 µL of a glycerol spore stock was used to inoculate 50 mL TSB media (Oxoid) in 125 mL baffled Erlenmeyer flasks, which were shaken at 30° C. and 230 rpm. The following day, 200 µL of the overnight TSB starter culture was used to inoculate 50 mL of $R_5A$ media (Fernandez et al., 1998, J. Bacteriol., 180:4929-4937, which is incorporated by reference herein in its entirety) (100 g/L sucrose, 0.25 g/L K2S04, 10.12 g/L $MgCl_2*6H_2O$, 10 g/L glucose, 0.1 g/L casamino acids, 20.5 g/L MOPS, 5 g/L yeast extract and 2 g/L NaOH) in 125 mL baffled Erlenmeyer flasks. As the metabolite production profile and yield were found to respond favorably to increased aeration, a 1"×1" stainless steel metal mesh was added to each flask. Flasks were grown for 6 days at 30° C. and 200 rpm.

Isolation of Kanglemycins a, V1 and V2

After 6 days of shaking, flasks were combined and extracted using a 2:1 ratio of neutral ethyl acetate. The resulting crude extract was fractionated by flash chromatography (RediSep Rf, High Performance Gold 50 g HP C18 resin) using a linear gradient of 30-100% acetonitrile:water with 0.1% acetic acid over 30 min. The column elution was monitored by UV and fractions containing a strong absorbance at both 254 nm and 420 nm were pooled. Pooled fractions were diluted with four volumes of $H_2O$ and loaded onto a solid phase extraction column (Grace Biosciences). After binding and washing with $H_2O$, the column was eluted with methanol. The kanglemycins were then purified by HPLC using a 10 mm×150 mm Cis column (Waters) and an isocratic method of 46% acetonitrile with 0.1% formic acid at a flow rate of 3.14 mL/min. The compounds eluted with retention times of 38 min (kanglemycin A), 43 min (kanglemycin V2) and 50 min (kanglemycin V1). Typical yields of purified kanglemycin A, V1 and V2 were 0.3 mg, 0.4 mg and 0.1 mg, respectively, per liter of culture.

Structure Elucidation of Kanglemycins a, V1 and V2

NMR studies for kanglemycin A and V1 were performed at room temperature on a Bruker Avance 600 MHz NMR equipped with a TCI triple resonance cryoprobe. Spectra for kanglemycin A and V1 were collected in methylene chloride and deuterated methanol, respectively. Kanglemycin V2 exhibited broad peaks in all common NMR solvents when data were collected at room temperature. The peaks were considerably sharper at lower temperatures. The final dataset for kanglemycin V2 was collected deuterated methanol at −20° C. on a Bruker AvanceHD 500 MHz NMR equipped with a TCI cryoprobe with enhanced $H^1/F^{19}$ and $C^{13}$ detection and low temperature (−40° C.) capabilities (Weill Cornell Medicine NMR Core). HRMS analysis was performed at Memorial Sloan-Kettering Cancer Center using an LCT Premier XE system (Waters).

Antibiotic Assays Against *Staphyloccocus aureus*

Figure 27:
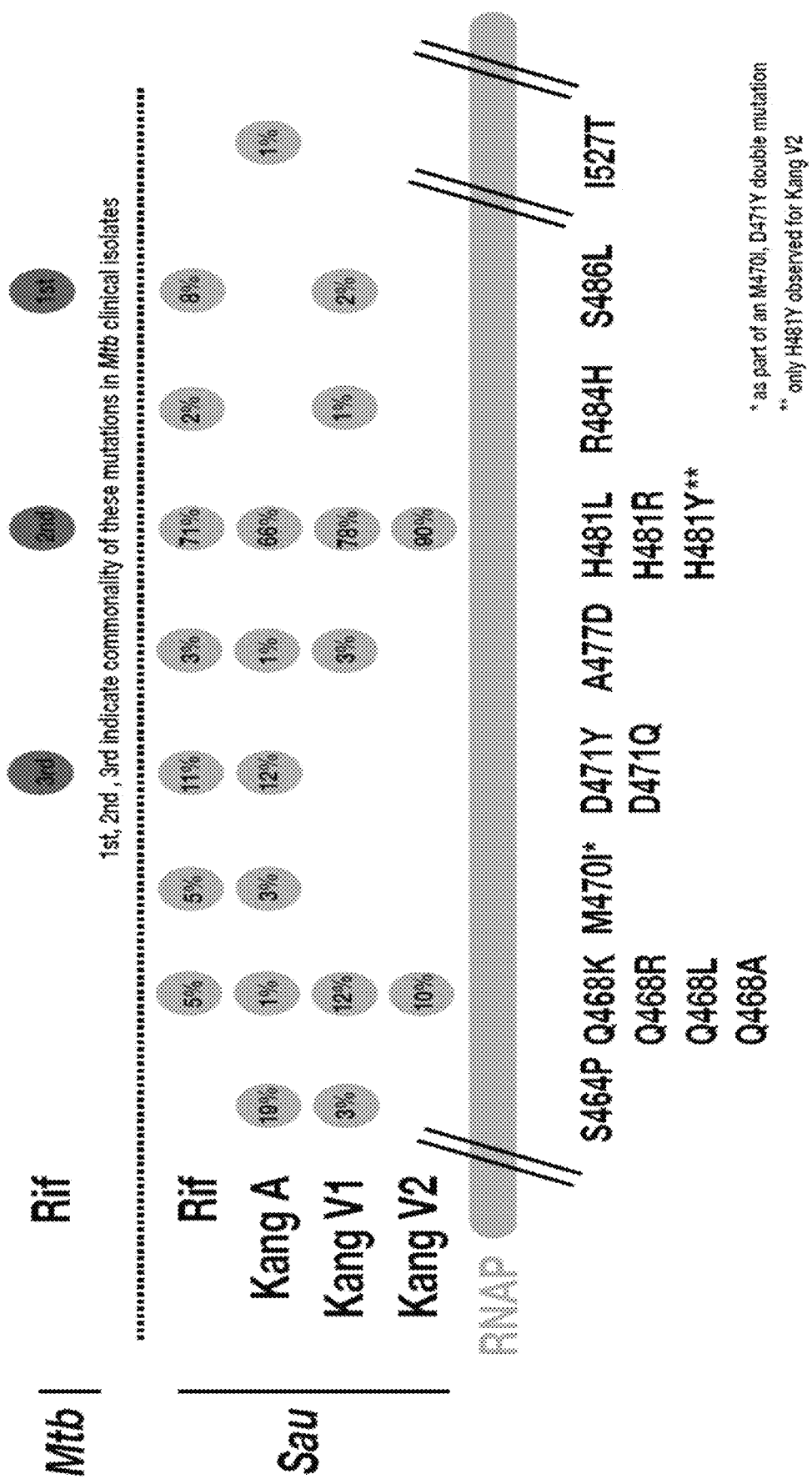
FIG. 27 depicts rpoB gene with the three most commonly mutated sites in RifRMtb indicated with red circles. $Rif^R$ and $Kang^R$ mutations identified in S. aureus and their frequency are indicated with blue circles.

Minimum inhibitory concentration (MIC) assays were performed by incubating cells against a serial 1:3 dilution of compounds starting at 50 g/mL. Briefly, a single colony of wild type *S. aureus* ATCC 12600 or *S. aureus* ATCC 12600 carrying either a D471Y, H481Y, or S486L mutation (FIG. 27; Srivastava et al, 2012, Antimicrob. Agents, 56:6250-6255, which is incorporated by reference herein in its entirety) was used to inoculate 7 mL of Luria-Bertani (LB) broth and the culture was grown overnight to saturation. The following day, 10 µL of overnight culture were diluted into 50 mL of LB broth and 80 µL aliquots were distributed to each well of a 96-well plate. 250 µg of dried test compound was re-suspended in 50 µL of methanol and diluted to 250 µg/mL with LB. Starting with 250 µg/mL of antibiotic in the first well, a 1:3 serial dilution of the was performed in LB across the plate. No compound was added to the final well in each row. 20 µL of diluted test compound were transferred, in triplicate, to the wells of a plate containing an assay strain. This yielded the final volume of 100 µL in assay wells, with the initial concentration of compound being 50 µg/mL. Plates were sealed with air permeable membranes (BreathEasy) and incubated at 30° C., with shaking at 200 rpm for 24 hrs. The $OD_{600}$ of each plate was read at 24 hr using an Epoch Microplate Spectrophotometer (BioTek Instrumetns) and MIC values were reported as the lowest concentration of the compound that inhibited the growth of the test strain.

Antibiotic Assays Against *Mycobacterium tuberculosis*

*M. tuberculosis* H37Rv was passaged in Middlebrook 7H9 media (BD Biosciences) supplemented with oleic acid-albumin-dextrose-catalase (OADC; BD Biosciences) and 0.02% tyloxapol (hereafter called 7H9 complete). Replicating conditions were prepared as previously described (Gold et al, 2015, Antimicrob. Agents Chemother., 59:6521-6538, which is incorporated by reference herein in its entirety). All compounds were reconstituted in dimethyl sulfoxide (DMSO) and serial dilutions were created in 96-well microplates. Mid-log phase *M. tuberculosis* was diluted to an $OD_{580}$ of 0.01 with 7H9 complete and 198 µL were distributed in 96-well microplates. 2 µL of the compound dilutions were added to the culture wells in triplicate rows, keeping the DMSO concentration at 1%. DMSO and rifampin controls were included in every experiment. Plates were incubated at 37° C. with room air oxygen and 5% $CO_2$. $IC_{90}$ values were determined using an M5 SpectraMax Microplate reader (Molecular Devices) at $OD_{580}$ between day 10 and 14 after thorough mixing of the wells.

Transcription assay Recombinantly produced wild-type and S447L mutant DNA-dependent RNA polymerase from *Mycobacterium smegmatis* was purified as previously described (Hubin et al, 2017, ElifeElife 2017, 6:e22520, which is incorporated by reference herein in its entirety). To generate the holoenzyme, the RNAP core was incubated with 5.0 equivalents of sigma/RbpA for 15 minutes at 37° C. The transcription assay was performed in 20 µL volumes. 50 nM of the wild-type or mutant RNAP holoenzyme in transcription buffer (10 mM Tris HCl, pH 7.9, 50 mM KCl, 10 mM, MgCl2, 1 mM 1,4-dithiothreitol (DTT), 5 µg/mL bovine serum albumin (BSA) and 0.1 mM EDTA) was mixed with kanglemycins A, V1, or V2, or with rifampicin, at different concentrations of antibiotic. To allow binding of the antibiotics to the RNAP, the mixtures were incubated at 37° C. for 5 min. Following incubation, 10 mM of AP3 promoter (Gonzalez-y-Merchand et al, 1996, Microbiology, 142:667-674, which is incorporated by reference herein in its entirety) was added to each tube and the samples were incubated for an additional 15 min at 37° C. to allow formation of the RNAP open complex. Transcription was initiated by the addition of a nucleotide mixture consisting of 200 µM ATP, 200 µM CTP, 200 µM GTP, 50 µM unlabeled UTP and 50 µM gamma-P32-labelled UTP. Each reaction was allowed to proceed for 15 min at 37° C. before the addition of 20 µL of stop buffer (0.5×TBE, pH 8.3, 8 M urea, 30 mM EDTA, 0.05% bromophenol blue and 0.05% xylene cyanol). Reactions were heated to 95° C. for 10 min and loaded onto a polyacrylamide gel (23% Acrylamide/Bis acrylamide (19:1), 6M urea and 1×TBE, pH 8.3). Gels were run for 3 hours at 500 V, then exposed on a phosphoroimaging plate (GE Healthcare) for 12 hours before being imaged using a Typhoon 9400 Variable Imager (Amersham Biosciences).

Metagenomic Survey of Rifamycin Biosynthetic Diversity

The complexity of soil microbiomes has limited the utility of shotgun sequencing as a tool for identifying biosynthetic gene clusters in soil metagenomes. PCR-based methods using degenerate primers to target conserved natural product biosynthetic genes have been developed to study biosynthetic gene cluster diversity present in an environmental sample, much in the same way that bacterial phylogenetic diversity is routinely assessed through the analysis of PCR-amplified 16S genes (Charlop-Powers et al, 2015, Elife, 4:e05048; Kang et al., 2014, ACS Chem. Biol., 9:1267-1272; Owen et al., 2015, Proc. Natl. Acad. Sci. USA, 112:4421-4226; Owen et al., 2013, Proc. Natl. Acad. Sci. USA, 110:11797-11802; Reddy, et al., 2012, Appl. Environ. Microbiol., 78:3744-3752, which are incorporated by reference herein in their entireties). To assess the diversity of rifamycin-like gene clusters present in soil microbiomes, degenerate primers targeting the 3-amino-5-hydroxy benzoic acid (AHBA) synthase gene, which encodes the final step in AHBA biosynthesis, were used. AHBA is the universal precursor for the ansamycin family of natural products into which the rifamycins fall (Floss et al., 2011, J. Antibiot. (Tokyo), 64:35-44, which is incorporated by reference herein in its entirety). The phylogenetic divergence of AHBA synthase genes correlates closely with the structural divergence of the metabolites encoded by the biosynthetic gene clusters from which AHBA synthase genes arise, making the AHBA synthase gene an information-rich target for identifying rifamycin gene clusters in metagenomes using PCR-based methods (FIG. 1) (Wang et al, 2013, J. Appl. Microbiol., 115:77-85; Huitu et al, 2009, J. Appl. Microbiol., 106:755-763; Wood et al, 2007, J. Appl. MIcrobiol., 102: 245-253; Zhu et al., 2009, Curr. Microbiol., 58:87-94; Everest et al., 2011, J. Appl. Microbiol., 111:300-311, which are incorporated by reference herein in their entireties).

To identify metagenomes containing rifamycin-like biosynthetic gene clusters, environmental DNA (eDNA) isolated from a collection of approximately 1,500 geographically and ecologically diverse soils was used as the template in PCR reactions with degenerate primers designed to amplify the AHBA synthase genes (FIG. 2A). Amplicon sequences generated from each soil were then compared to a reference collection of AHBA synthase genes from characterized ansamycin biosynthetic gene clusters. A soil was considered a potential source of a rifamycin-like gene cluster if it contained an AHBA synthase sequence that was more closely related to a gene from a known rifamycin-like gene cluster than from any other ansamycin gene cluster. Based on this analysis, rifamycin-like biosynthetic gene clusters were present in approximately half of the soils that were examined. AHBA synthase amplicons within the rifamycin-like sequence-space form a number of well-defined clades (FIG. 2A), which it is predicted might arise from groups of biosynthetic gene clusters encoding structurally distinct congeners. To access potentially new rifamycin-like gene clusters from soil metagenomes, saturating cosmid-based metagenomic libraries were constructed from seven soils, all of which yielded multiple distinct AHBA synthase sequences, suggesting the presence of multiple rifamycin-like gene clusters. In total, this small subset of soils was predicted to contain AHBA synthase sequences from all of the major rifamycin-like clades that were identified. Each metagenomic library was expanded to contain >20,000,000 unique eDNA cosmids and formatted as smaller sub-pools of between 20 and 60 thousand unique cosmid clones per pool to facilitate screening and individual clone recovery.

Rifamycin-Like Gene Clusters from Metagenomic Libraries

In known biosynthetic gene clusters encoding rifamycin family members, a variable region containing tailoring genes responsible for generating most of the structural diversity seen in rifamycin congeners resides directly upstream to the AHBA biosynthesis operon (FIG. 1). To guide the isolation of eDNA cosmids containing tailoring genes, the seven newly constructed and two pre-existing soil eDNA libraries were screened with the same degenerate primers for AHBA synthase that were used to screen crude eDNA extracts (FIG. 2A). Initially, 35 unique cosmids containing AHBA synthase genes (i.e., primary clones) were recovered from sub-library pools that yielded rifamycin-like AHBA sequences (FIG. 2B). Sequencing of these cosmids revealed that variations in the collections of predicted tailoring genes present on these clones largely changed in concert with the phylogenetic divergence of the AHBA synthase genes. Then, sets of overlapping cosmid clones were recovered that completed representative gene clusters associated with distinct collection of tailoring genes found on the primary clones.

Figure 3:
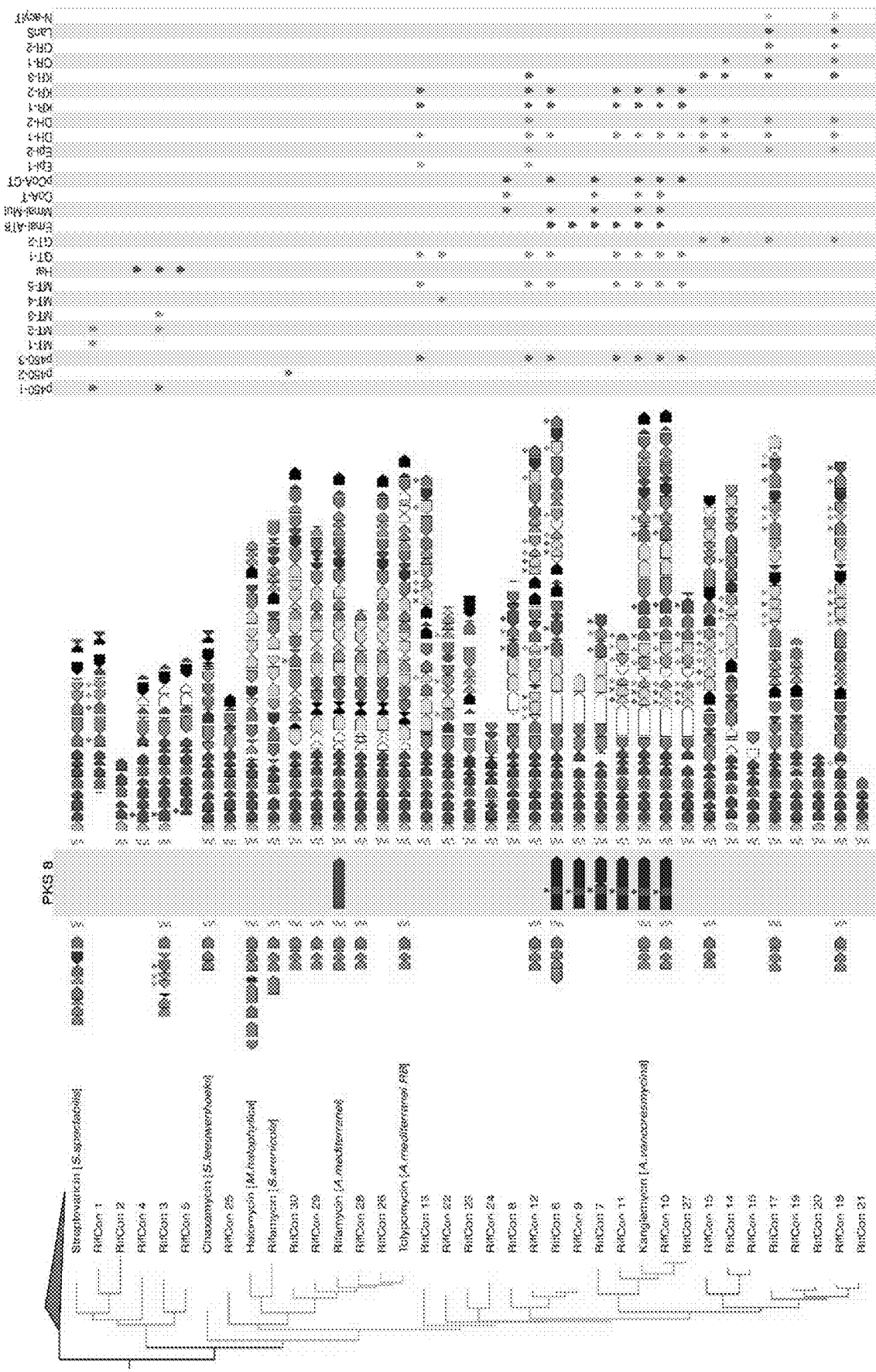
FIG. 3 depicts a summary of tailoring gene content of rifamycin family gene clusters recovered from soil metagenomes. Tailoring genes that are absent or phylogenetically distinct (based on the phylogenies in shown in FIGS. 4A-C, 5A-B, 11A-B) from the prototypical rifamycin gene cluster from Amycolatopsis mediterranei are indicated in the table on the right. Previously characterized rifamycin family gene clusters are shown for reference. PKS modules, with the exception of the eighth module, which shows significant functional differences, are omitted for simplicity.
Figure 5A:
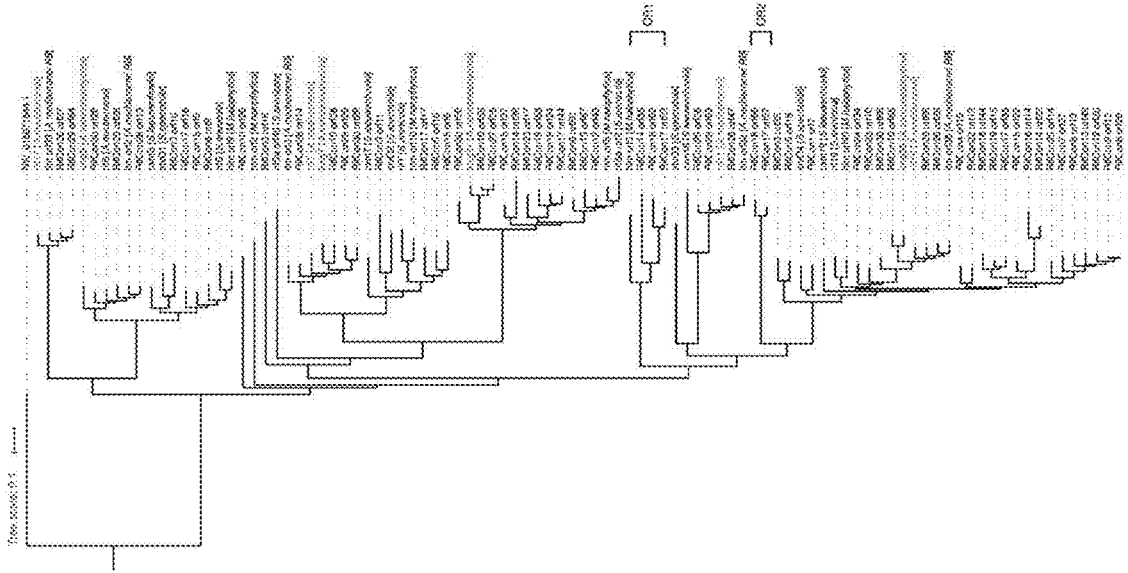
FIG. 5A and FIG. 5B, depicts tailoring genes that are predicted to encode enzymes that are phylogenetically distinct from those found in known rifamycin-like gene clusters.
Figure 5B:
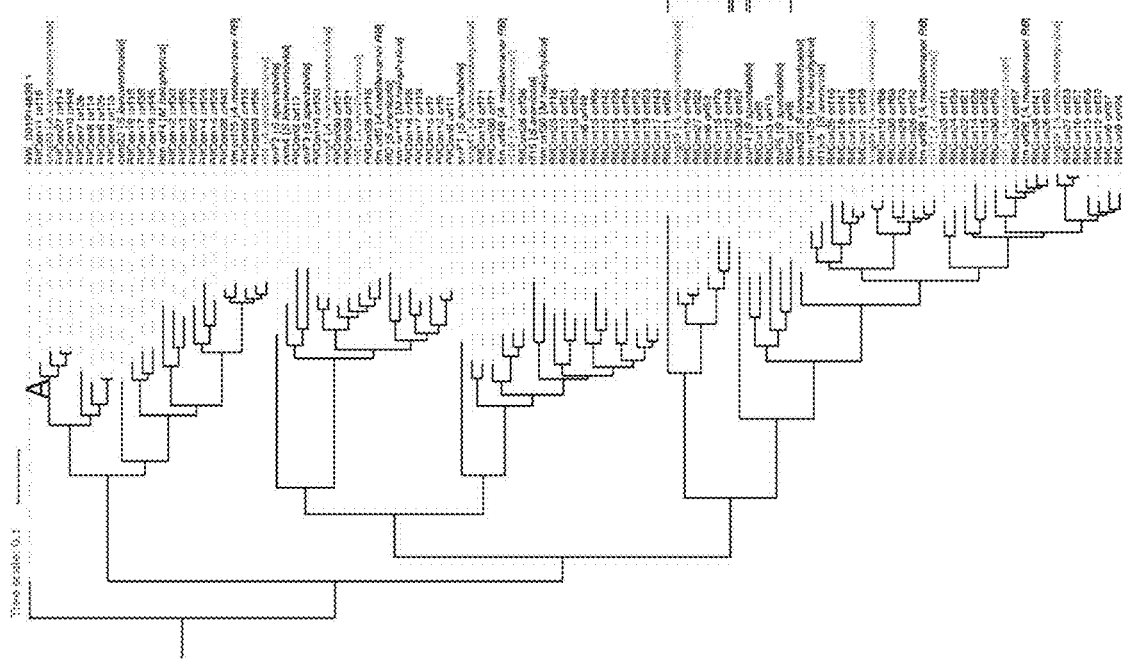

Each collection of overlapping cosmids was sequenced, assembled into a single continuous stretch of DNA and annotated in silico to reveal an eDNA-derived rifamycin-like gene cluster. In addition to the tailoring genes found in previously characterized rifamycin gene clusters, this collection of eDNA-derived gene clusters contained tailoring genes that differ from those found in known rifamycin family gene clusters (FIG. 2B and FIG. 3). This includes genes that are predicted to encode enzymes that have not previously been associated with rifamycin congener biosynthesis (e.g., N-acyltransferases, CoA-transferases, propionyl-CoA carboxylases, methylmalonyl-CoA mutases and lanthionine synthetase-like enzymes). Other tailoring genes are predicted to encode enzymes that are phylogenetically distinct from those found in known rifamycin-like gene clusters (e.g., methyltransferases, glycosyltransferases, cytochrome P450s and oxidoreductases), suggesting they may differentially functionalize the rifamycin backbone (FIG. 4A-C, FIG. 5A-B, FIG. 11A-B).

Figures 6A, 6B, 6C, 6D, 6E:
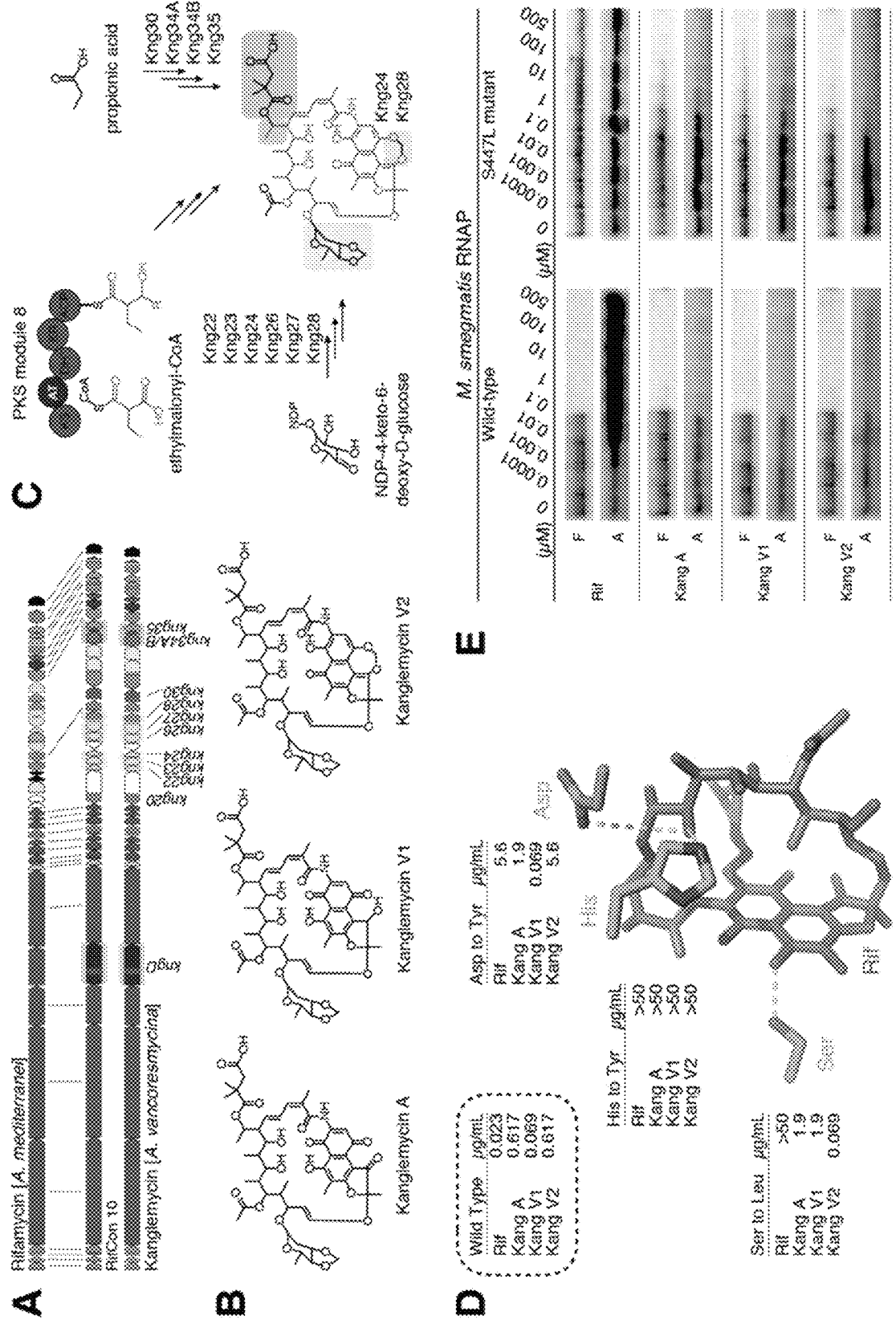
FIG. 6A through FIG. 6E, depicts the structures, biosynthesis, and in vivo and in vitro activities of the kanglemycins.

Interestingly, while the PKS portion of each gene cluster is largely predicted to be functionally identical, a number of gene clusters with the most complex sets of tailoring genes were predicted to encode a change in the substrate specificity of the acyltransferase (AT) domain in the eighth PKS module (AT8*; FIG. 2B). These AT8* domains are predicted to use ethylmalonyl-CoA (Emal) as a substrate instead of methylmalonyl-CoA (Mmal), which would introduce a two-carbon branch into the rifamycin polyketide core. The combination of a potential change in the core polyketide structure and a complex collection of tailoring genes led to the prioritization of this family of gene clusters for investigation. It is hypothesized that these clusters would encode the most complex rifamycin congeners to have evolved to date and that this increased complexity might have evolved in response to common rifamycin resistance mechanisms. Based on AHBA synthase phylogeny, 13% of the rifamycin-like AHBA synthase sequences amplified from soil environments are predicted to arise from this family of gene clusters (FIG. 2A, orange colored clades). While the screening suggests this is a common class of gene clusters in the environment, a search of all publically available sequenced bacterial genomes only revealed one previously uncharacterized gene cluster that contains a similarly complex tailoring gene region and an AT8* domain. This gene cluster from *Amycolatopsis vancoresmycina* is identical in gene content and organization to the RifCon 10 gene cluster that was recovered from a soil eDNA library (FIG. 6A, Table 1).

TABLE 1

Gene annotations for the metagenomic gene cluster RifCon10 and corresponding genes from the *Amycolatopsis vancoresmycina* kanglemycin cluster.

| Gene Name | Length [aa] | Putative Function [Homolog Sp.] | % id/% sm | Accession | A. vanc. homolog (% id/% sm) |
|---|---|---|---|---|---|
| orf26/27 | 54 | gfo/Idh/MocA family oxidoreductase [*A. vancoresmycina*] | 88/91 | WP_051767688.1 | kngS (88/91) |
| orf28 | 259 | gfo/Idh/MocA family oxidoreductase [*A. kentuckyensis*] | 85/91 | WP_086842324.1 | kngT (85/90) |
| orf29 | 71 | hypothetical protein [*A. tolypomycina*] | 97/98 | WP_091304002.1 | kng35 (87/90) |
| orf30 | 396 | cytochrome P450 [*A. vancoresmycina*] | 97/97 | WP_003060232.1 | kngR0 (97/97) |
| orf31/32 | 2412 | polyketide synthase [*A. vancoresmycina*] | 91/93 | WP_003060229.1 | kngA (91/93) |
| orf33/34 | 2148 | polyketide synthase [*A. vancoresmycina*] | 90/94 | WP_033261454.1 | kngB (90/94) |
| orf35 | 1807 | polyketide synthase [*A. vancoresmycina*] | 91/93 | WP_081911206.1 | kngC (91/93) |
| orf36 | 1822 | polyketide synthase [*A. vancoresmycina*] | 94/95 | WP_003102381.1 | kngD (94/95) |
| orf37 | 3449 | polyketide synthase [*A. vancoresmycina*] | 93/95 | WP_033261452.1 | kngE (93/95) |
| orf38 | 261 | N-acetyltransferase/amide synthase [*A. vancoresmycina*] | 93/95 | WP_004559807.1 | kngF (93/95) |
| orf39 | 62 | hypothetical protein [*A. vancoresmycina*] | 89/93 | WP_004559806.1 | kngR1 (89/93) |
| orf40 | 351 | aminoDHQ synthase [*A. vancoresmycina*] | 94/96 | WP_004559805.1 | kngG (94/96) |
| orf41 | 418 | aminoDAHP [*A. vancoresmycina*] | 94/96 | WP_004559804.1 | kngH (94/96) |
| orf42 | 262 | shikimate dehydrogenase [*A. vancoresmycina*] | 92/94 | WP_081911200.1 | kngI (92/94) |
| orf43 | 66 | tripartite tricarboxylate transporter substrate binding protein [Curvibacter sp. GWA2_64_110] | 39/54 | WP_053245989.1 | — |
| orf44 | 386 | AHBA synthase [*A. vancoresmycina*] | 98/99 | WP_003062304.1 | kngK (98/99) |
| orf45 | 357 | gfo/Idh/MocA family oxidoreductase [*A. vancoresmycina*] | 94/96 | WP_033261451.1 | kngL (94/96) |
| orf46 | 232 | phosphoglycolate phosphatase [*A. vancoresmycina*] | 98/100 | WP_003062302.1 | kngM (98/100) |
| orf47 | 298 | kanosamine kinase [*A. vancoresmycina*] | 84/90 | WP_003062299.1 | kngN (84/90) |
| orf48 | 398 | cytochrome P450 [*A. vancoresmycina*] | 97/98 | WP_003062297.1 | kngR4 (97/98) |
| orf49 | 1058 | hypothetical protein [*A. vancoresmycina*] | 95/96 | WP_051767686.1 | kng2 (95/96) |
| orf50 | 253 | NDP-hexose4-ketoreductase [*A. vancoresmycina*] | 95/96 | WP_004562644.1 | kng3 (95/96) |
| orf51 | 355 | aldo/keto reductase [*A. vancoresmycina*] | 95/96 | WP_004562643.1 | kng4 (95/96) |
| orf52 | 255 | NDP-hexose 3-O-methyltransferase [*A. vancoresmycina*] | 96/98 | WP_004562642.1 | kng6 (96/98) |
| orf53 | 324 | stationary phase survival protein SurE [*A. vancoresmycina*] | 93/96 | WP_004562641.1 | kng7 (93/96) |
| orf54 | 383 | hypothetical protein [*A. vancoresmycina*] | 94/96 | WP_004562640.1 | kngR7 (94/96) |
| orf55 | 474 | NDP-hexose 2,3-dehydratase [*A. vancoresmycina*] | 98/99 | WP_004562638.1 | kngR18 (98/99) |
| orf56 | 378 | cytochrome P450 [*A. vancoresmycina*] | 98/100 | WP_004562636.1 | kng10 (98/100) |

TABLE 1-continued

Gene annotations for the metagenomic gene cluster RifCon10 and corresponding genes from the *Amycolatopsis vancoresmycina* kanglemycin cluster.

| Gene Name | Length [aa] | Putative Function [Homolog Sp.] | % id/% sm | Accession | A. vanc. homolog (% id/% sm) |
|---|---|---|---|---|---|
| orf57 | 421 | cytochrome P450 [*A. vancoresmycina*] | 97/98 | WP_004562634.1 | kngR5 (97/98) |
| orf58 | 531 | acyl-CoA carboxylase subunit beta [*A. vancoresmycina*] | 97/98 | WP_004562633.1 | kngI1 (97/98) |
| orf59 | 665 | copper oxidase [*A. vancoresmycina*] | 92/95 | WP_081911204.1 | kngI2 (92/95) |
| orf60 | 576 | ABC transporter ATP-binding protein [*A. vancoresmycina*] | 94/97 | WP_051767685.1 | kngI4 (94/97) |
| orf61 | 594 | ABCtransporter ATP-binding protein [*A. vancoresmycina*] | 96/98 | WP_003071800.1 | kngI7 (96/98) |
| orf62 | 525 | methylmalonyl-CoA mutase [*A. vancoresmycina*] | 98/99 | WP_033261449.1 | kngI8A (98/99) |
| orf63 | 131 | cobalamin B12-binding domain-containing protein [*A. vancoresmycina*] | 98/99 | WP_003071791.1 | kngI8B (98/99) |
| orf64 | 344 | CoA transferase [*A. vancoresmycina*] | 96/97 | WP_003071788.1 | kng21 (96/97) |
| orf65 | 485 | 3-(3-hydroxyphenyl) propionate hydroxylase [*A. vancoresmycina*] | 92/96 | WP_003071786.1 | kngR19 (92/96) |
| orf66 | 392 | acyltransferase [*A. vancoresmycina*] | 95/97 | WP_033261516.1 | kngR20 (95/97) |
| orf67 | 249 | thioesterase [*A. vancoresmycina*] | 92/95 | WP_003071782.1 | kngR (92/95) |
| orf68 | 422 | cytochrome P450 [*A. vancoresmycina*] | 98/100 | WP_003071780.1 | kngR13 (98/100) |
| orf69 | 231 | transketolase [*A. vancoresmycina*] | 98/99 | WP_003071778.1 | kngR15A (98/99) |
| orf70 | 303 | transketolase [*A. vancoresmycina*] | 98/98 | WP_003071776.1 | kngR15B (98/98) |
| orf71 | 419 | cytochrome P450 [*A. vancoresmycina*] | 97/98 | WP_003071775.1 | kngR16 (97/98) |
| orf72 | 149 | aminoDHQ synthase [*A. vancoresmycina*] | 95/96 | WP_003071773.1 | kngJ (95/96) |
| orf73 | 449 | LuxR family transcriptional regulator [*A. vancoresmycina*] | 94/97 | WP_003071771.1 | kngR36 (94/97) |

Rifalogs from an AT8* Gene Cluster

Figures 7A, 7B, 7C, 7D:
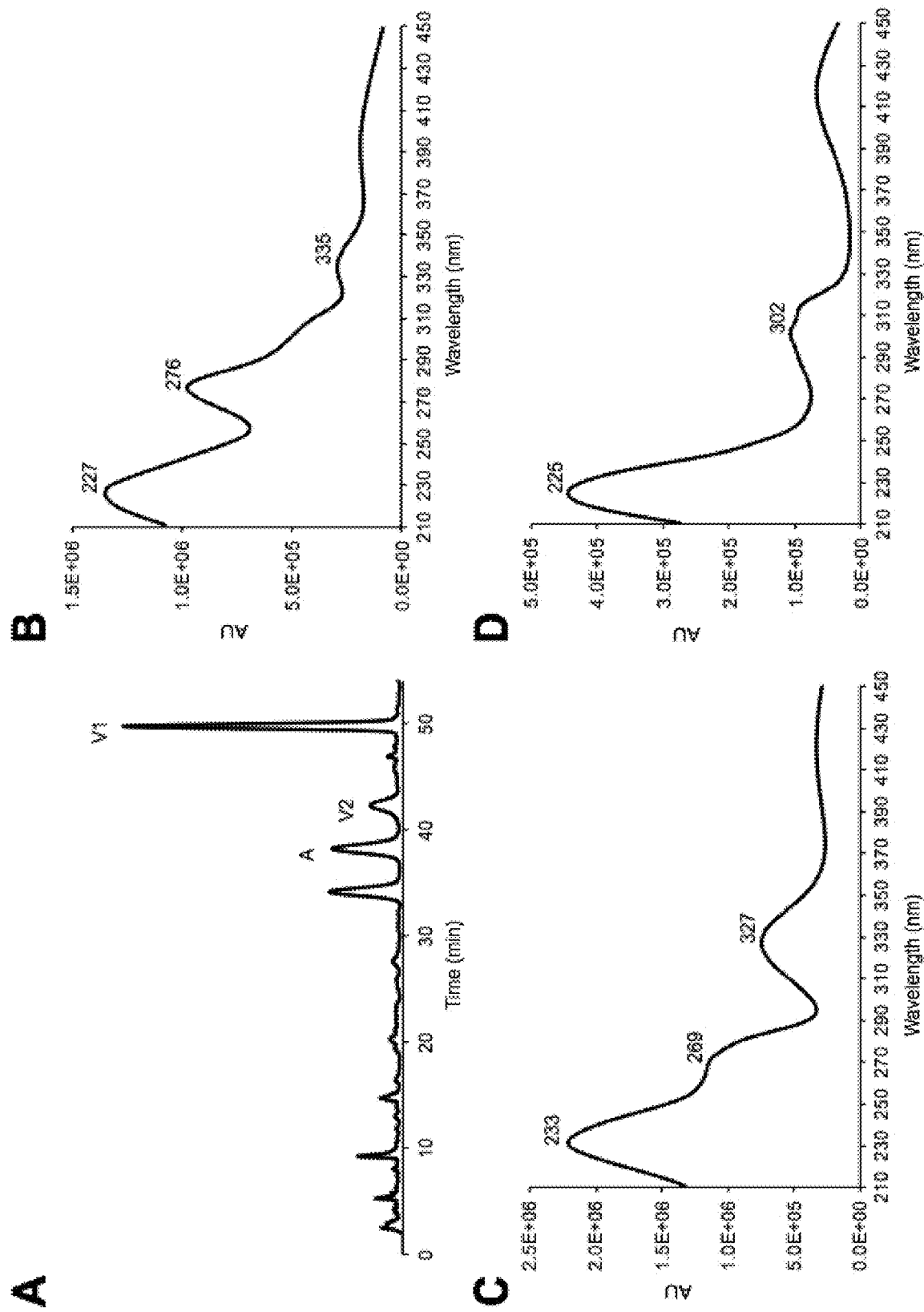
FIG. 7A through FIG. 7D, depicts HPLC analysis of the C-18 flash column fraction containing kanglemycins.

As an initial exploration of the tailoring gene-rich family of gene clusters that contain an AT8* domain, rifalogs were looked for in ethyl acetate extracts from cultures of *A. vancoresmycina*. While *A. vancoresmycina* has never been reported to produce rifamycin-like metabolites, three HPLC peaks with rifamycin-like UV spectra were identified in culture broth extracts (FIG. 7). The structure of each metabolite was elucidated using a combination of HRMS, 1 and 2D NMR and UV data (FIGS. 7-18 and Tables 2-3). Analytical data for compound 1 is consistent with the structure of kanglemycin A, a rifamycin congener originally characterized from *Amycolatopsis mediterranei* var. *kanglensis* and encoded by an uncharacterized gene cluster (Wang et al., 1988, J. Antibiot. (Tokyo), 41:264-267, which is incorporated by reference hereinin its entirety). The most dramatic differences between kanglemycin A and other rifamycin congeners are that it contains a beta-O-3,4-O,O'-methylene digitoxose deoxysugar substituent at C-27, an oxidized ethyl substituent in place of a methyl substituent at C-20 and a gem-dimethyl succinic acid appended to the oxidized ethyl branch in the polyketide core (FIG. 6B).

TABLE 2

$^{13}$C and $^{1}$H and chemical shifts of kanglemycin A in $CD_2Cl_2$, collected at 25° C.$^a$

| Position | Atom type | $\delta_C$ | $\delta_H$ (mult., J in Hz) |
|---|---|---|---|
| 1 | C | 185.8 | |
| 2 | C | 140.9 | |
| 3 | CH | 117.0 | 7.80 (s) |
| 4 | C | 184.9 | |
| 5 | C | 111.7 | |
| 6 | C | 171.8 | |
| 7 | C | 116.9 | |
| 8 | C | 167.4 | |
| 9 | C | 111.2 | |
| 10 | C | 132.0 | |
| 11 | C | 194.1 | |
| 12 | C | 109.9 | |
| 13 | $CH_3$ | 23.7 | 1.67 (s) |
| 14 | $CH_3$ | 7.8 | 2.34 (s) |
| 15 | C | 171.6 | |
| 16 | C | 137.0 | |
| 17 | CH | 129.8 | 6.16 (d, 5.8) |
| 18 | CH | 128.2 | 5.93 (dd, 15.9, 5.8) |

TABLE 2-continued $^{13}$C and $^1$H and chemical shifts of kanglemycin A in CD$_2$Cl$_2$, collected at 25° C.[a]

| Position | Atom type | $\delta_C$ | $\delta_H$ (mult., J in Hz) |
|---|---|---|---|
| 19 | CH | 134.1 | 5.81 (dd, 15.9, 9.3) |
| 20 | CH | 53.0 | 2.15 (m) |
| 21 | CH | 68.9 | 3.68 (m) |
| 22 | CH | 33.8 | 1.84 (m) |
| 23 | CH | 79.0 | 2.85 (dd, 10.0, 1.8) |
| 24 | CH | 36.9 | 1.60 (m) |
| 25 | CH | 74.1 | 4.36 (dd, 9.5, 1.0) |
| 26 | CH | 37.0 | 2.13 (m) |
| 27 | CH | 81.5 | 3.85 (dd, 9.3, 2.7) |
| 28 | CH | 112.9 | 5.13 (dd, 12.8, 9.3)[b] |
| 29 | CH | 146.4 | 6.37 (d, 12.8) |
| 30 | CH$_3$ | 21.1 | 2.06 (s) |
| 32 | CH$_3$ | 12.9 | 0.94 (d, 7.0) |
| 33 | CH$_3$ | 9.4 | 0.69 (d, 6.7) |
| 34 | CH$_3$ | 13.4 | 0.38 (d, 7.2) |
| 35 | C | 174.1 | |
| 36 | CH$_3$ | 21.8 | 2.02 (s) |
| K1 | CH$_3$ | 19.8 | 1.07 (d, 6.3) |
| K2 | CH | 68.0 | 5.06 (dd, 12.7, 6.3) |
| K3 | C | 176.4 | |
| K4 | C | 40.8 | |
| K5 | CH$_3$ | 26.2 | 1.17 (s) |
| K6 | C | 172.3 | |
| K7 | CH$_2$ | 43.5 | 2.66 (d, 16.9) |
| | | | 2.53 (d, 16.9) |
| K8 | CH$_3$ | 24.9 | 1.23 (s) |
| K9 | CH | 97.2 | 4.65 (dd, 9.0, 1.1) |
| K10 | CH$_2$ | 33.5 | 2.23 (ddd, 15.5, 2.9, 1.1) |
| | | | 1.83 (m) |
| K11 | CH | 74.9 | 4.10 (m) |
| K12 | CH$_2$ | 95.4 | 5.13 (s)[b] |
| | | | 4.87 (s) |
| K13 | CH$_3$ | 75.9 | 3.64 (m) |
| K14 | CH | 70.5 | 3.36 (m) |
| K15 | CH$_3$ | 18.8 | 1.27 (d, 6.2) |
| NH | NH | | 8.34 (s) |
| OH-8 | OH | | 12.60 (s) |

[a]$^1$H and $^{13}$C NMR were obtained at 600 and 150 MHz, respectively. Reference chemical shifts for CD$_2$Cl$_2$ were $\delta_H$ 5.32 and $\delta_C$ 54.0. The concentration of kanglemycin A was 4.5 mM.
[b]Overlapped signals

TABLE 3

$^{13}$C and $^1$H and chemical shifts of kanglemycin V2 in MeOD, collected at −20 °C.[a]

| Position | Atom type | $\delta_C$ | $\delta_H$ (mult., J in Hz) |
|---|---|---|---|
| 1 | C | 150.4 | |
| 2 | C | 126.4 | |
| 3 | CH | 118.2 | 7.99 (s) |
| 4 | C | 150.5 | |
| 5 | C | 106.4 | |
| 6 | C | 167.9 | |
| 7 | C | 108.3 | |
| 8 | C | 191.7 | |
| 9 | C | 114.1 | |
| 10 | C | 115.4 | |
| 11 | C | 165.7 | |
| 12 | C | 112.9 | |
| 13 | CH$_3$ | 22.0 | 1.86 (s) |
| 14 | CH$_3$ | 7.4 | 2.01 (s) |
| 15 | C | 171.7 | |
| 16 | C | 134.7 | |
| 17 | CH | 132.0 | 6.30 (d, 11.2) |
| 18 | CH | 131.3 | 6.52 (dd, 15.6, 11.2) |
| 19 | CH | 132.5 | 5.94 (d, 15.6, 8.1) |
| 20 | CH | 51.1[d] | 2.33 (m) |
| 21 | CH | 70.1 | 4.06 (m) |
| 22 | CH | 35.1 | 1.81 (m) |
| 23 | CH | 77.9 | 3.06 (dd, 10.2, 1.8) |
| 24 | CH | 38.9 | 1.43 (m) |
| 25 | CH | 74.5 | 5.12 (dd, 10.3, 1.7) |
| 26 | CH | 42.0 | 1.20 (m) |
| 27 | CH | 78.2 | 3.92 (dd, 6.7, 2.0) |
| 28 | CH | 123.3 | 5.36 (dd, 11.6, 5.5) |
| 29 | CH | 141.8 | 6.22 (d, 11.6) |
| 30 | CH$_3$ | 20.4 | 2.08 (s) |
| 32 | CH$_3$ | 13.0 | 0.99 (d, 6.7) |
| 33 | CH$_3$ | 10.0 | 0.51 (br s) |
| 34 | CH$_3$ | 9.9 | −0.06 (d, 5.6) |
| 35 | C | 172.7 | |
| 36 | CH$_3$ | 20.9 | 2.06 (s) |
| K1 | CH$_3$ | 18.7 | 1.18 (d, 7.1) |
| K2 | CH | 71.0 | 5.02 (dd, 5.9, 4.1)[b] |
| K3 | C | 177.9 | |
| K4 | C | 41.7 | |
| K5 | CH$_3$ | 25.4 | 1.30 (s) |
| K6 | C | 174.8 | |
| K7 | CH$_2$ | 45.0 | 2.69 (d, 16.9) |
| | | | 2.56 (d, 16.9) |
| K8 | CH$_3$ | 26.8 | 1.18 (s)[b] |
| K9 | CH | 101.0 | 4.48 (dd, 7.8, 1.4) |
| K10 | CH$_2$ | 33.4 | 2.13 (m) |
| | | | 1.80 (m) |
| K11 | CH | 75.2 | 3.99 (m) |
| K12 | CH$_2$ | 95.7 | 5.06 (s) |
| | | | 4.76 (s) |
| K13 | CH$_3$ | 76.7 | 3.54 (dd, 9.1, 5.3) |
| K14 | CH | 71.3 | 3.30[b] |
| K15 | CH$_3$ | 18.9 | 1.18 (d, 6.2)[b] |
| K16 | CH$_2$ | 98.4 | 6.19 (d, 6.6) |
| | | | 5.48 (d, 6.6) |

Figure 8:
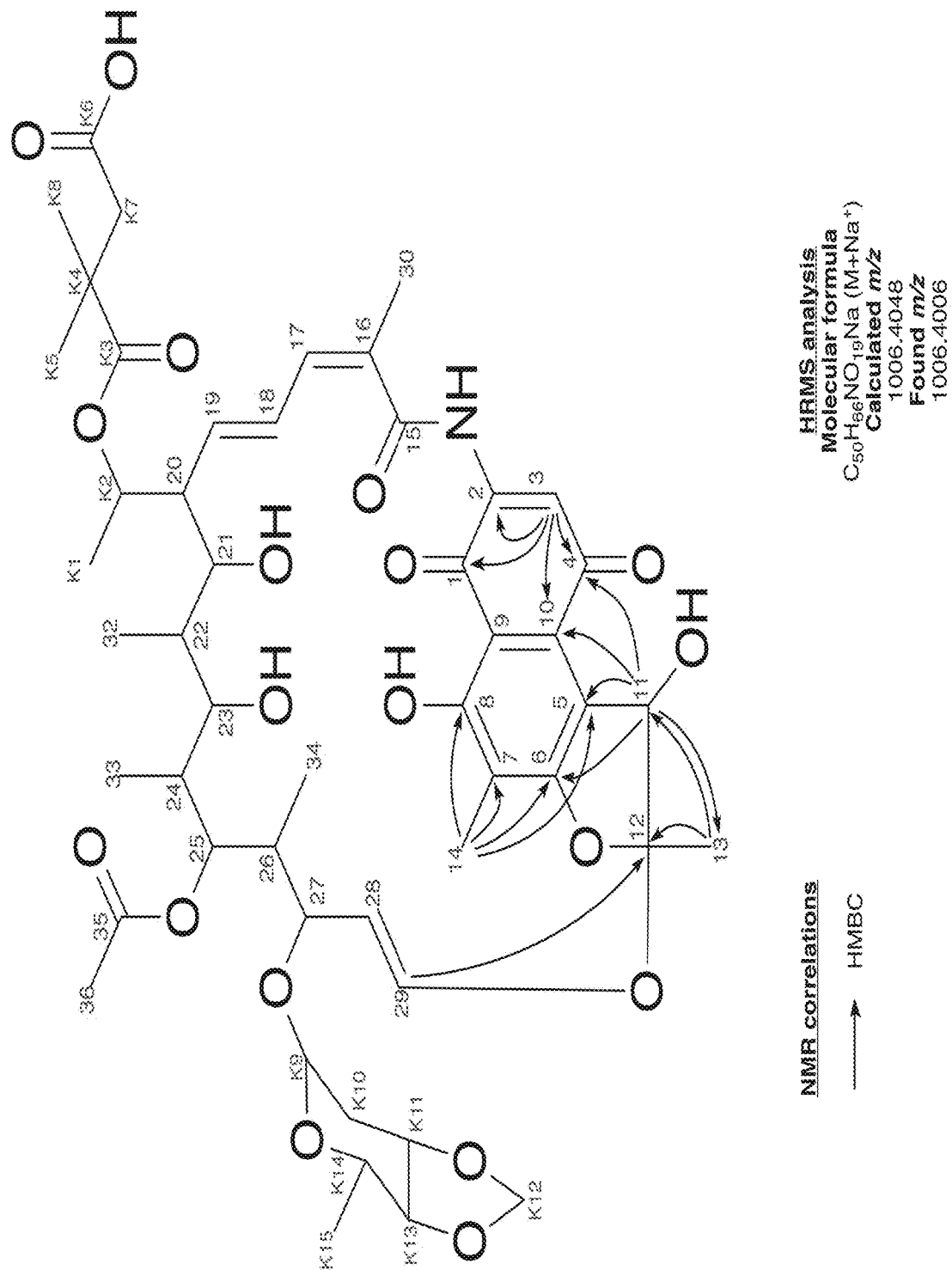
FIG. 8 depicts key HMBC and HRMS data used to establish the structure of Kanglemycin V1.
Figure 9:
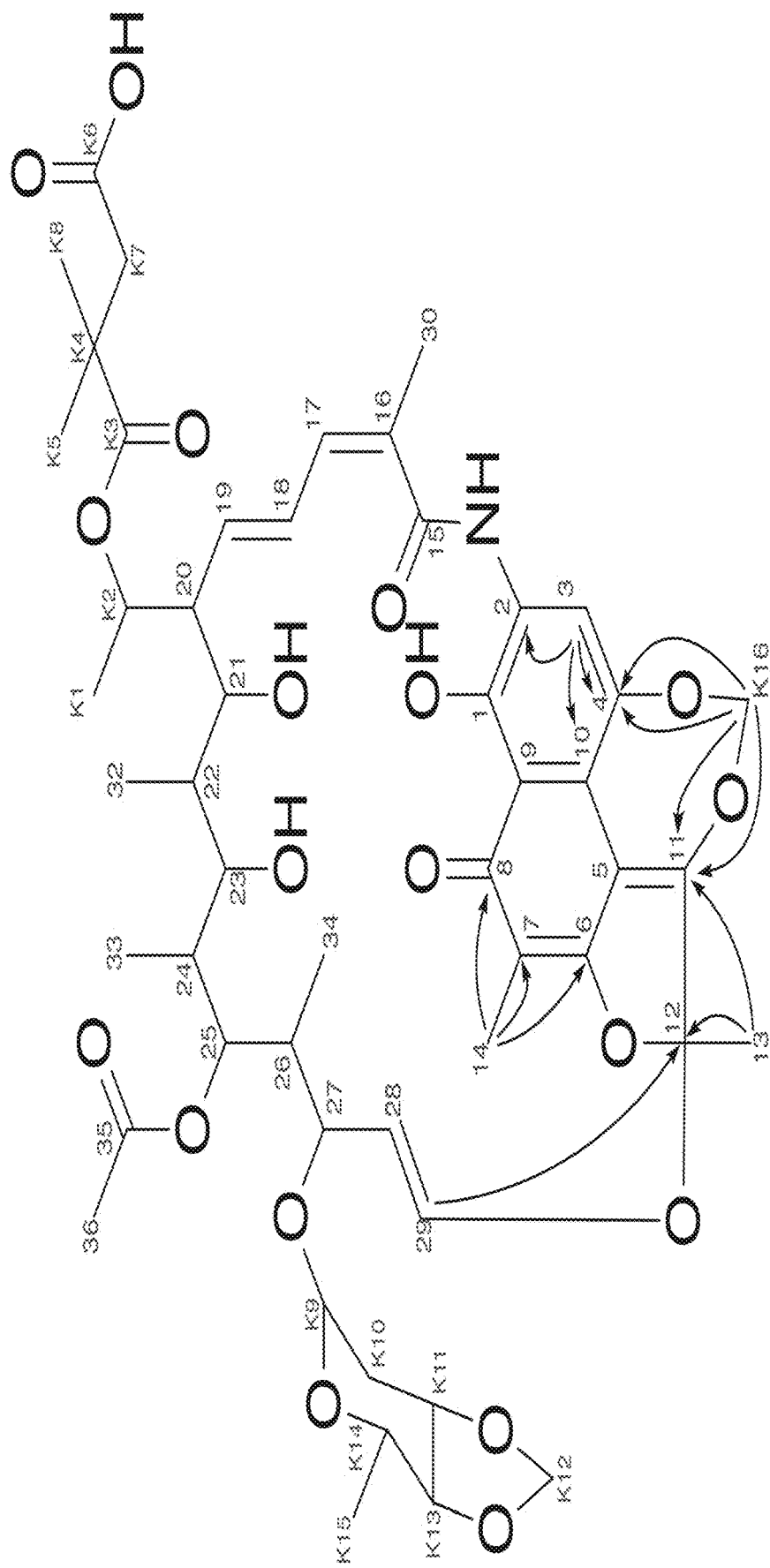
FIG. 9 depicts key HMBC and HRMS data used to establish the structure of Kanglemycin V2.

[a]$^1$H and $^{13}$C NMR were obtained at 500 and 125 MHz, respectively. Reference chemical shifts for MeOD were $\delta_H$ 3.31 and $\delta_C$ 49.0. The concentration of kangelmycin V2 was 2.9 mM.
[b]Overlapped signals
[c]Signal overlapped with solvent peak.
[d]13C chemical shift only observed by HMBC The predicted molecular formula for the second metabolite, kanglemycin V1 (2), suggested it was a reduced version of kanglemycin A. A comparison of 1 and 2D NMR data from 1 and 2 allowed for the assignment of this difference to the reduction of the C-11 ketone to an alcohol (FIG. 6B and FIG. 8, Table 4). It is believed that this reduction has only been seen in one previously described rifamycin congener, chaxamycin D (Rateb et al., 2011, J. Nat. Prod., 74:1491-1499, which is incorporated by reference herein in its entirety). In the case of the third metabolite, kanglemycin V2 (3), HRMS data indicated that it differed from kanglemycin A (1) by the addition of a CH$_2$ moiety (FIG. 6B and FIG. 9). With the exception of the chemical shifts associated with the naphthoquinone substructure, the same NMR arguments used to assign the structures of kanglemycins A and V1 could be used to determine the structure of compound 3. In the case of 3 however, both 1 and 2D NMR data indicated the presence of a naphthohydroquinone in place of a naphthoquinone in the structure (FIG. 9). The UV spectra of kanglemycin V2 (3) also supported a change in this ring system, as the $\lambda_{max}$ of 268-276 nm which is characteristic of the napthoquinone (Rateb et al., 2011, J. Nat. Prod., 74:1491-1499), was replaced with a $\lambda_{max}$ at 302 nm (FIG. 7). The formation of an additional seven membered ring off of the naphthohydroquinone substructure through the addition of a highly deshielded methylene was ultimately defined by HMBC correlations from the new methylene protons to C-4 and C-11 of the naphthohydroquinone (FIG. 9). It is believed that this seven-membered ring has not been previously seen in a rifamycin congener.

TABLE 4

$^{13}$C and $^1$H and chemical shifts of kanglemycin V1 in MeOD, collected at 25° C.$^a$

| Position | Atom type | $\delta_C$ | $\delta_H$ (mult., J in Hz) |
|---|---|---|---|
| 1 | C | 183.8 | |
| 2 | C | 142.9 | |
| 3 | CH | 118.2 | 7.69 (s) |
| 4 | C | 188.8 | |
| 5 | C | 109.4 | |
| 6 | C | 164.9 | |
| 7 | C | 114.3 | |
| 8 | C | 165.8 | |
| 9 | C | 126.3 | |
| 10 | C | 127.1 | |
| 11 | CH | 77.1 | 5.49 (s) |
| 12 | C | 113.9 | |
| 13 | CH$_3$ | 25.0 | 1.86 (s)$^b$ |
| 14 | CH$_3$ | 8.4 | 2.20 (s) |
| 15 | C | 172.0 | |
| 16 | C | 133.6 | |
| 17 | CH | 133.0 | 6.33 (d, 11.3) |
| 18 | CH | 130.8 | 6.41 (dd, 15.4, 11.3) |
| 19 | CH | 134.4 | 5.98 (dd, 15.4, 8.4) |
| 20 | CH | 51.6 | 2.33 (m) |
| 21 | CH | 70.2 | 4.06 (dd, 7.6, 3.9) |
| 22 | CH | 35.3 | 1.86 (m)$^b$ |
| 23 | CH | 78.3 | 3.07 (dd, 11.1, 1.8) |
| 24 | CH | 38.4 | 1.64 (m) |
| 25 | CH | 74.9 | 5.11 (dd, 10.5, 1.6) |
| 26 | CH | 41.2 | 1.40 (m) |
| 27 | CH | 78.0 | 3.90 (m) |
| 28 | CH | 118.4 | 5.16 (dd, 12.3, 4.0) |
| 29 | CH | 143.3 | 6.15 (d, 12.3) |
| 30 | CH$_3$ | 20.2 | 2.07 (s) |
| 32 | CH$_3$ | 13.5 | 1.01 (d, 7.1) |
| 33 | CH$_3$ | 10.1 | 0.6 (d, 6.8) |
| 34 | CH$_3$ | 10.3 | 0.22 (d, 7.0) |
| 35 | C | 173.5 | |
| 36 | CH$_3$ | 20.9 | 2.03 (s) |
| K1 | CH$_3$ | 18.8 | 1.19 (d, 6.9) |
| K2 | CH | 71.1 | 5.06 (m)$^c$ |
| K3 | C | 177.9 | |
| K4 | C | 41.8 | |
| K5 | CH$_3$ | 26.6 | 1.27 (s)$^d$ |
| K6 | C | 174.6 | |
| K7 | CH$_2$ | 44.9 | 2.75 (d, 16.5) |
| | | | 2.57 (d, 16.5) |
| K8 | CH$_3$ | 25.3 | 1.27 (s)$^d$ |
| K9 | CH | 101.0 | 4.52 (dd, 8.0, 2.3) |
| K10 | CH$_2$ | 33.6 | 2.10 (ddd, 13.5, 8.0, 4.8) |
| | | | 1.74 (m) |
| K11 | CH | 75.2 | 4.02 (m) |
| K12 | CH$_2$ | 95.7 | 5.06 (s)$^c$ |
| | | | 4.79 (s) |
| K13 | CH$_3$ | 77.0 | 3.55 (dd, 9.0, 5.5) |
| K14 | CH | 71.2 | 3.31$^e$ |
| K15 | CH$_3$ | 18.9 | 1.20 (d, 6.3) |

$^a$$^1$H and $^{13}$C NMR were obtained at 600 and 150 MHz, respectively. Reference chemical shifts for MeOD were $\delta_H$ 3.31 and $\delta_C$ 49.0. The concentration of kanglemycin V1 was 4.5 mM.
$^{b,c,d}$Overlapped signals
$^e$Signal overlapped with solvent peak Kanglemycin biosynthesis: Differences in gene content between other rifamycin congener gene clusters and the kanglemycin (kng) gene cluster are consistent with many of the new structural features found on the kanglemycins (FIG. 6A). In this biosynthetic proposal, the digitoxose deoxygsugar is produced by the NDP-hexose-4-ketoreductase, NDP-hexose-3-ketoreductase, O-methyltransferase, NDP-hexose-2,3-dehydratase and cytochrome P450 encoded by the kng gene cluster (kng22, kng23, kng24, kng27 and kng28, respectively), and it is appended to the polyketide core by the predicted glycosyltransferase encoded by kng26 (FIG. 6C) (He et al., 2017, Sci. Rep., 7:9119; Ikezawa et al., 2003, J. Biol. Chem., 278:38557-38565; Thibodeaux et al., 2008, Angew. Chem. Int. Ed. Engl., 47:9814-9859; Bihlmaier et al., 2006, Antimicrob. Agents Chemother., 50:2113-2121, which are incorporated by reference herein in their entireties). The origin of the methylenedioxy bridge in kanglemycin V2 is not obvious from bioinformatics; however, one potential route is the repeated use of the methyltransferase (kng24) and cytochrome P450 (kng28) that it is believed are involved in introducing the same functionality into the digitoxose sugar. The presence of the new ethyl branch in the kanglemycin polyketide core is consistent with the predicted Emal specificity of the kng cluster's AT8* domain in kngD. While it is expected that the predicted propionyl-CoA carboxylase (kng30), Mmal mutase (kng34A/B) and CoA transferase (kng35) encoded by the kng gene cluster are involved in generating a succinic acid moiety, the biosynthetic origin of a gem-dimethyl succinic acid has not been described previously and additional experiments will be required to better understand the origin of this functionality in the kanglemycins.

Antibacterial Activity

Kanglemycins A, V1 and V2 are active as antibiotics against Gram-positive bacteria, including *Staphylococcus aureus, Staphylococcus epidermidis, Listeria monocytogenes* and *M. tuberculosis* (Table 5). Interestingly, kanglemycin V1 and V2 both show improved activity against *M. tuberculosis* (H37Rv; IC$_{90}$ 3.12 and 1.56 µM, respectively) compared to kanglemycin A (12.5 µM). There was particular interest in whether the complex structural features seen in the kanglemycins might impart improved activity against mutations in RNAP that confer resistance to rifampicin. Substitutions at just three RNAP amino acid positions, S531, H526 and D516, account for the vast majority of mutations observed in rifampicin resistant *M. tuberculosis* clinical isolates (Ramaswamy et al., 1998, Tuber. Lung Dis., 79:3-29, which is incorporated by reference herein in its entirety). The antibacterial activity of the kanglemycins against rifampicin resistant RNAP mutants was assessed in vivo using a collection of *S. aureus* strains carrying various RNAP point mutations and in vitro using purified wild-type and mutant (S477L) *Mycobacterium smegmatis* RNAP (Srivastava et al., 2012, Antimicrob. Agents, 56:6250-6255; Hubin et al., 2017, Elife, 6:e22520, which are incorporated by reference herein in their entireties). The use of these models allowed for the exploration of the activity of the kanglemycins against mutations that correspond to the most commonly mutated sites in rifampicin resistant TB, without necessitating the use of restrictive BSL3 assay conditions.

TABLE 5

Antibacterial activity of the kanglemycins

| Organism | | Kang A MIC (µg/mL) | Kang V1 MIC (µg/mL) | Kang V2 MIC (µg/mL) | Rifampicin MIC (µg/mL) |
|---|---|---|---|---|---|
| *Acinetobacter baumannii* | ATCC17978 | >64 | >64 | >64 | ND |
| *Enterococcus faecium* | Com15 | 64 | 32 | 64 | 4.0 |

TABLE 5-continued

Antibacterial activity of the kanglemycins

| Organism | | Kang A MIC (µg/mL) | Kang V1 MIC (µg/mL) | Kang V2 MIC (µg/mL) | Rifampicin MIC (µg/mL) |
|---|---|---|---|---|---|
| Listeria monocytogenes | ATCC15313 | 2.0 | 1.0 | 1.0 | 0.031 |
| Proteus mirabilis | ATCC29906 | >64 | >64 | >64 | ND |
| Pseudomonas aeruginosa | PAO1 | 64 | 64 | 64 | 32 |
| Salmonella enterica | IR715 | >64 | >64 | >64 | ND |
| Staphylococcus aureus | ATCC12600 | 0.62 | 0.069 | 0.62 | 0.023 |
| Staphylococcus aureus | ATCC BAA-42 | 1.0 | 0.13 | 1.0 | 0.016 |
| Staphylococcus aureus | ATCC BAA-1721 | 2.0 | 0.063 | 0.25 | 0.0078 |
| Staphylococcus aureus | NCTC 8325 pT181 | 0.25 | 0.063 | 0.25 | 0.031 |
| Staphylococcus aureus | USA100 | 1.0 | 0.13 | 1.0 | 0.0078 |
| Staphylococcus aureus | USA200 | 2.0 | 0.25 | 2.0 | 0.0078 |
| Staphylococcus aureus | USA800 | 0.5 | 0.063 | 1.0 | 0.016 |
| Staphylococcus epidermidis | RP62A | 0.25 | 0.031 | 0.25 | 0.016 |
| Mycobacterium tuberculosis[a] | H37Rv | 13 | 3.1 | 1.6 | 0.20 |

ND, not determined.
[a]IC$_{90}$ values are shown.

Kanglemycins V1 and V2 are both active against rifamycin resistant *S. aureus* strains carrying RNAP mutations at sites corresponding to those commonly mutated in rifampicin resistant *M. tuberculosis* clinical isolates (FIG. 6D). Kanglemycin V1 showed an ~80-fold lower MIC (0.069 µg/mL) than rifampicin (5.6 µg/mL) against a D471Y mutant strain. Kanglemycin V2 exhibited similarly potent activity (MIC 0.069 µg/mL) against an *S. aureus* strain carrying an S486L mutation, which corresponds to the most commonly observed resistance mutation in *M. tuberculosis* clinical isolates (S531L), appearing in ~40-80% of sequenced isolates from geographically diverse regions of the world (FIG. 6D) (Tadesse et al., 2016, Int. J. Mycobacteriol., 5:185-191; Thirumurugan et al., 2015, Infect. Public Health, 8:619-625; Sajduda et al., 2004, J. Clin. Microbiol., 42:2425-2431; Cavusoglu et al., 2002, J. Clin. Microbiol., 40:4435-4438; Brossier et al., 2006, J. Clin. Microbiol., 44:3659-3664; Singhal et al, 2017, J. Epidemiol. Glob. Health, 7:175-180; Johansen et al., 2003, J. Clin. Microbiol., 41:4454-4456; Barnard et al, 2008, Am. J. Respir. Crit. Care Med., 177:787-792; Muthaiah et al., 2017, Journal of Clinical Tuberculosis and Other Mycobacterial Diseases, 8:19-25, which are incorporated by reference herein in their entireties). As with *M. tuberculosis*, the S486L mutation in *S. aureus* completely abrogates antibacterial activity of rifampicin (MIC>50 µg/mL). Interestingly, Kanglemycin V2 showed more potent activity against the S486L mutant than against the wild type strain, suggesting it might have evolved in an environment where this variant is the dominant form of RNAP.

To determine whether the activity of the kanglemycins against the *S. aureus* S486L mutant could be generalized to *M. tuberculosis* carrying the equivalent RNAP mutation, the in vitro activity of the kanglemycins against purified *M. smegmatis* RNAP was tested using a run-off transcription assay (FIG. 6E). The *M. smegmatis* RNAP exhibits 91% sequence identity with *M. tuberculosis* RNAP at the amino acid level and shows complete conservation of residues in the rifampicin binding pocket (Hubin et al., 2017, Elife, 6:e22520, which is incorporated by reference herein in its entirety). It was found that the kanglemycins were all potent in vitro inhibitors of wild-type *M. smegmatis* RNAP, with comparable activity to rifampicin. While rifampicin was inactive against an S447L RNAP mutant (corresponding to *M. tuberculosis* S531L and *S. aureus* S486L), all three kanglemycins displayed high levels of activity against this mutant. In agreement with the results of the *S. aureus* MIC assays, kanglemycin V2 showed the highest potency against the mutant *M. smegmatis* RNAP (FIG. 6E). A detailed analysis of the run-off transcription assays suggested that the mechanism by which the kanglemycins inhibit RNAP may differ from that of rifampicin. During inhibition of transcription by rifampicin, steric occlusion of the nascent transcript by the bound antibiotic results in the production of short, abortive nucleotide transcripts (FIG. 6E) (Campbell et al., 2001, Cell, 104:901-912, which is incorporated by reference herein in its entirety). These abortive transcripts are absent or greatly reduced in the presence of the kanglemycins, suggesting that inhibition by the kanglemycins does not involve the same steric occlusion mechanism.

On the Evolution of a Kanglemycin-Like Gene Cluster

Figure 10:
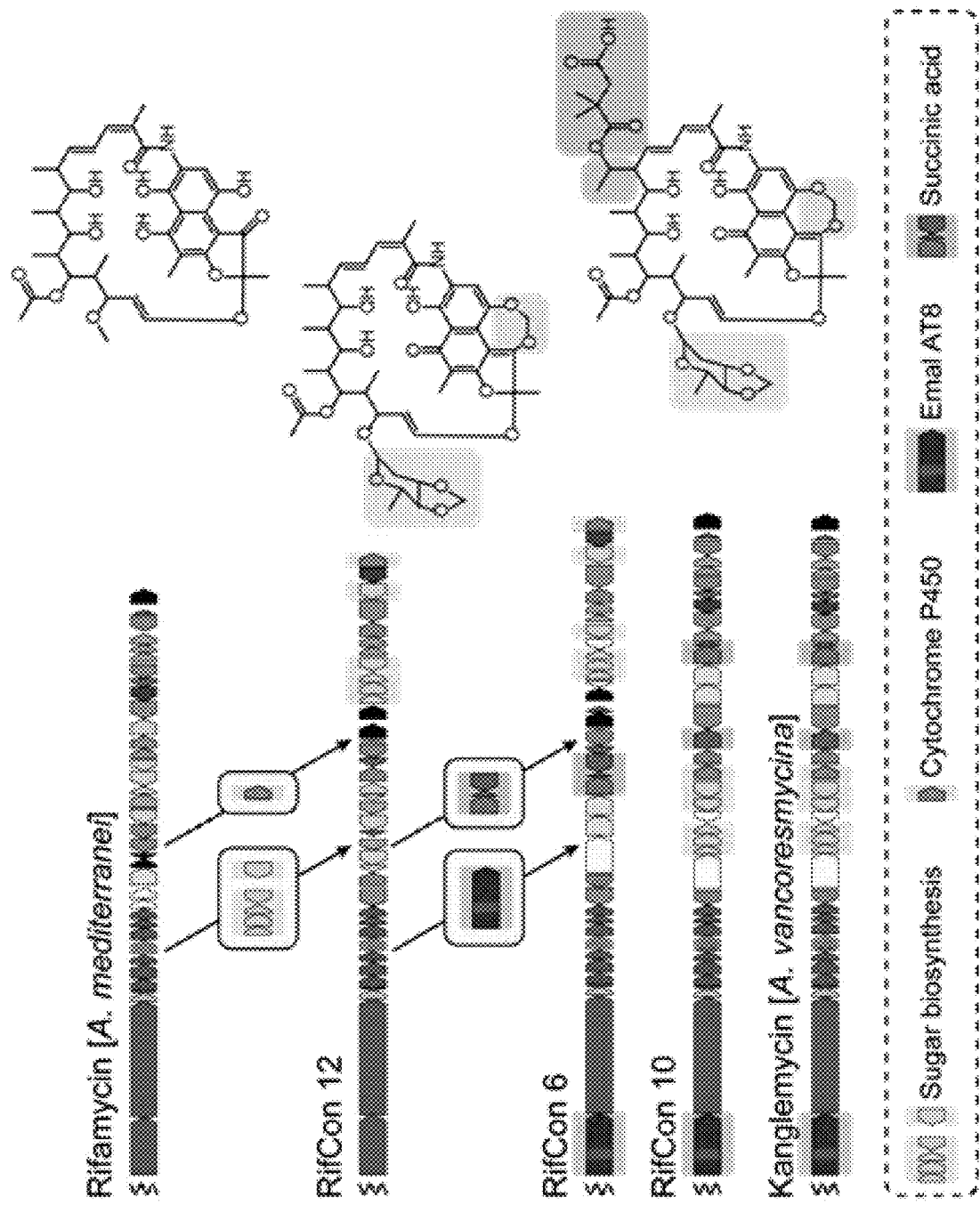
FIG. 10 depicts a model for the evolution of a structurally complex kanglemycin family molecule from a simpler rifamycin core. In this model, a stepwise increase in structural complexity is envisioned to result from a series of horizontal gene transfer events. Genes acquired at each step are shown in boxes and are highlighted according to the structural feature they are predicted to encode.
Figures 11A, 11B:
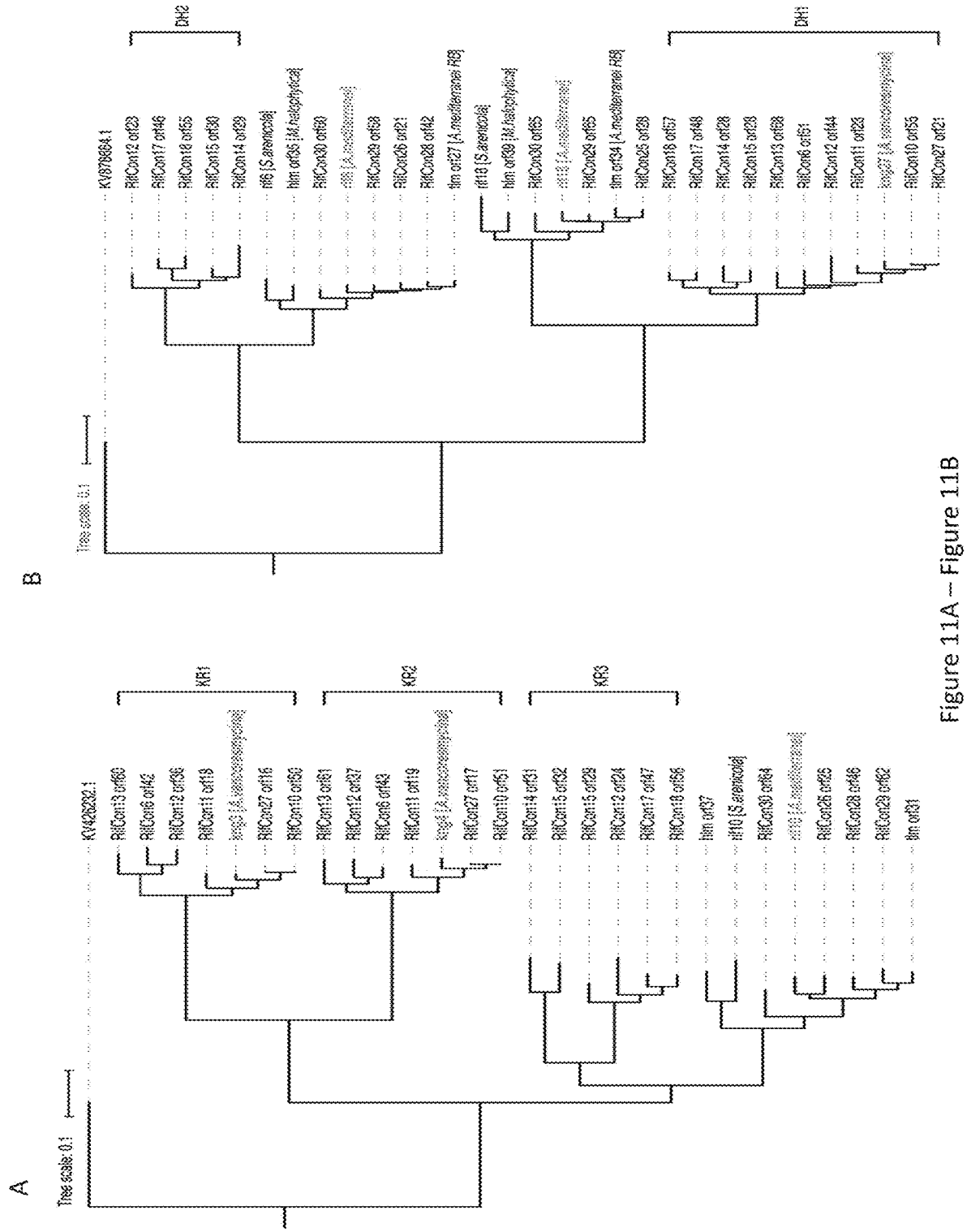
FIG. 11A and FIG. 11B, depicts tailoring genes that are predicted to encode enzymes that are phylogenetically distinct from those found in known rifamycin-like gene clusters.
Figure 12:
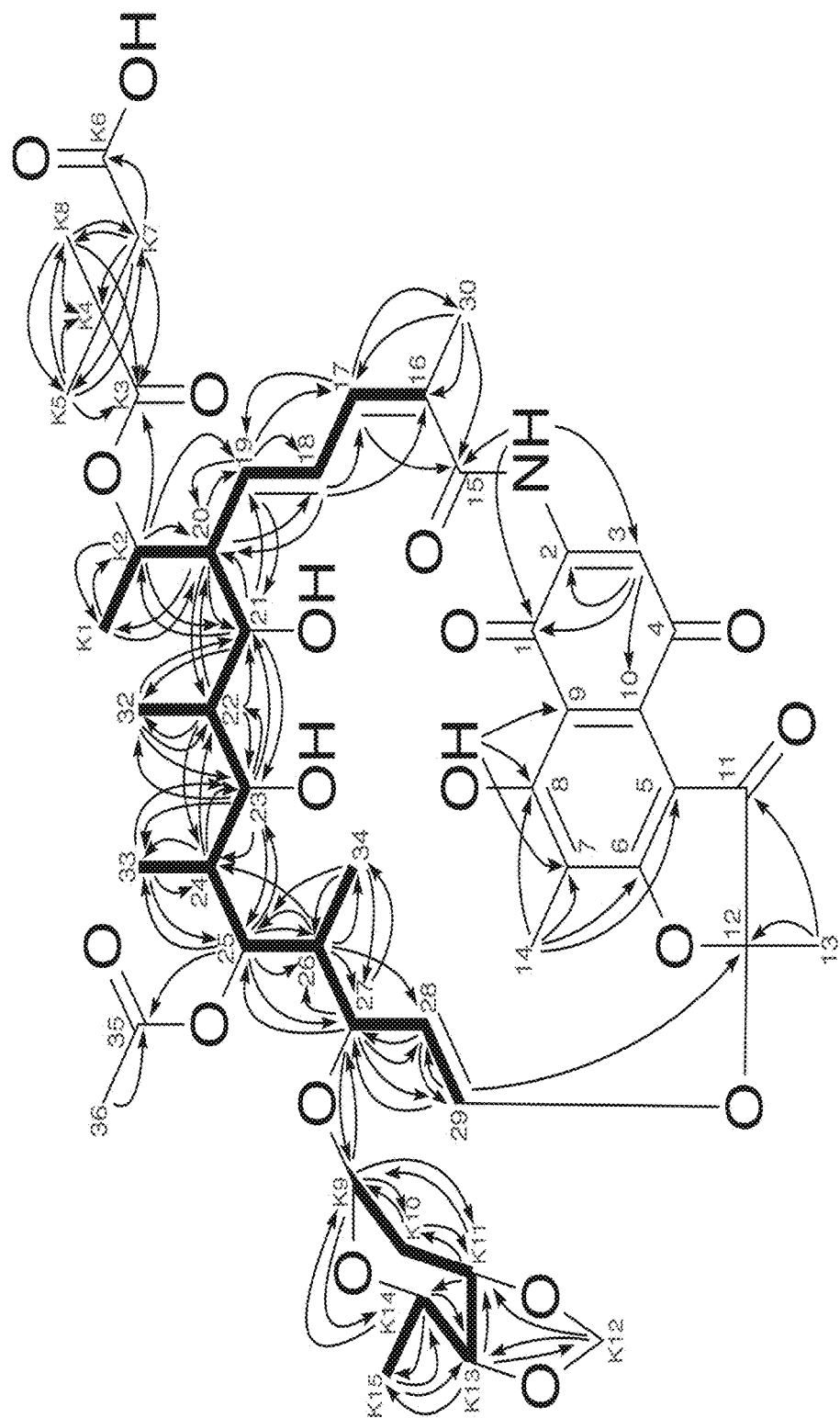
FIG. 12 depicts HMBC, COSY and HRMS data used to establish the structure of Kanglemycin A. Some $^{13}C$ chemical shifts have been reassigned compared to the original report describing kanglemycin A.
Figures 13A, 13B:
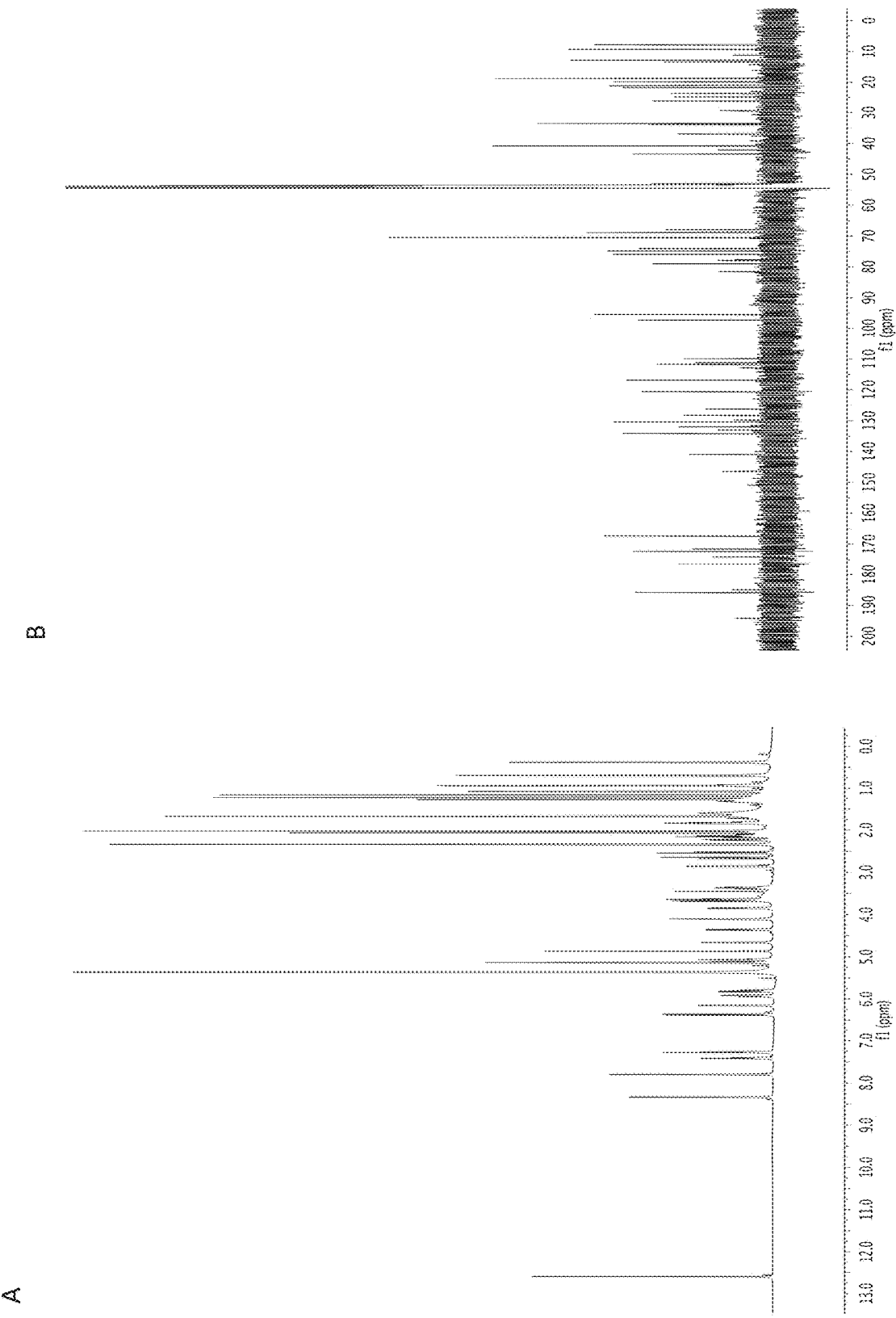
FIG. 13A and FIG. 13B, depicts NMR spectra of kanglemycin A.
Figures 14A, 14B:
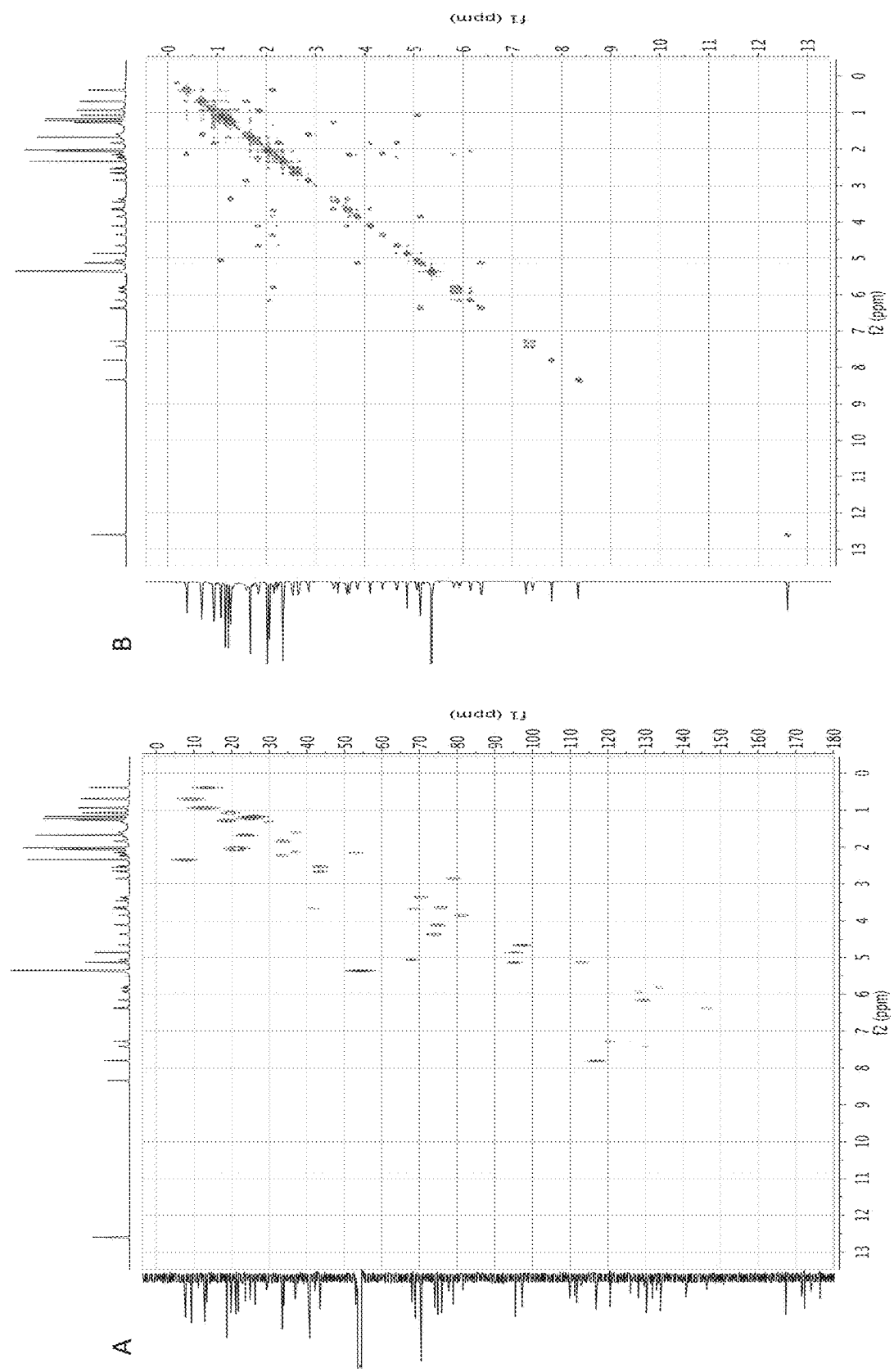
FIG. 14A and FIG. 14B, depicts 2-D NMR spectra of kanglemycin A.
Figure 15:
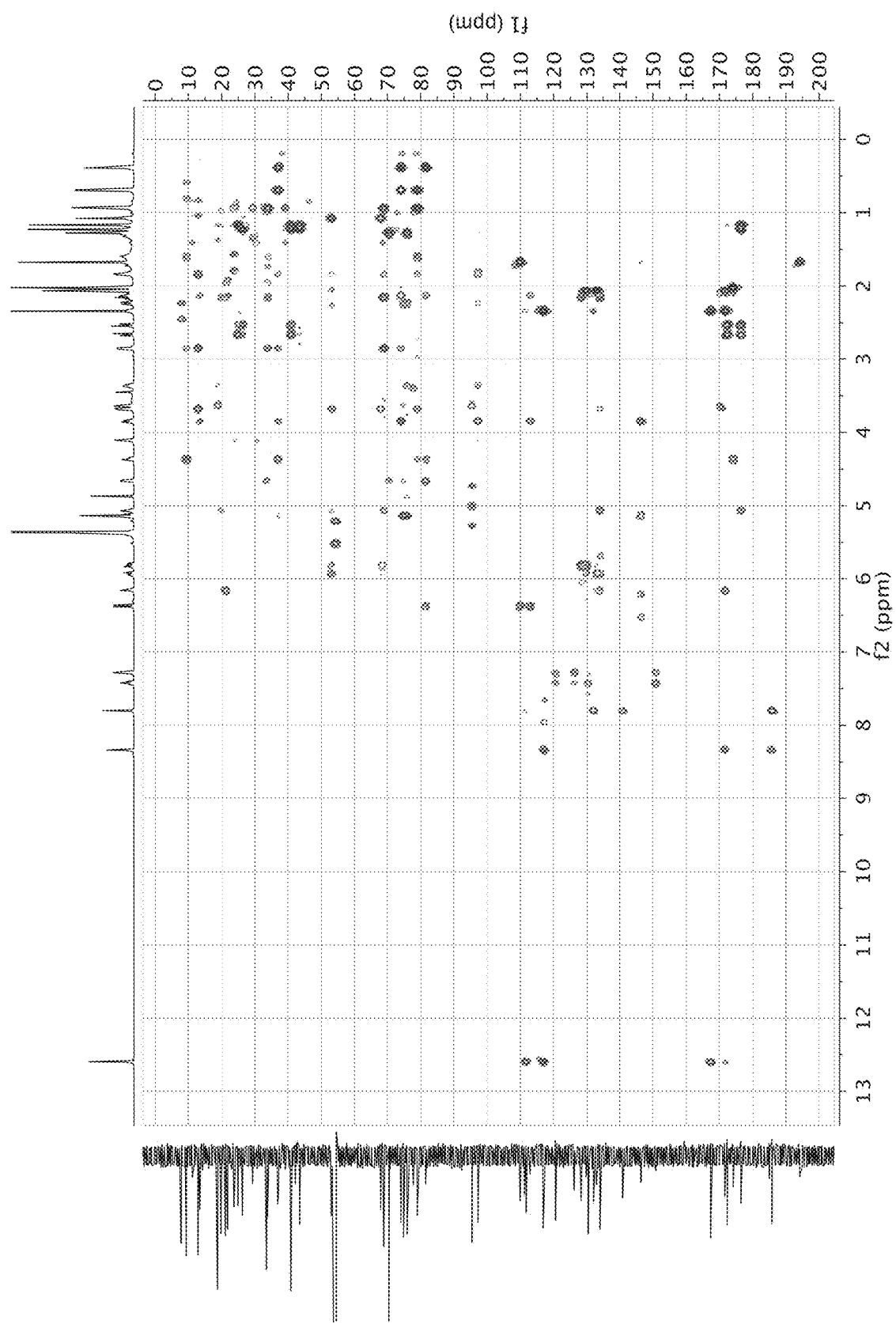
FIG. 15 depicts an HMBC spectrum of kanglemycin A in $CD_2Cl_2$, collected at 25° C.
Figures 16A, 16B:
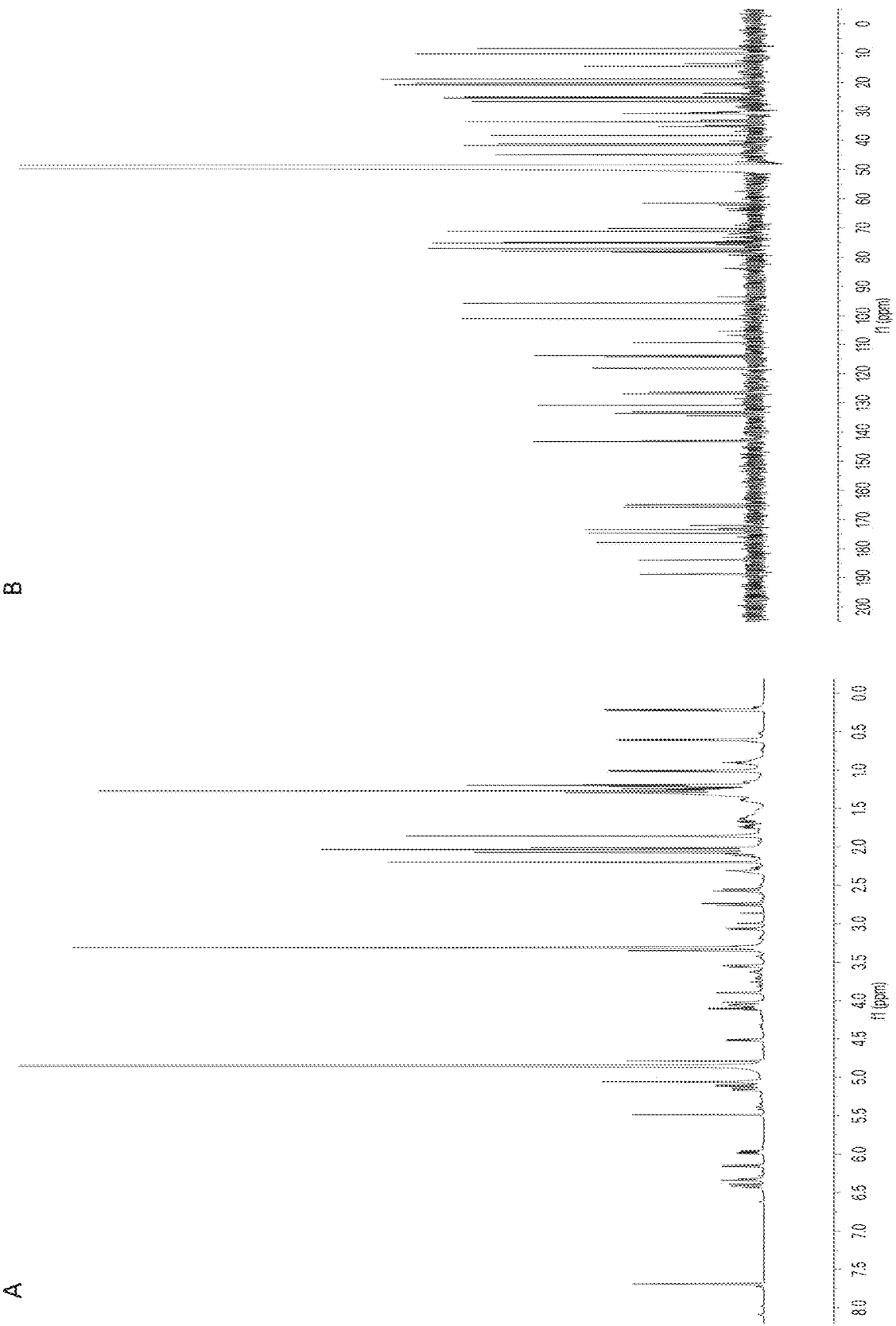
FIG. 16A and FIG. 16B, depicts NMR spectra of Kanglemycin V1.
Figures 17A, 17B:
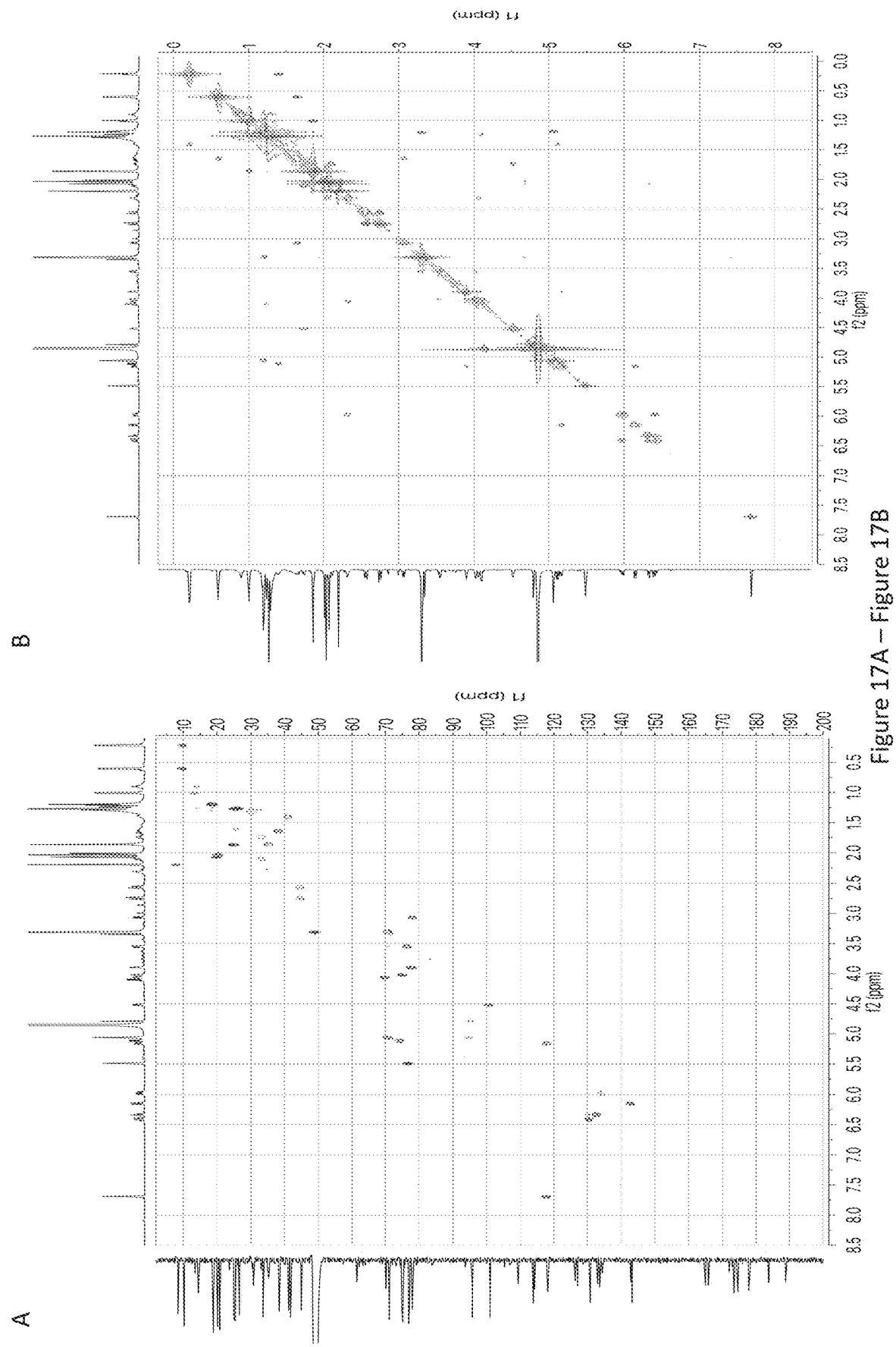
FIG. 17A and FIG. 17B, depicts 2-D NMR spectra of kanglemycin V1.
Figure 18:
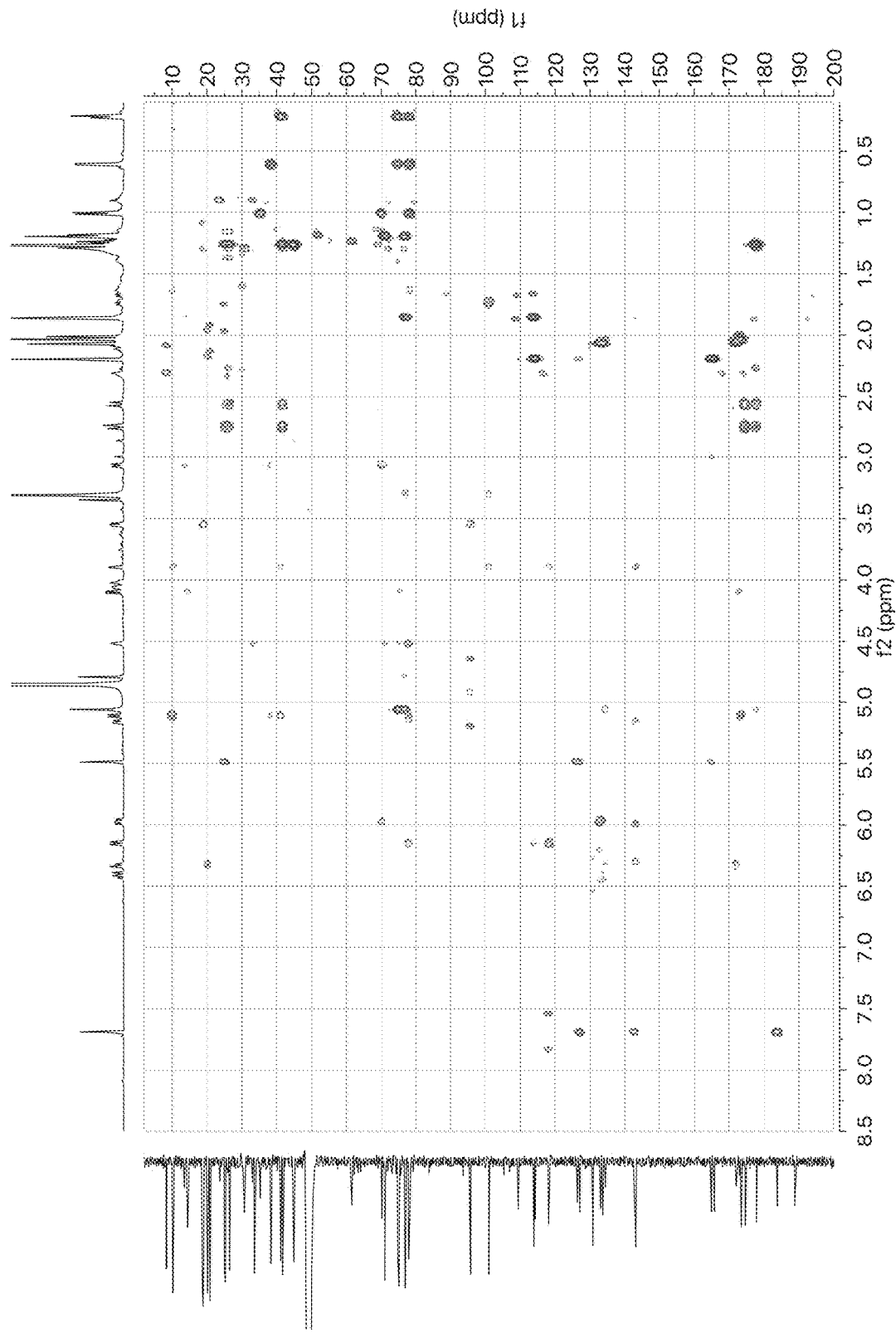
FIG. 18 depicts an HMBC spectrum of kanglemycin V1 in MeOD, collected at 25° C.
Figure 19:
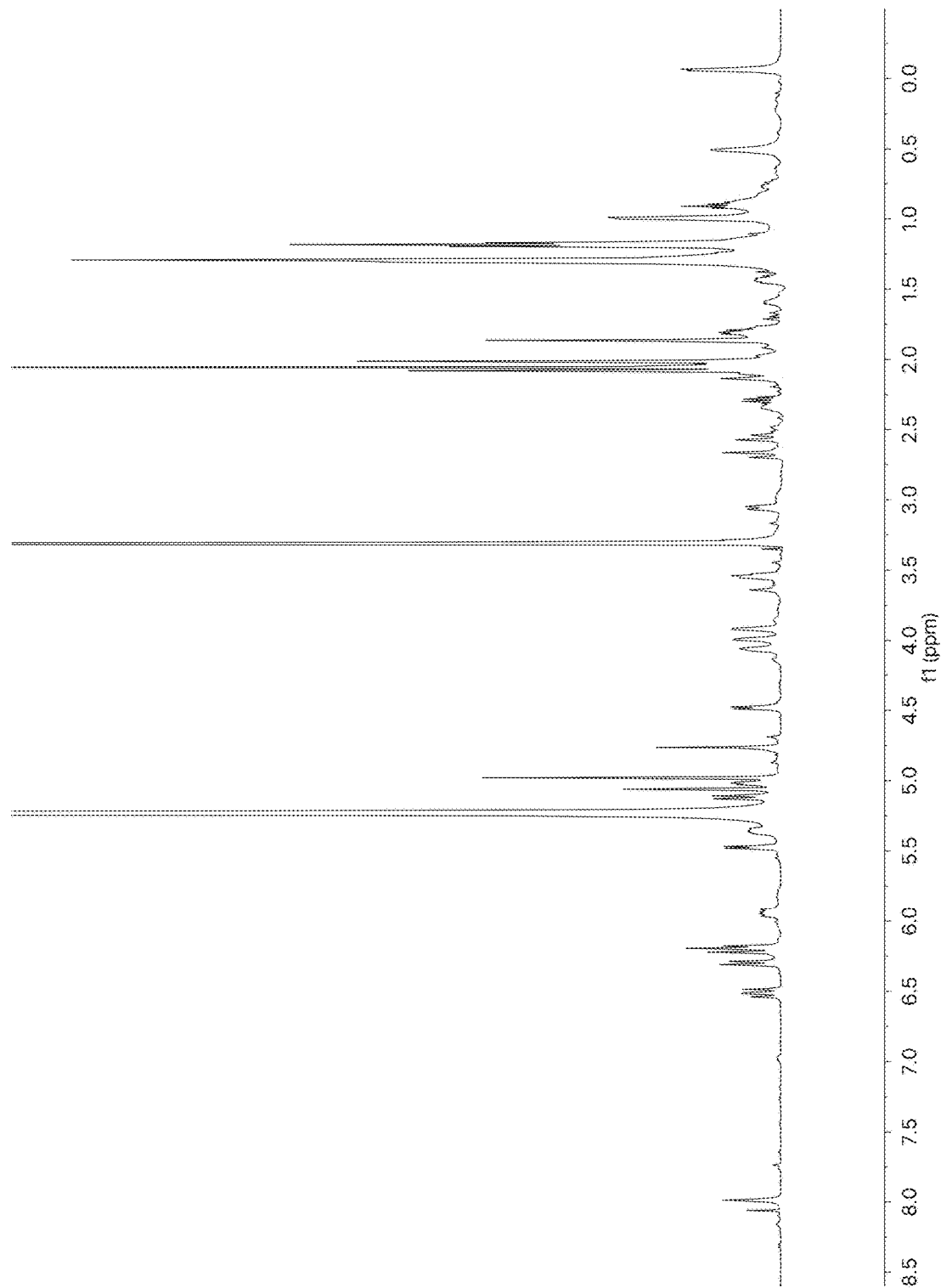
FIG. 19 depicts a $^1H$ NMR spectrum of kanglemycin V2 in MeOD, collected at −20° C.
Figure 20:
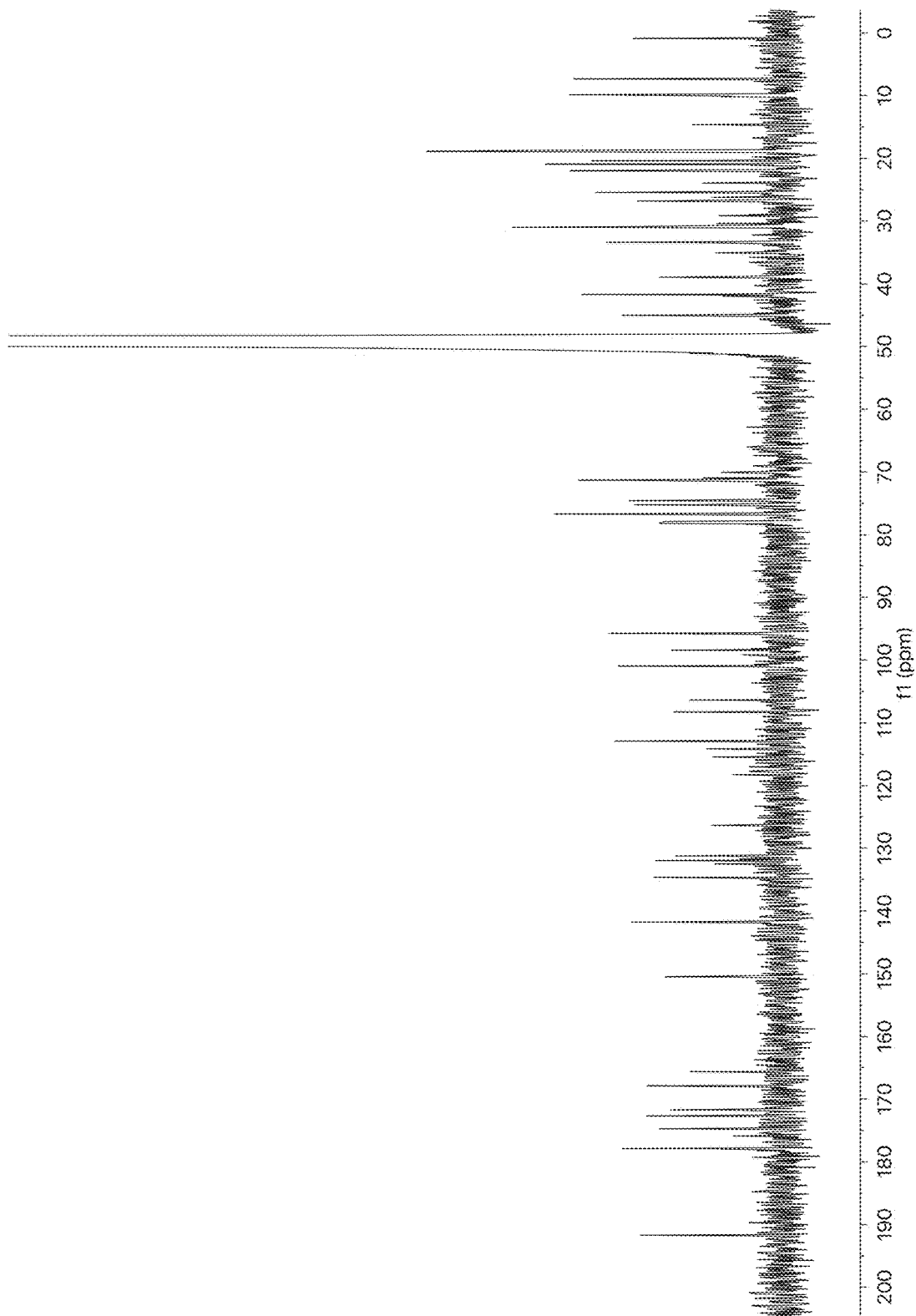
FIG. 20 depicts a $^{13}C$ NMR spectrum of kanglemycin V2 in MeOD, collected at −20° C.
Figure 21:
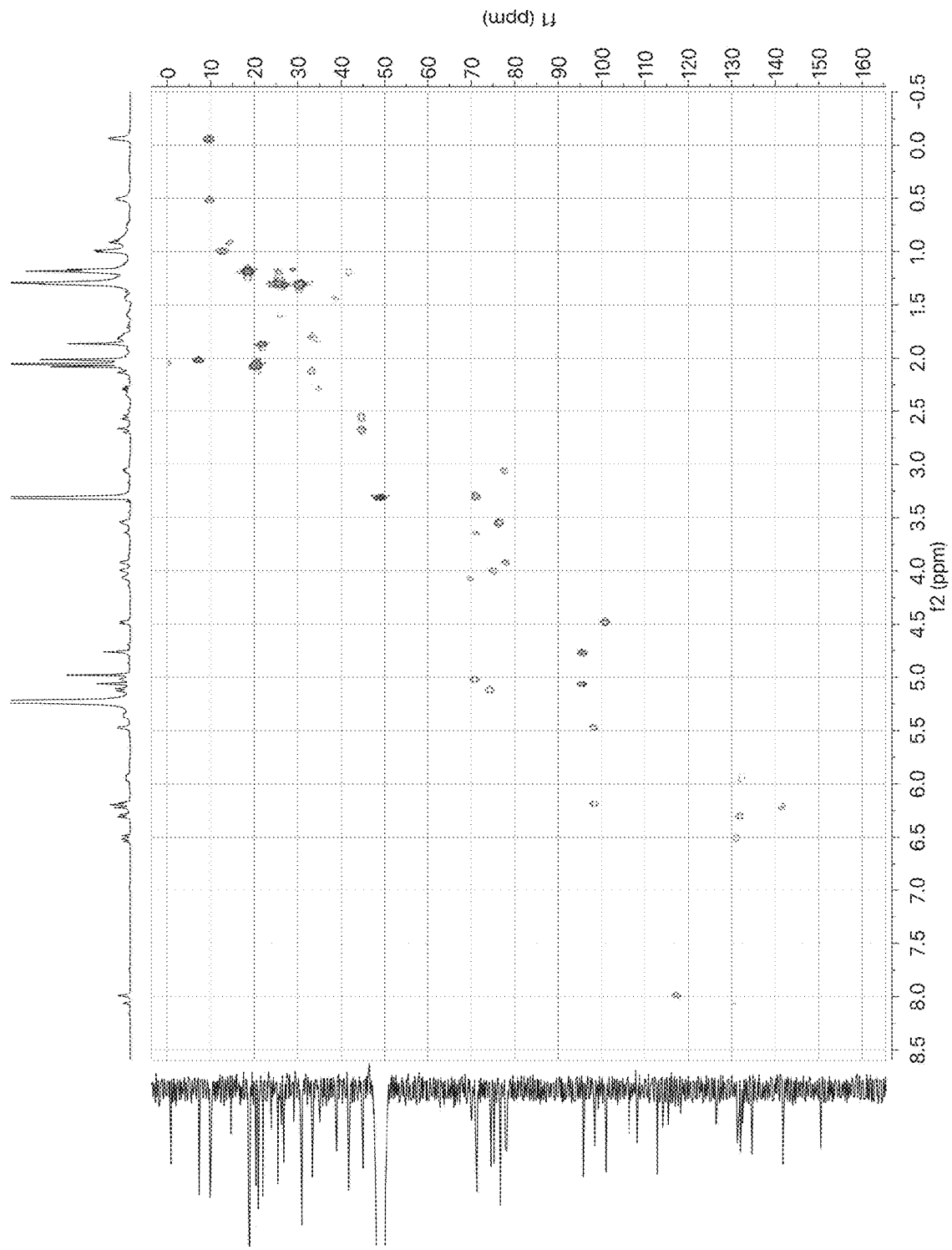
FIG. 21 depicts an HSQC NMR spectrum of kanglemycin V2 in MeOD, collected at −20° C.
Figure 22:
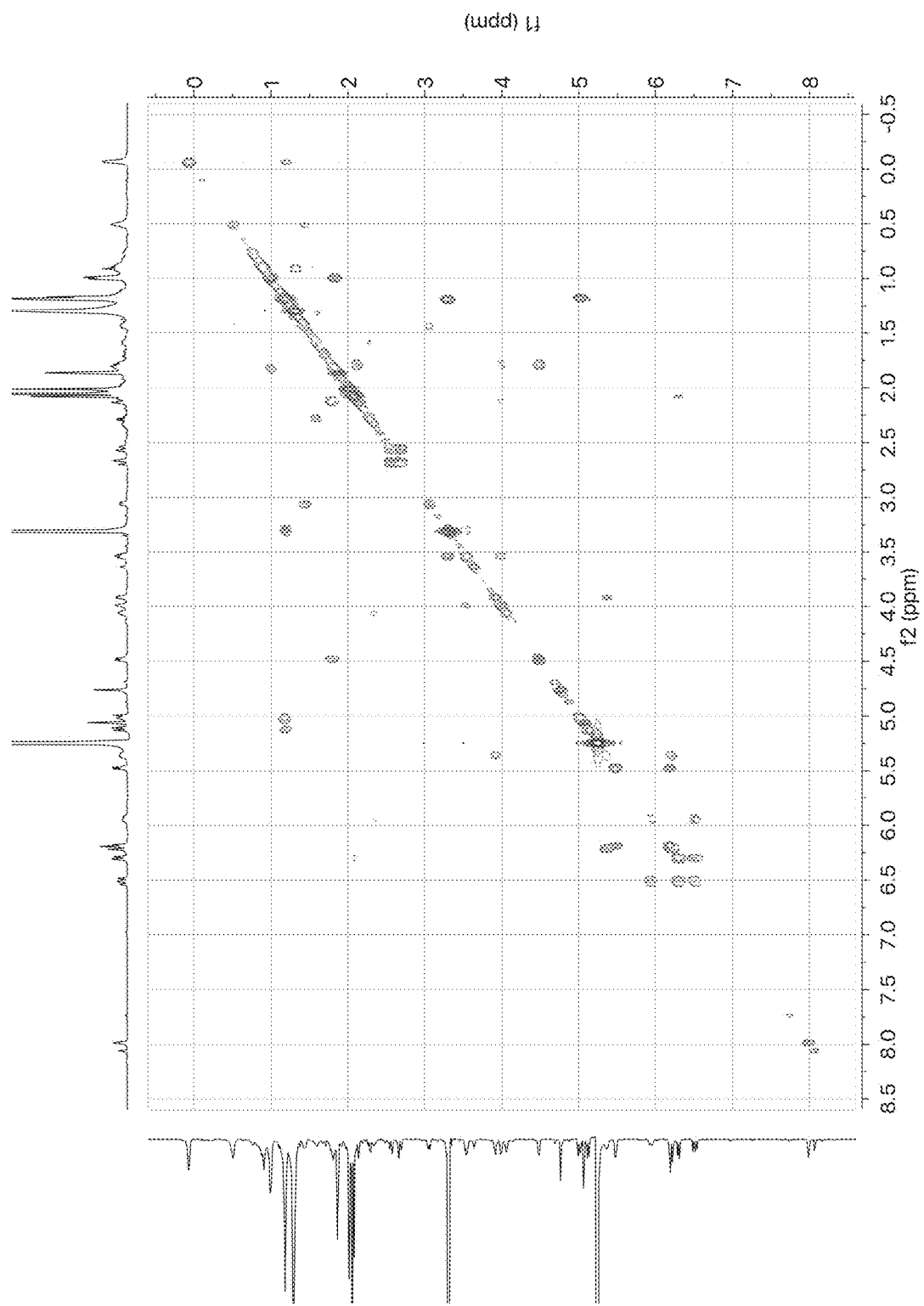
FIG. 22 depicts a COSY NMR spectrum of kanglemycin V2 in MeOD, collected at −20° C.
Figure 23:
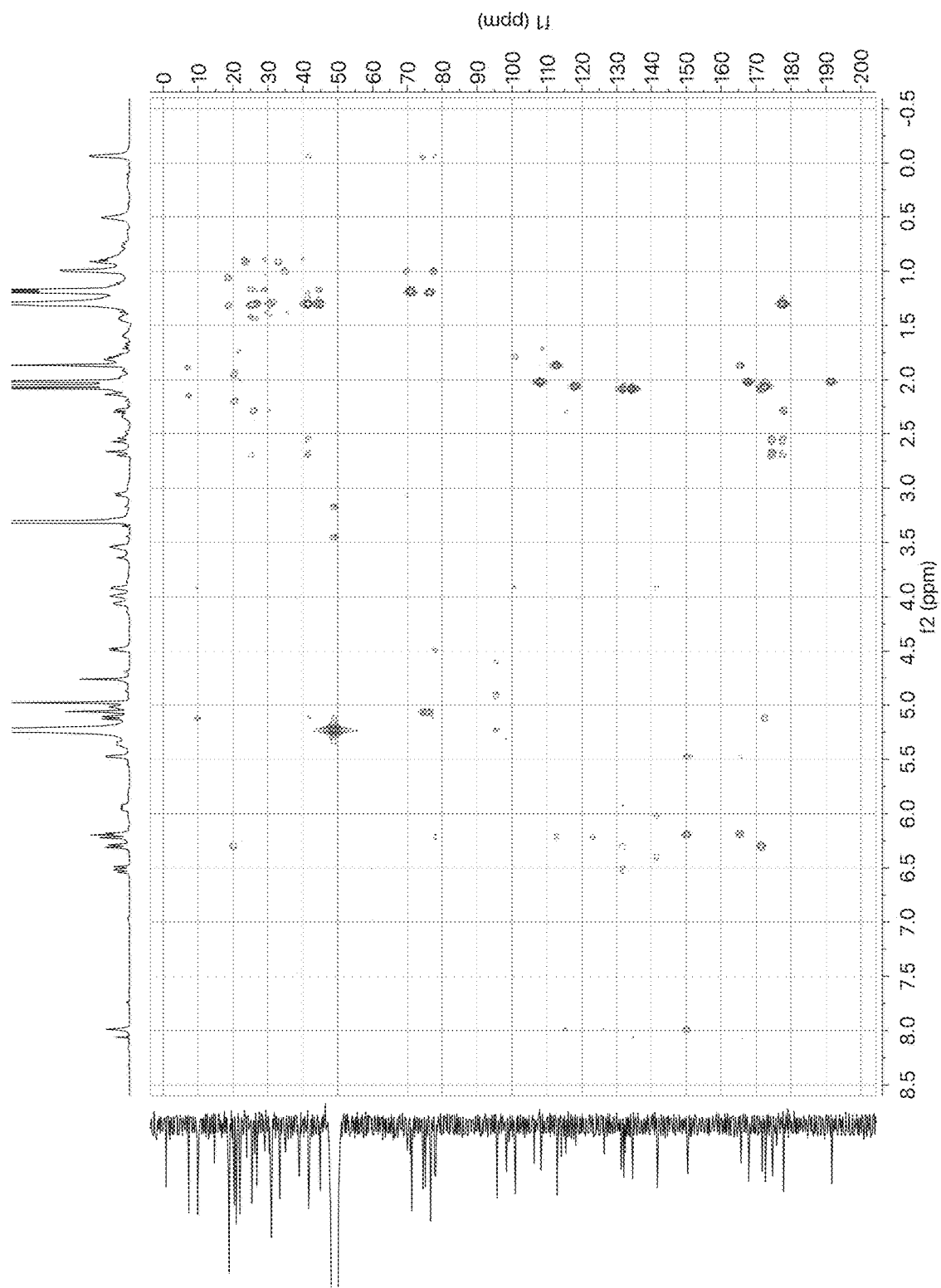
FIG. 23 depicts an HMBC spectrum of kanglemycin V2 in MeOD, collected at −20° C.
Figure 24:
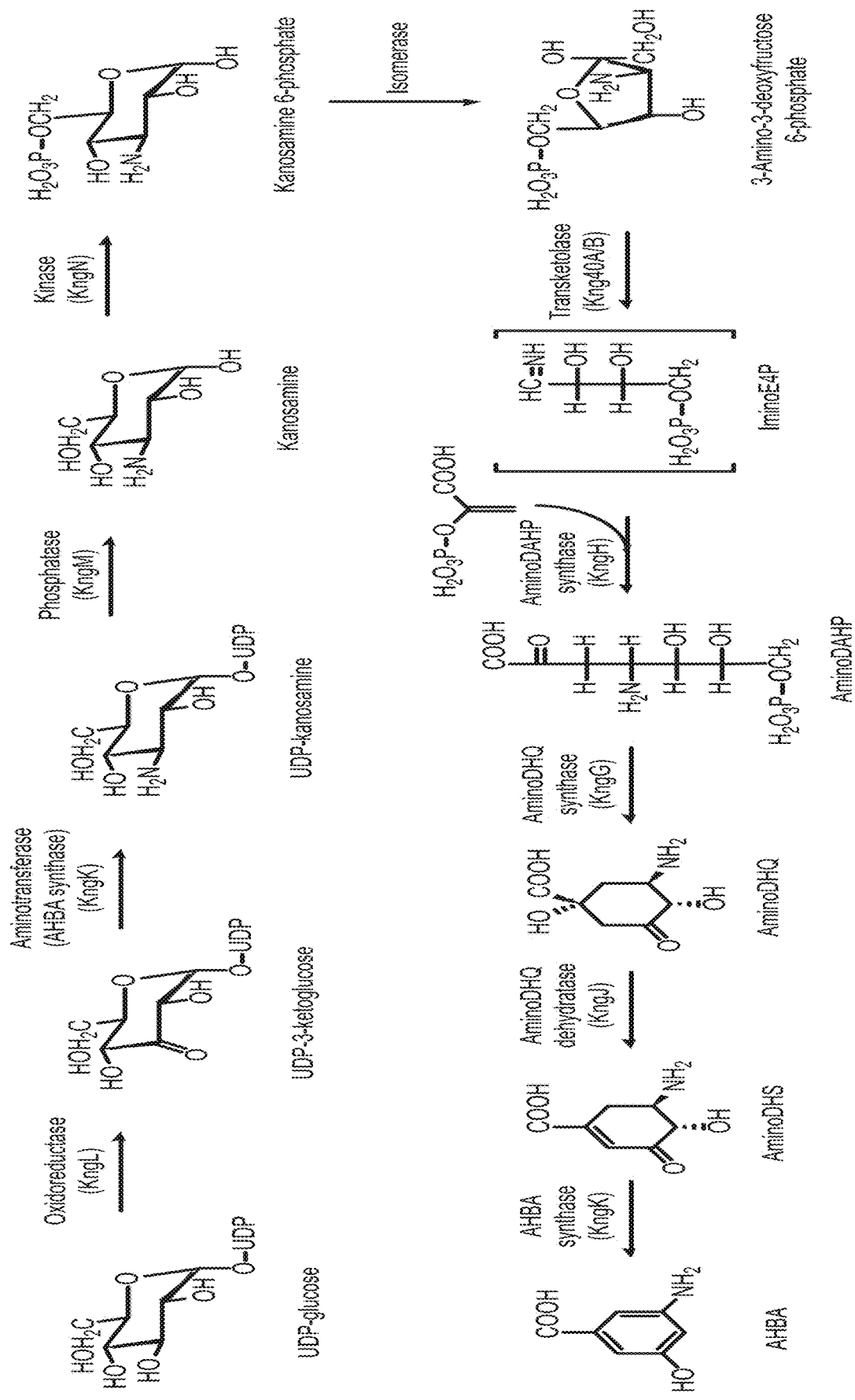
FIG. 24 depicts the proposed biosynthesis of 3-amino-5-hydroxybenzoic acid (AHBA) in Amycolatopsis vancoresmycina. Abbreviations: UPD, uridine diphosphate; iminoE4P, 1-deoxy-1-imino-D-erythrose 4-phosphate; aminoDAHP, 3,4-dideoxy-4-amino-D-arabino-heptulosonate 7-phosphate; aminoDHQ, 5-deoxy-5-amino-3-dehydroquinate; aminoDHS, 5-amino-5-deoxy-3-dehydroshikimate.
Figure 25:
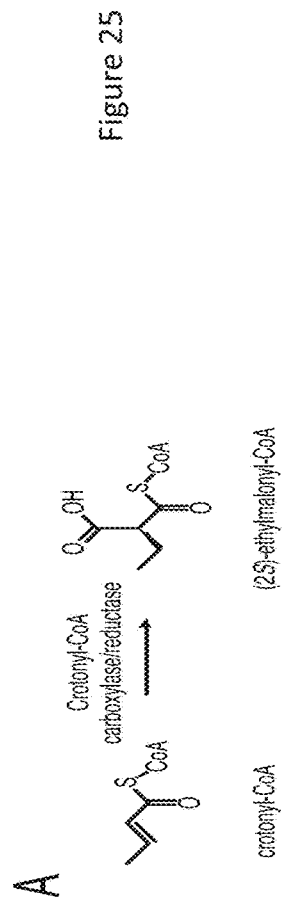
FIG. 25, comprising FIG. 25A through FIG. 25C depicts the proposed biosynthesis of the kanglemycin ethylmalonyl-CoA extender unit and tailoring functionalities in Amycolatopsis vancoresmycina.
Figure 25:
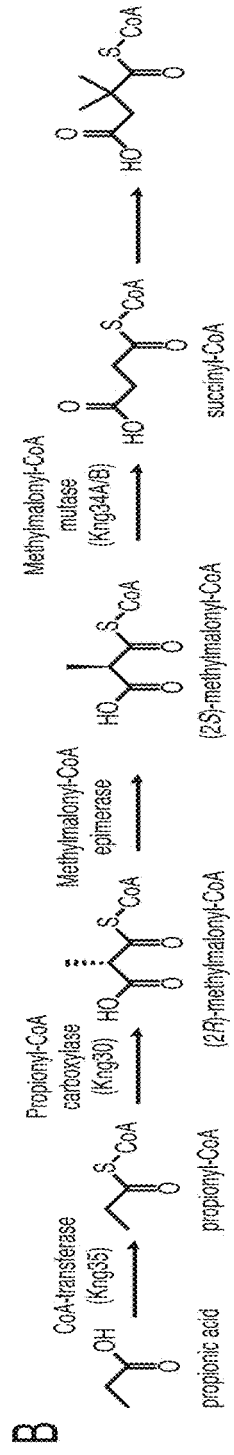
Figure 25:
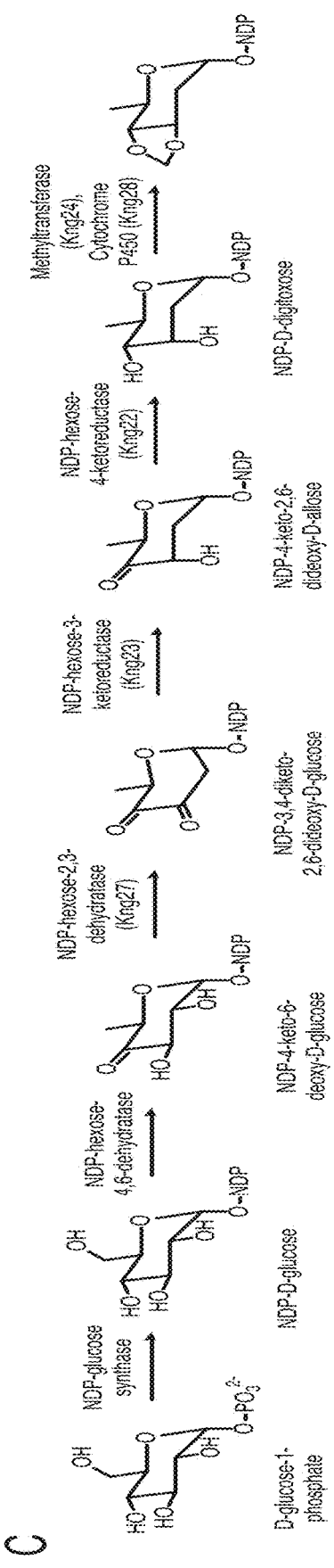
Figure 26:
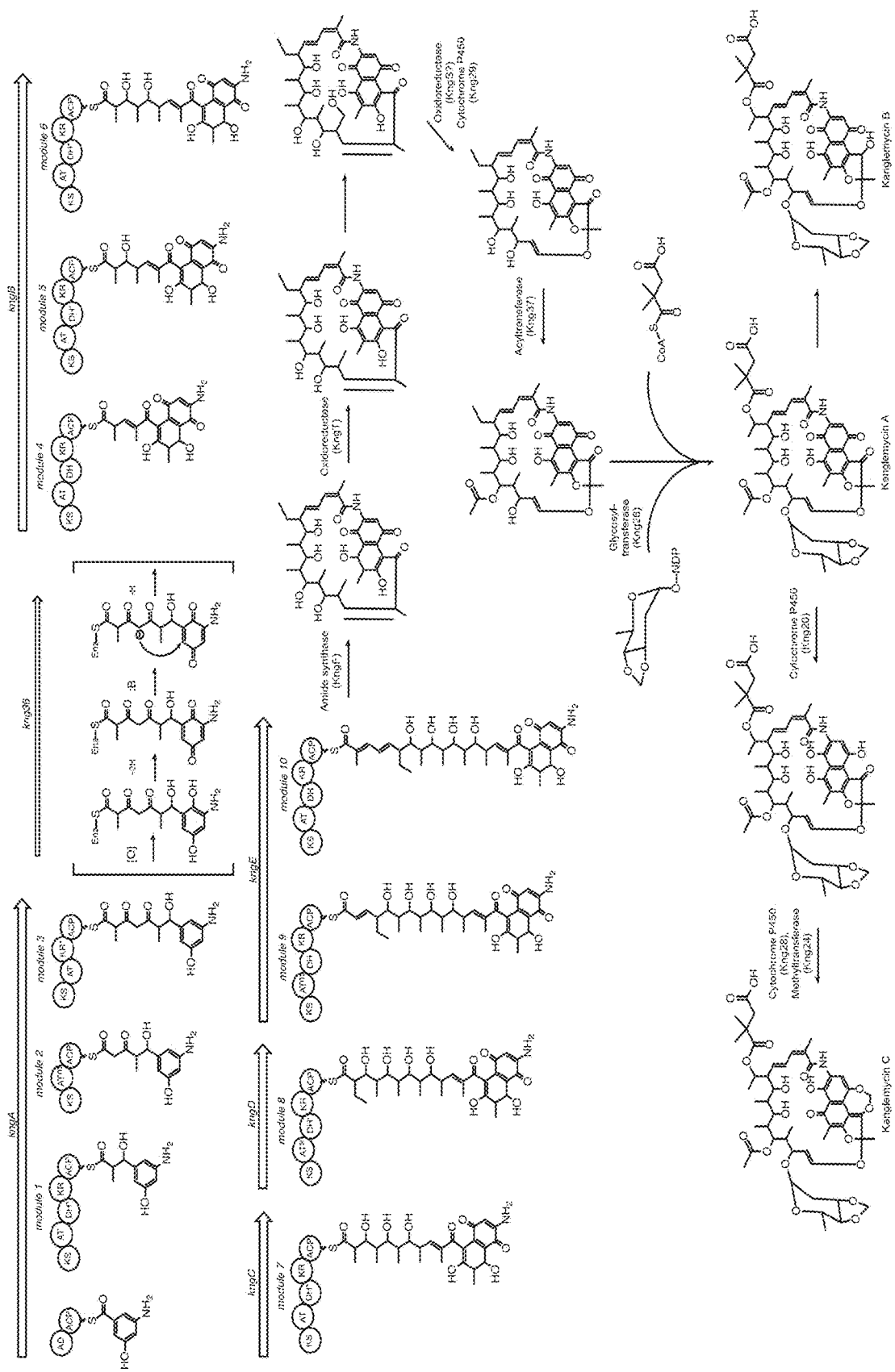
FIG. 26 depicts the proposed biosynthesis and tailoring of the kanglemycin polyketide core in Amycolatopsis vancoresmycina. Polyketide synthase domains that are predicted to be non-functional based on the final structures of the kanglemycins are marked with an asterisk. Abbreviations: AD, adenylation domain; ACP, acyl carrier protein, KS, ketosynthase; $AT^m$, malonyl-CoA specific acyltransferase; $AT^e$, ethylmalonyl-CoA specific acyltransferase (all other AT domains are predicted to utilize methylmalonyl-CoA), KR, ketoreductase; DH, dehydratase.

The potent mutant specific activity of kanglemycins V1 and V2 against common mutations that confer resistance to rifamycin family antibiotics suggests that they may have arisen in response to prevalent resistance phenotypes in the producing bacterium's natural environment. An examination of gene clusters recovered from soil metagenomes provides potential insight into how these molecules could have evolved from an ancestral rifamycin-like gene cluster through a series of horizontal gene transfer events. The simplest kng related gene cluster that was identified (RifCon 12) contains additional biosynthetic genes, not seen in other rifamycin congener gene clusters, that it is believed are required for the biosynthesis and transfer of the digitoxose deoxysugar (kng22, kng23, kng24, kng27, kng28 and kng26) as well as the methylenedioxy bridge on the naphthohydroquinone seen in kanglemycin V2 (kng24 and kng28; FIG. 10). This gene cluster does not, however, contain any genes predicted to encode for the incorporation of either EmaI or the succinic acid moiety seen in the kanglemycins. It is possible that this simpler gene cluster arose from a kng-like gene cluster through a series of gene deletion events although it is believed that it is more likely it represents an ancestor of a kng-like gene cluster. The subsequent acquisition of genes that encode for the EmaI and dimethylsuccinic acid modifications would enable the biosynthesis of a fully functionalized kanglemycin (Tables 8 and 9). In total, three complete kng-like gene clusters were identified-two from soil metagenomes (RifCon 6, RifCon 10) and one from a cultured bacterium. Each is predicted to contain a full complement of kng biosynthetic genes differing only by sequence, gene organization and accessory gene content (e.g., pumps, transcription factors, precursor biosynthetic genes, etc.) (FIG. 10, Tables 1, 6, and 7).

TABLE 6

Gene annotations for the metagenomic gene cluster RifCon12 and corresponding genes from the *Amycolatopsis vancoresmycina* kanglemycin cluster.

| Gene Name | Length [aa] | Putative Function Sp. [Homolog Sp.] | % id/% sm | Accession | *A. vanc.* homolog (% id/% sm) |
|---|---|---|---|---|---|
| orf2 | 327 | gfo/Idh/MocA family oxidoreductase [*Micromonospora nigra*] | 84/91 | WP_091080786.1 | kngS (82/89) |
| orf3 | 322 | gfo/Idh/MocA family oxidoreductase [*Micromonospora nigra*] | 68/77 | WP_091080781.1 | kngT (46/55) |
| orf4 | 72 | hypothetical protein [*Actinomadura formosensis*] | 83/87 | WP_084262634.1 | kng35 (65/80) |
| orf5 | 397 | cytochrome P450 [*Actinomadura formosensis*] | 85/92 | WP_067794733.1 | kngR0 (83/91) |
| orf6 | 5225 | polyketide synthase [*Streptomyces albogriseolus*] | 72/79 | AHD24374.1 | kngA (75/82) |
| orf7 | 5181 | polyketide synthase [*Micromonospora halophytica*] | 80/87 | WP_091298529.1 | kngB (77/83) |
| orf8 | 1809 | polyketide synthase [*Streptomyces leeuwenhoeki*] | 78/85 | WP_047121566.1 | kngC (75/83) |
| orf9 | 1785 | polyketide synthase [*Streptomyces subrutilus*] | 71/80 | WP_069922302.1 | kngD (67/75) |
| orf10 | 3449 | polyketide synthase [*Micromonospora halophytica*] | 78/85 | WP_091293672.1 | kngE (75/83) |
| orf11 | 258 | N-acetyltransferase/amide synthase [*Actinomadura formosensis*] | 84/91 | WP_084263055.1 | kngF (74/84) |
| orf12 | 59 | hypothetical protein [*Micromonospora halophytica*] | 35/56 | SCG46356.1 | — |
| orf13 | 354 | aminoDHQ synthase [*Actinomadura formosensis*] | 90/95 | WP_067800067.1 | kngG (87/93) |
| orf14 | 392 | aminoDAHP synthase [*Actinomadura formosensis*] | 84/91 | WP_067800070.1 | kngH (81/87) |
| orf15 | 307 | shikimate dehydrogenase [*Actinomadura formosensis*] | 85/90 | WP_067800073.1 | kngI (81/86) |
| orf16 | 386 | AHBA synthase [*Actinomadura formosensis*] | 89/94 | WP_067800076.1 | kngK (88/93) |
| orf17 | 362 | gfo/Idh/MocA family oxidoreductase [*Micromonospora rifamycinica*] | 86/91 | WP_067307269.1 | kngL (80/88) |
| orf18 | 232 | phosphoglycolate phosphatase [*Micromonospora halophytica*] | 87/93 | WP_091293655.1 | kngM (86/90) |
| orf19 | 299 | kanosamine kinase [*Streptomyces katrae*] | 77/84 | WP_030293822.1 | kngN (78/86) |
| orf20 | 513 | 3-(3-hydroxyphenyl)propionate hydroxylase [*Streptomyces katrae*] | 82/88 | WP_030293823.1 | kngR19 (74/81) |
| orf21 | 419 | Cytochrome P450 [*Micromonospora nigra*] | 72/84 | SCL21807.1 | kngR16 (71/83) |
| orf22 | 201 | dTDP-4-keto-6-deoxy-D-glucose epimerase [*Streptomyces lydicus*] | 71/81 | WP_069568944.1 | — |
| orf23 | 434 | lipopolysaccharide biosynthesis protein RfbH [*Actinomadura rifamycini*] | 85/92 | WP_026404034.1 | — |
| orf24 | 324 | gfo/Idh/MocA family oxidoreductase [*Actinomadura formosensis*] | 76/86 | WP_084263057.1 | — |
| orf25 | 146 | aminoDHQ synthase [*Actinomadura formosensis*] | 88/94 | WP_067800109.1 | kngJ (90/93) |
| orf26 | 442 | aspartate aminotransferase family protein [*Micromonospora nigra*] | 80/90 | WP_091080812.1 | — |
| orf27 | 376 | UDP:flavonoid glycosyltransferase YjiC, YdhE family [*Micromonospora rifamycinica*] | 68/84 | SCG35582.1 | kngR7 (57/76) |
| orf28 | 116 | hypothetical protein [*Actinokineospora enzanensis*] | 67/79 | WP_018680276.1 | — |
| orf29 | 303 | nucleoside-diphosphate sugar epimerase [*Actinomadura rifamycini*] | 84/93 | WP_026403439.1 | — |
| orf30 | 405 | cytochrome P450 [*A. mediterranei*] | 79/89 | WP_013228164.1 | kngR4 (49/65) |
| orf31 | 258 | thioesterase [*Micromonospora nigra*] | 78/85 | WP_091080824.1 | kngR (75/83) |

TABLE 6-continued

Gene annotations for the metagenomic gene cluster RifCon12 and corresponding genes from the *Amycolatopsis vancoresmycina* kanglemycin cluster.

| Gene Name | Length [aa] | Putative Function Sp. [Homolog Sp.] | % id/% sm | Accession | *A. vanc.* homolog (% id/% sm) |
|---|---|---|---|---|---|
| orf32 | 420 | cytochrome P450 [*A. mediterranei*] | 88/93 | WP_013222567.1 | kngR5 (87/93) |
| orf34 | 408 | LuxR family transcriptional regulator [*Micromonospora rifamycinica*] | 73/82 | SCG35671.1 | kngR36 (68/76) |
| orf35 | 385 | LuxR family transcriptional regulator [*Micromonospora halophytica*] | 75/83 | WP_091293625.1 | kngR36 (68/77) |
| orf36 | 253 | NDP-hexose 4-ketoreductase [*Streptomyces* sp. NRRL S-350] | 77/86 | WP_030241082.1 | kng4 (81/87) |
| orf37 | 354 | aldo/keto reductase [*A. vancoresmycina*] | 84/90 | WP_004562643.1 | kng5 (84/90) |
| orf38 | 255 | NDP-hexose 3-O-methyltransferase [*A. vancoresmycina*] | 91/97 | WP_004562642.1 | kng6 (91/96) |
| orf39 | 383 | dNTP-hexose glycosyl transferase [*A. vancoresmycina*] | 77/87 | WP_004562640.1 | kngR7 (78/86) |
| orf40 | 230 | transketolase [*Salinispora arenicola*] | 81/88 | WP_029021589.1 | kngR15A (71/82) |
| orf41 | 312 | transketolase [*Actinomadura formosensis*] | 78/89 | WP_067800099.1 | kngR15B (72/84) |
| orf42 | 421 | cytochrome P450 [*A. mediterranei*] | 75/85 | WP_014466580.1 | kngR16 (72/82) |
| orf43 | 656 | copper oxidase [*Micromonospora halophytica*] | 85/90 | WP_091298550.1 | kng12 (70/80) |
| orf44 | 476 | NDP-hexose 2,3-dehydratase [*A. vancoresmycina*] | 89/95 | WP_004562638.1 | kngR18 (89/95) |
| orf45 | 429 | acetyltransferase [*Micromonospora nigra*] | 70/80 | SCL21819.1 | kngR20 (65/75) |
| orf46 | 386 | cytochrome P450 [*A. vancoresmycina*] | 77/87 | WP_004562636.1 | kng10 (78/86) |

TABLE 7

Gene annotations for the metagenomic gene cluster RifCon6 and corresponding genes from the *Amycolatopsis vancoresmycina* kanglemycin cluster.

| Gene Name | Length [aa] | Putative Function [Homolog Sp.] | % id/% sm | Accession | *A. vanc.* homolog (% id/% sm) |
|---|---|---|---|---|---|
| orf8 | 459 | crotonyl-CoA carboxylase/reductase [*Actinokineospora enzanensis*] | 84/91 | WP_033400639.1 | |
| orf9 | 348 | gfo/Idh/MocA family oxidoreductase [*Micromonospora nigra*] | 84/92 | WP_091080786.1 | kngS (82/89) |
| orf10 | 322 | gfo/Idh/MocA family oxidoreductase [*Micromonospora nigra*] | 69/78 | WP_091080781.1 | kngT (49/56) |
| orf11 | 397 | cytochrome P450 [*Actinomadura formosensis*] | 85/92 | WP_067794733.1 | kngR0 (83/91) |
| orf12 | 5188 | polyketide synthase [*Streptomyces albogriseolus*] | 72/79 | AHD24374.1 | kngA (75/82) |
| orf13/14 | 4875 | polyketide synthase [*Micromonospora halophytica*] | 73/80 | WP_091298529.1 | kngB (78/85) |
| orf15 | 1805 | polyketide synthase [*Micromonospora nigra*] | 77/86 | WP_091090512.1 | kngC (78/85) |
| orf16 | 1836 | polyketide synthase [*A. vancoresmycina*] | 78/85 | WP_003102381.1 | kngD (77/85) |
| orf17/18 | 3498 | polyketide synthase [*Micromonospora halophytica*] | 76/83 | EOD65140.1 | kngE (74/82) |

TABLE 7-continued

Gene annotations for the metagenomic gene cluster RifCon6 and corresponding genes from the *Amycolatopsis vancoresmycina* kanglemycin cluster.

| Gene Name | Length [aa] | Putative Function [Homolog Sp.] | % id/% sm | Accession | *A. vanc.* homolog (% id/% sm) |
|---|---|---|---|---|---|
| orf19 | 258 | N-acetyltransferase/amide synthase [*Actinomadura formosensis*] | 82/90 | WP_084263055.1 | kngF (73/82) |
| orf20 | 61 | response regulator [*Vibrio coralliilyticus*] | 41/59 | WP_095571655.1 | — |
| orf21 | 350 | aminoDHQ synthase [*Actinomadura formosensis*] | 89/95 | WP_067800067.1 | kngG (86/92) |
| orf22 | 392 | aminoDAHP synthase [*Actinomadura formosensis*] | 84/91 | WP_067800070.1 | kngH (82/87) |
| orf23 | 284 | shikimate dehydrogenase [*Actinomadura formosensis*] | 84/89 | WP_067800073.1 | kngI (81/86) |
| orf24 | 386 | AHBA synthase [*Actinomadura formosensis*] | 89/94 | WP_067800076.1 | kngK (87/92) |
| orf25 | 356 | gfo/Idb/MocA family oxidoreductase [*Micromonospora rifamycinica*] | 86/91 | WP_067307269.1 | kngL (80/88) |
| orf26 | 232 | phosphoglycolate phosphatase [*Micromonospora halophytica*] | 88/93 | WP_091293655.1 | kngM (86/91) |
| orf27 | 299 | kanosamine kinase [*Streptomyces subrutilus*] | 77/86 | WP_069922309.1 | kngN (78/86) |
| orf28 | 513 | 3-(3-hydroxyphenyl)propionate hydroxylase [*Streptomyces katrae*] | 82/88 | WP_030293823.1 | kngR19 (74/82) |
| orf29 | 396 | cytochrome P450 [*A. vancoresmycina*] | 76/85 | WP_003062297.1 | kngR4 (76/85) |
| orf30 | 1082 | hypothetical protein [*A. vancoresmycina*] | 82/87 | WP_051767686.1 | kng2 (82/87) |
| orf31 | 588 | ABC transporter ATP-binding protein [*A. vancoresmycina*] | 79/89 | WP_051767685.1 | kng14 (79/89) |
| orf32 | 594 | ABC transporter ATP-binding protein [*A. vancoresmycina*] | 80/89 | WP_003071800.1 | kng17 (80/89) |
| orf33 | 525 | methylmalonyl-CoA mutase [*A. vancoresmycina*] | 92/96 | WP_033261449.1 | kng18A (92/96) |
| orf34 | 136 | cobalamin B12-binding domain-containing protein [*A. vancoresmycina*] | 90/93 | WP_003071791.1 | kng18B (90/93) |
| orf35 | 519 | acyl-CoA carboxylase subunit beta [*A. vancoresmycina*] | 91/96 | WP_004562633.1 | kng11 (91/96) |
| orf36 | 248 | thioesterase [*Micromonospora rifamycinica*] | 79/87 | WP_067307207.1 | kngR (71/82) |
| orf37 | 420 | cytochrome P450 [*A. vancoresmycina*] | 85/92 | WP_004562634.1 | kngR5 (85/92) |
| orf38 | 408 | regulatory protein, luxR family [*Micromonospora rifamycinica*] | 71/82 | SCG35671.1 | kngR36 (67/77) |
| orf39 | 145 | aminoDHQ synthase [*Actinomadura formosensis*] | 89/94 | WP_067800109.1 | kngJ (91/96) |
| orf40 | 357 | LuxR family transcriptional regulator [*Micromonospora halophytica*] | 77/84 | WP_091293625.1 | kngR36 (69/77) |

TABLE 7-continued

Gene annotations for the metagenomic gene cluster RifCon6 and corresponding genes from the *Amycolatopsis vancoresmycina* kanglemycin cluster.

| Gene Name | Length [aa] | Putative Function [Homolog Sp.] | % id/% sm | Accession | *A. vanc.* homolog (% id/% sm) |
|---|---|---|---|---|---|
| orf41 | 194 | YceI family protein [*Yuhushiella deserti*] | 62/76 | WP_092529286.1 | — |
| orf42 | 253 | NDP-hexose 4-ketoreductase [*Streptomyces* sp. NRRL S-350] | 78/87 | WP_030241082.1 | kng3 (78/85) |
| orf43 | 329 | aldo/keto reductase [*A. vancoresmycina*] | 86/92 | WP_004562643.1 | kng4 (86/92) |
| orf44 | 255 | NDP-hexose 3-0-methyltransferase [*A. vancoresmycina*] | 93/97 | WP_004562642.1 | kng6 (93/97) |
| orf45 | 326 | stationary phase survival protein SurE [*A. mediterranei*] | 76/82 | WP_013225304.1 | kng7 (73/83) |
| orf46 | 383 | hypothetical protein [*A. vancoresmycina*] | 81/91 | WP_004562640.1 | kngR7 (81/91) |
| orf47 | 215 | transketolase [*Salinispora arenicola*] | 83/90 | WP_029021589.1 | kngR15A (74/84) |
| orf48 | 316 | transketolase [*Actinomadura formosensis*] | 77/88 | WP_067800099.1 | kngR15B (72/83) |
| orf49 | 426 | cytochrome P450 [*A. mediterranei*] | 76/86 | WP_014466580.1 | kngR16 (72/83) |
| orf50 | 658 | copper oxidase [*Micromonospora halophytica*] | 81/88 | WP_091298550.1 | kng12 (73/84) |
| orf51 | 474 | NDP-hexose 2,3-dehydratase [*A. vancoresmycina*] | 89/94 | WP_004562638.1 | kngR18 (89/94) |
| orf52 | 419 | acyltransferase [*Actinomadura formosensis*] | 70/80 | WP_067800088.1 | kngR20 (67/77) |
| orf53 | 388 | cytochrome P450 [*A. vancoresmycina*] | 82/91 | WP_004562636.1 | kng10 (82/91) |

TABLE 8

Gene annotations for the kanglemycin biosynthetic gene cluster from *Amycolatopsis vancoresmycina* and corresponding genes from the *Amycolatopsis mediterranei* rifamycin cluster.

| Gene Name | Length [aa] | Putative Function [Homolog Sp.] | % id/% sm | Accession | *A. mediterranei* homolog (% id/% sm) |
|---|---|---|---|---|---|
| kngS | 330 | gfo/Idh/MocA family oxidoreductase [*A. mediterrunei*] | 87/92 | WP_01322543.1 | rifS (87/92) |
| kngT | 255 | gfo/Idh/MocA family oxidoreductase [*A kentuckyensis*] | 82/88 | WP_086852324.1 | rifT (80/85) |
| kng3 | 83 | hypothetical protein [*A. mediterranei*] S6991 | 84/90 | AAC01708.1 | rif35 (84/90) |
| kng4 | 396 | cytochrome P450 [*A kentuckyensis*] | 92/95 | WP_08682320.1 | rif0 (91/94) |
| kngA | 4758 | polyketide synthase [*A. mediterranei*] | 90/93 | WP_01322547.1 | rifA (90/93) |
| kngB | 5064 | polyketide synthase [*A kentuckyensis*] | 91/94 | WP_08681069.1 | rifB (90/93) |
| kngC | 1810 | polyketide synthase [*Micromonospora nigra*] | 77/85 | WP_09100512.1 | rifC (77/83) |
| kngD | 1824 | polyketide synthase [*Streptomyces subrutilus*] | 66/76 | WP_06992302.1 | rifD (64/72) |
| kngE | 3448 | polyketide synthase [*A kentuckyensis*] | 78/85 | WP_08681059.1 | rifE (78/84) |
| kngF | 258 | N-acetyltransferase/amide synthase [*A kentuckyensis*] | 85/91 | WP_086841057.1 | rifF (85/90) |
| kng11 | 62 | hypothetical protein [*A. mediterranei*] | 84/94 | WP_013222553.1 | rifI (84/94) |
| kngG | 351 | aminoDHQ synthase [*A kentuckyensis*] | 89/93 | WP_086841053.1 | rifG (87/90) |

TABLE 8-continued

Gene annotations for the kanglemycin biosynthetic gene cluster from
*Amycolatopsis vancoresmycina* and corresponding genes from the *Amycolatopsis
mediterranei* rifamycin cluster.

| Gene Name | Length [aa] | Putative Function [Homolog Sp.] | % id/% sm | Accession | *A. mediterranei* homolog (% id/% sm) |
|---|---|---|---|---|---|
| kngH | 418 | aminoDAHP synthase [*Actinomadura formosensis*] | 81/89 | WP_067800070.1 | rifH (71/77) |
| kngI | 270 | shikimate dehydrogenase [*A. mediterranei*] | 84/87 | WP_013222556.1 | rifI (84/87) |
| kng15 | 68 | hypothetical protein, conserved [*Trypanosoma equiperdum*] | 47/65 | SCU70316.1 | — |
| kngK | 386 | AHBA synthase [*Streptomyces leeuwenhoekii*] | 84/91 | WP_029387788.1 | rifK (83/89) |
| kngL | 357 | gfo/Idh/MocA family oxidoreductase [*Micromonospora rifamycinica*] | 79/86 | WP_067307269.1 | rifL (77/86) |
| kngM | 232 | phosphoglycolate phosphatase [*Micromonospora halophytica*] | 88/93 | WP_091293655.1 | rifM (88/91) |
| kngN | 294 | kanosamine kinase [*A kentuckyensis*] | 74/83 | WP_086841040.1 | rifN (70/81) |
| kng20 | 398 | cytochrome P450 [*Streptomyces leeuwenhoekii*] | 60/72 | WP_029387780.1 | rif4 (47/64) |
| kng21 | 1055 | hypothetical protein (peptidase S41) [*Streptomyces griseoplanus*] | 48/61 | WP_055589579.1 | — |
| kng22 | 253 | NDP-hexose-4-ketoreductase [*Streptomyces* sp. NRRL S-350] | 75/84 | WP_030241082.1 | — |
| kng23 | 353 | NDP-hexose-3-ketoreductase [*Streptomyces* sp. NRRL S-350] | 78/86 | WP_030241085.1 | — |
| kng24 | 255 | NDP-hexose 3-O-methyltransferase [*Streptomyces puniciscabiei*] | 87/94 | WP_069778168.1 | — |
| kng25 | 326 | stationary phase survival protein SurE [*A. mediterranei*] | 75/85 | WP_013225304.1 | — |
| kng26 | 383 | dNTP-hexose glycosyl transferase [*Actinomadura rifamycini*] | 68/81 | WP_084550726.1 | rif7 (60/73) |
| kng27 | 474 | NDP-hexose 2,3-dehydratase [*Plantactinospora* sp. KBS50] | 60/74 | WP_095567734.1 | rif18 (55/68) |
| kng28 | 378 | cytochrome P450 [*Streptomyces*] | 55/71 | WP_052857194.1 | — |
| kng29 | 421 | cytochrome P450 [*A. mediterranei*] | 81/89 | WP_013222567.1 | rif5 (81/89) |
| kng30 | 531 | propionyl-CoA carboxylase [*Lechevalieria aerocolonigenes*] | 71/82 | WP_030473366.1 | — |
| kng31 | 665 | copper oxidase [*Micromonospora halophytica*] | 71/81 | WP_091298550.1 | — |
| kng32 | 589 | ABC transporter ATP-binding protein [*Glycomyces tenuis*] | 62/78 | WP_081687411.1 | — |
| kng33 | 594 | ABC transporter ATP-binding protein [*Stackebrandtia nassauensis*] | 62/79 | WP_013021481.1 | — |
| kng34A | 525 | methylmalonyl-CoA mutase [*Streptomyces fulvoviolaceus*] | 87/94 | WP_030598014.1 | — |
| kng34B | 131 | cobalamin B12-binding domain-containing protein [*Frankia* sp. EI5c] | 84/96 | WP_066061192.1 | — |
| kng35 | 344 | crotonobetainyl-CoA:carnitine CoA-transferase CaiB [*Streptomyces olivochromogenes*] | 83/92 | WP_067374600.1 | — |
| kng36 | 484 | 3-(3-hydroxyphenyl)propionate hydroxylase [*A kentuckyensis*] | 85/89 | WP_086852066.1 | rif19 (85/88) |
| kng37 | 392 | acyltransferase [*A. mediterranei*] | 83/90 | WP_013222577.1 | rif20 (83/90) |
| kngR | 245 | thioesterase [*A. mediterranei*] | 90/94 | WP_013222578.1 | rifR (90/94) |
| kng39 | 422 | cytochrome P450 [*A rifamycinica*] | 90/95 | WP_084093545.1 | rif13 (90/94) |
| kng40A | 231 | transketolase [*A tolypomycina*] | 82/88 | WP_091304035.1 | rif15A (80/86) |
| kng40B | 303 | transketolase [*A rifamycinica*] | 87/91 | WP_084093546.1 | rif15B (87/91) |
| kng41 | 419 | cytochrome P450 [*A. mediterranei*] | 79/89 | WP_014466580.1 | rif16 (79/89) |

TABLE 8-continued

Gene annotations for the kanglemycin biosynthetic gene cluster from
Amycolatopsis vancoresmycina and corresponding genes from the Amycolatopsis
mediterranei rifamycin cluster.

| Gene Name | Length [aa] | Putative Function [Homolog Sp.] | % id/ % sm | Accession | A. mediterranei homolog (% id/% sm) |
|---|---|---|---|---|---|
| kngJ | 149 | aminoDHQ synthase [A rifamycinica] | 91/94 | WP_043781867.1 | rifJ (90/93) |
| kng43 | 425 | LuxR family transcriptional regulator [A. mediterranei S699] | 85/91 | AEK39161.1 | rif36 (85/91) |

TABLE 9

Rifamycin biosynthetic genes not found in the kanglemycin biosynthesis gene cluster.

| Gene Name | Length [aa] | Putative Function | Accession |
|---|---|---|---|
| rifO | 255 | GlcNAc-PI de-N-acetylase | WP_013222561.1 |
| rif2 | 310 | alpha/beta hydrolase | WP_013222562.1 |
| rifP | 522 | MFS transporter | AAC01725.1 |
| rifQ | 242 | TetR family transcriptional regulator | WP_013222564.1 |
| rif3 | 162 | pyridoxamine 5'-phosphate oxidase | WP_013222565.1 |
| rif6 | 435 | putative dNTP-hexose dehydratase | WP_013222568.1 |
| rif8 | 206 | putative dNTP-hexose 3,5-epimerase | AAS07755.1 |
| rif9 | 430 | dNTP-hexose aminotransferase | AAC01733.1 |
| rif10 | 322 | putative dNTP-hexose 3-ketoreductase | AAC01734.1 |
| rif11 | 294 | flavin-dependent oxidoreductase | WP_013222573.1 |
| rif17 | 351 | putative alpha-chain alkanal monooxygenase | AAG52987.1 |
| rif14 | 272 | C-27 O-methyltransferase | AAC01738.1 |

Efforts to improve rifamycin through semisynthesis have been most productive when focusing on modifications of the naphthohydroquinone (Ma et al., *Comprehensive Medicinal Chemistry II*, 2006; Vol. 7, pp 699-739; Bacchi et al., 1998, J. Med. Chem., 41:2319-2332; Sensi, P., 1983, Rev. Infect. Dis., 5 Suppl. 3:S402-S406, which are incorporated by reference herein in their entireties). Modification of the naphthohydroquinone has yielded the clinically used drugs rifampicin, rifapentine, rifabutin and rifaximin. Interestingly, in the case of the kanglemycins, evolution has led to the creation of biologically interesting congeners modified at three different positions, all of which have either been largely inaccessible or unproductive in semi-synthesis studies. The polyketide backbone has been a particularly challenging region of rifamycin to modify by semi-synthesis. The free carboxylic acid that appears on the succinic acid moiety in the kanglemycins provides a facile entry point for generating large numbers of semi-synthetic derivatives off the previously inaccessible polyketide backbone.

While it is not known for certain that the evolution of the kanglemycins provides a selective advantage to the producing organisms in an ecological niche populated by rifamycin resistant bacteria, their activity against this phenotype suggests this is likely to be the case. Competition between environmental bacteria may have provided strong evolutionary pressure to evolve antibiotic variants that are capable of circumventing common resistant mechanisms, including many that are likely relevant to human health. Large-scale metagenome sequencing methods, like those used here, allow for the systematic identification of the most complex gene clusters in known antibiotic families, which, it is believed, will often represent the most evolved natural solutions to commonly encountered antibiotic resistance mechanisms. If this proves true across other families of gene clusters that encode antibiotics, a systematic examination of the global microbiome for new congeners of antibiotics would likely uncover additional natural products capable of circumventing common clinically important antibiotic resistance mechanisms.

While this disclosure has been disclosed with reference to specific embodiments, it is apparent that other embodiments and variations of this disclosure may be devised by others skilled in the art without departing from the true spirit and scope of the disclosure. The appended claims are intended to be construed to include
all such embodiments and equivalent variations.

What is claimed is:

1. A compound of formula (1):

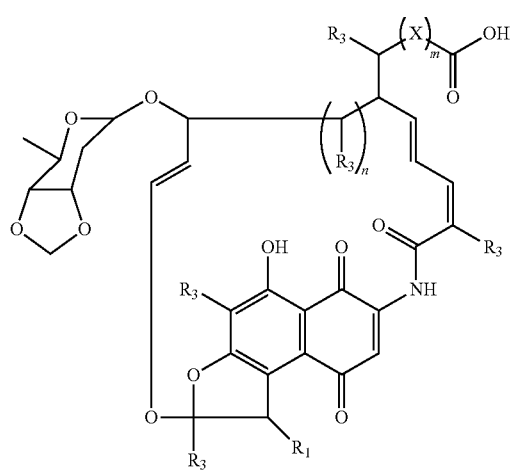

wherein:
- $R_1$ is $CHR_4R_5$ or $OR_6$;
- each occurrence of $R_4$ and $R_5$ independently is a hydrogen atom, a halogen atom, alkyl, cycloalkyl, aryl, or heteroaryl;
- $R_6$ is a hydrogen atom, alkyl, cycloalkyl, aryl, or heteroaryl;
- each occurrence of $R_3$ independently is a hydrogen atom, a halogen atom, alkyl, cycloalkyl, aryl, or heteroaryl, or $OR_7$;
- $R_7$ is a hydrogen atom, alkyl, cycloalkyl, aryl, heteroaryl, or $C(=O)R_8$;
- $R_8$ is alkyl, cycloalkyl, aryl, or heteroaryl;
- X represents —O—, —$NR_9$—, —$CR_9R_{10}$—, or —C(=O)—;
- $R_9$ and $R_{10}$ each independently is a hydrogen atom, a halogen atom, alkyl, cycloalkyl, aryl, or heteroaryl:
- m is an integer from 1 to 6; and
- n is an integer from 4 to 10;

or a salt thereof.

2. The compound of claim 1, wherein $R_1$ is $OR_6$.

3. The compound of claim 1, wherein each $R_3$ independently is alkyl, OH, or —OC(=O)$CH_3$.

4. The compound of claim 1, wherein each $R_7$ independently is a hydrogen atom or C(=O)$R_8$.

5. The compound of claim 1, wherein $R_8$ is alkyl.

6. The compound of claim 1, wherein each occurrence of X independently is —O—, —$CR_9R_{10}$—, or —C(=O)—, and wherein each occurrence of $R_9$ and $R_{10}$ independently is a hydrogen atom or alkyl.

7. The compound of claim 1, wherein the compound is

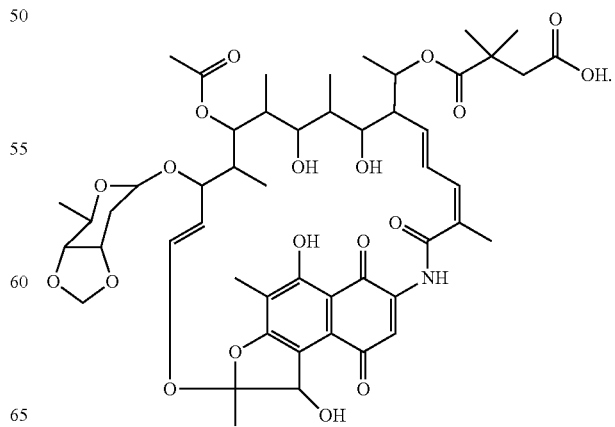

8. A compound of formula (2):

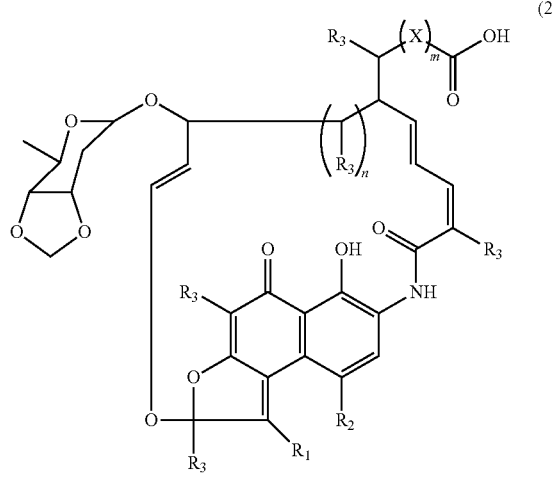

wherein:
$R_1$ and $R_2$ each independently is $CHR_4R_5$, $CR_4R_5$, $OR_6$, or O, wherein $R_1$ and $R_2$ may optionally be joined to form a ring;
each occurrence of $R_4$ and $R_5$ independently is a hydrogen atom, a halogen atom, alkyl, alkylene, cycloalkyl, aryl, or heteroaryl;
each occurrence of $R_6$ independently is a hydrogen atom, alkyl, alkylene, cycloalkyl, aryl, or heteroaryl;
each occurrence of $R_3$ independently is a hydrogen atom, a halogen atom, alkyl, cycloalkyl, aryl, or heteroaryl, or $OR_7$;
$R_7$ is a hydrogen atom, alkyl, cycloalkyl, aryl, heteroaryl, or $C(=O)R_8$;
$R_8$ is alkyl, cycloalkyl, aryl, or heteroaryl;
X is O, $NR_9$, $CR_9R_{10}$, or $C(=O)$;
$R_9$ and $R_{10}$ each independently is a hydrogen atom, a halogen atom, alkyl, cycloalkyl, aryl, or heteroaryl;
m is an integer from 1 to 6; and
n is an integer from 4 to 10;
or a salt thereof.

9. The compound of claim 8, wherein $R_1$ and $R_2$ each independently are $OR_6$.

10. The compound of claim 9, wherein each $R_6$ independently is a hydrogen atom or alkyl.

11. The compound of claim 8, wherein $R_1$ and $R_2$ each independently is $OR_6$ and or O, and $R_1$ and $R_2$ are joined to form a ring.

12. The compound of claim 8, wherein each $R_3$ independently is alkyl, —OH, or —OC(=O)$CH_3$.

13. The compound of claim 8, wherein each $R_7$ independently is a hydrogen atom or $C(=O)R_8$.

14. The compound of claim 8, wherein $R_8$ is alkyl.

15. The compound of claim 8, wherein each occurrence of X independently is —O—, —$CR_9R_{10}$—, or —C(=O)—.

16. The compound of claim 8, wherein each occurrence of $R_9$ and $R_{10}$ independently are a hydrogen atom or alkyl.

17. The compound of claim 8, wherein the compound is

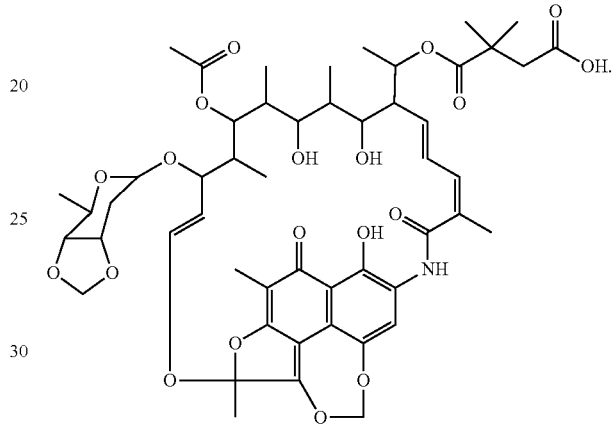

18. A pharmaceutical composition comprising a therapeutically effective amount of a compound of claim 1 and a pharmaceutically acceptable excipient.

19. A method of reducing the growth or proliferation of a microorganism, wherein the method comprises contacting the microorganism with a composition comprising a compound of claim 1.

20. A method of treating a bacterial infection in a subject, wherein the method comprises administering to the subject a composition comprising a compound of claim 1.

* * * * *